US011896636B2

(12) United States Patent
Geall et al.

(10) Patent No.: US 11,896,636 B2
(45) Date of Patent: Feb. 13, 2024

(54) # IMMUNOGENIC COMBINATION COMPOSITIONS AND USES THEREOF

(75) Inventors: Andrew Geall, Littleton, MA (US); Ethan Settembre, Lexington, MA (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 14/130,899

(22) PCT Filed: Jul. 6, 2012

(86) PCT No.: PCT/US2012/045847

§ 371 (c)(1), (2), (4) Date: Apr. 7, 2014

(87) PCT Pub. No.: WO2013/006838

PCT Pub. Date: Jan. 10, 2013

(65) Prior Publication Data

US 2014/0227346 A1 Aug. 14, 2014

Related U.S. Application Data

(60) Provisional application No. 61/505,093, filed on Jul. 6, 2011.

(51) Int. Cl.

| | |
|---|---|
| ***A61K 39/245*** | (2006.01) |
| ***A61K 39/23*** | (2006.01) |
| ***A61K 35/76*** | (2015.01) |
| ***A61K 35/763*** | (2015.01) |
| ***A61K 39/12*** | (2006.01) |
| *A61K 39/00* | (2006.01) |

(52) U.S. Cl.

CPC ............ *A61K 35/763* (2013.01); *A61K 35/76* (2013.01); *A61K 39/12* (2013.01); *A61K 39/23* (2013.01); *A61K 39/245* (2013.01); *A61K 2039/5258* (2013.01); *A61K 2039/53* (2013.01); *A61K 2039/55566* (2013.01); *A61K 2039/70* (2013.01); *C12N 2710/16134* (2013.01); *C12N 2750/14223* (2013.01); *C12N 2750/14234* (2013.01); *C12N 2770/36143* (2013.01)

(58) Field of Classification Search

None

See application file for complete search history.

(56) References Cited

U.S. PATENT DOCUMENTS

| | | | | |
|---|---|---|---|---|
| 5,013,556 | A | 5/1991 | Woodle et al. | |
| 5,279,833 | A | 1/1994 | Rose | |
| 5,459,127 | A | 10/1995 | Felgner et al. | |
| 5,474,914 | A | 12/1995 | Spaete | |
| 5,750,390 | A | 5/1998 | Thompson et al. | |
| 5,814,482 | A | 9/1998 | Dubensky, Jr. et al. | |
| 5,843,723 | A | 12/1998 | Dubensky, Jr. et al. | |
| 5,885,613 | A | 3/1999 | Holland et al. | |
| 5,965,434 | A | 10/1999 | Wolff et al. | |
| 5,972,704 | A | 10/1999 | Draper et al. | |
| 6,009,406 | A | 12/1999 | Nick | |
| 6,015,686 | A | 1/2000 | Dubensky, Jr. et al. | |
| 6,156,558 | A | 1/2000 | Johnston et al. | |
| 6,048,546 | A | 4/2000 | Sasaki et al. | |
| 6,060,308 | A | 5/2000 | Parrington | |
| 6,090,406 | A | 7/2000 | Popescu et al. | |
| 6,395,302 | B1 | 5/2002 | Hennink et al. | |
| 6,432,926 | B1 | 8/2002 | Hoon et al. | |
| 6,602,705 | B1 | 8/2003 | Barnett et al. | |
| 6,610,321 | B2 | 8/2003 | Huang et al. | |
| 6,790,449 | B2 | 9/2004 | Collins | |
| 6,815,432 | B2 | 11/2004 | Wheeler et al. | |
| 6,858,225 | B2 | 2/2005 | Semple et al. | |
| 6,890,554 | B2 | 5/2005 | Jessee et al. | |
| 7,250,404 | B2 | 7/2007 | Felgner et al. | |
| 7,303,881 | B2 | 12/2007 | Huang et al. | |
| 7,384,923 | B2 | 6/2008 | Gregoriadis | |
| 7,422,902 | B1 | 9/2008 | Wheeler et al. | |
| 7,442,381 | B2 * | 10/2008 | Smith et al. | 424/218.1 |
| 7,557,200 | B2 | 7/2009 | Wu et al. | |
| 7,604,803 | B2 | 10/2009 | Bacon et al. | |
| 7,691,405 | B2 | 4/2010 | Chen et al. | |
| 7,745,651 | B2 | 6/2010 | Heyes et al. | |
| 7,799,565 | B2 | 9/2010 | MacLachlan et al. | |
| 7,811,812 | B2 * | 10/2010 | Dubensky et al. | 435/320.1 |
| 7,862,829 | B2 | 1/2011 | Johnston et al. | |

(Continued)

FOREIGN PATENT DOCUMENTS

| | | | |
|---|---|---|---|
| BR | 112012001666-0 | A2 | 9/2019 |
| EP | 0 786 522 | A2 | 7/1997 |
| EP | 1 083 232 | A1 | 3/2001 |
| EP | 0 880 360 | B1 | 10/2002 |
| EP | 1 392 341 | B1 | 3/2005 |
| EP | 1 637 144 | A1 | 3/2006 |
| EP | 1 764 089 | A1 | 3/2007 |
| EP | 2 338 478 | A1 | 6/2011 |

(Continued)

OTHER PUBLICATIONS

Roldão A, Mellado MC, Castilho LR, Carrondo MJ, Alves PM. Virus-like particles in vaccine development. Expert Rev Vaccines. Oct. 2010;9(10):1149-76.*

(Continued)

*Primary Examiner* — Benjamin P Blumel

(74) *Attorney, Agent, or Firm* — Birch, Stewart, Kolasch & Birch, LLP

(57) ABSTRACT

This invention generally relates to immunogenic compositions that comprise an RNA component and a polypeptide component. Immunogenic compositions that deliver antigens in two different forms—a first antigen from a pathogen, in RNA-coded form; and a second antigen from a different pathogen, in polypeptide form—are effective in inducing immune response to both pathogens.

13 Claims, No Drawings

Specification includes a Sequence Listing.

(56) References Cited

U.S. PATENT DOCUMENTS

| | | | | |
|---|---|---|---|---|
| 7,977,091 | B2 * | 7/2011 | Dubensky et al. | 435/320.1 |
| 8,058,069 | B2 | 11/2011 | Yaworski et al. | |
| 8,338,583 | B2 | 12/2012 | Michaeli | |
| 8,877,206 | B2 | 11/2014 | Chen et al. | |
| 9,254,265 | B2 | 2/2016 | Geall et al. | |
| 9,504,651 | B2 | 11/2016 | MacLachlan et al. | |
| 9,770,463 | B2 | 9/2017 | Geall et al. | |
| 9,801,897 | B2 | 10/2017 | Geall et al. | |
| 10,188,748 | B2 | 1/2019 | Mulbe et al. | |
| 10,487,332 | B2 | 11/2019 | Geall | |
| 10,532,067 | B2 | 1/2020 | Geall et al. | |
| 10,906,867 | B2 | 2/2021 | Brito et al. | |
| 11,026,964 | B2 | 6/2021 | Geall et al. | |
| 11,058,762 | B2 | 7/2021 | Geall et al. | |
| 11,078,237 | B2 | 8/2021 | Franti et al. | |
| 11,291,635 | B2 | 4/2022 | Geall et al. | |
| 11,291,682 | B2 | 4/2022 | Geall et al. | |
| 11,324,770 | B2 | 5/2022 | Geall et al. | |
| 11,638,693 | B2 | 5/2023 | Geall | |
| 2003/0096397 | A1 | 5/2003 | Schlesinger et al. | |
| 2003/0124134 | A1 | 7/2003 | Edwards, Jr. et al. | |
| 2003/0138453 | A1 | 7/2003 | O'Hagan et al. | |
| 2003/0203865 | A1 | 10/2003 | Harvie et al. | |
| 2003/0212022 | A1 | 11/2003 | Vogel et al. | |
| 2003/0232058 | A1 | 12/2003 | Dubensky, Jr. et al. | |
| 2004/0142025 | A1 | 7/2004 | MacLachlan et al. | |
| 2004/0208848 | A1 * | 10/2004 | Smith et al. | 424/93.2 |
| 2004/0228842 | A1 | 11/2004 | Lu et al. | |
| 2005/0032730 | A1 | 2/2005 | Von Der Mulbe et al. | |
| 2005/0042230 | A1 | 2/2005 | Anderson et al. | |
| 2005/0064026 | A1 | 3/2005 | Garidel et al. | |
| 2005/0064595 | A1 | 3/2005 | Maclachlan et al. | |
| 2005/0118566 | A1 | 6/2005 | Escriou et al. | |
| 2005/0266550 | A1 | 12/2005 | Rayner et al. | |
| 2006/0002991 | A1 | 1/2006 | Essler et al. | |
| 2006/0051405 | A1 | 3/2006 | Maclachlan et al. | |
| 2006/0063732 | A1 | 3/2006 | Vogel et al. | |
| 2006/0083780 | A1 | 4/2006 | Heyes et al. | |
| 2006/0177819 | A1 | 8/2006 | Smith et al. | |
| 2006/0240554 | A1 | 10/2006 | Chen et al. | |
| 2006/0251620 | A1 | 11/2006 | Ivanova et al. | |
| 2007/0014805 | A1 | 1/2007 | Delencon et al. | |
| 2007/0118094 | A1 | 5/2007 | Bingham et al. | |
| 2007/0207526 | A1 | 9/2007 | Coit et al. | |
| 2008/0057080 | A1 | 3/2008 | Luke et al. | |
| 2008/0085870 | A1 | 4/2008 | Hermanson et al. | |
| 2008/0187545 | A1 * | 8/2008 | Shenk et al. | 424/159.1 |
| 2008/0249046 | A1 | 10/2008 | MacLachlan et al. | |
| 2008/0260698 | A1 | 10/2008 | Weaver et al. | |
| 2008/0311158 | A1 | 12/2008 | Merola | |
| 2009/0068221 | A1 | 3/2009 | Morrison | |
| 2009/0075384 | A1 | 3/2009 | Kamrud et al. | |
| 2009/0091591 | A1 | 4/2009 | Sivan et al. | |
| 2009/0104226 | A1 | 4/2009 | Perri et al. | |
| 2009/0143323 | A1 | 6/2009 | Bavari et al. | |
| 2010/0040650 | A1 | 2/2010 | Crowe, Jr. et al. | |
| 2010/0092481 | A1 | 4/2010 | Lanzavecchia et al. | |
| 2010/0173980 | A1 | 7/2010 | Vaillant et al. | |
| 2010/0196492 | A1 | 8/2010 | Green et al. | |
| 2010/0285112 | A1 | 11/2010 | Novobrantseva et al. | |
| 2010/0324120 | A1 | 12/2010 | Chen et al. | |
| 2011/0020667 | A1 | 1/2011 | Deeman et al. | |
| 2011/0053893 | A1 * | 3/2011 | Wu et al. | 514/81 |
| 2011/0070260 | A1 | 3/2011 | Baric et al. | |
| 2011/0076335 | A1 | 3/2011 | Yaworski et al. | |
| 2011/0117125 | A1 | 5/2011 | Hope et al. | |
| 2011/0200582 | A1 | 8/2011 | Baryza et al. | |
| 2011/0200667 | A1 | 8/2011 | Oñate Contreras et al. | |
| 2011/0229969 | A1 | 9/2011 | Sandig et al. | |
| 2011/0244026 | A1 | 10/2011 | Guild et al. | |
| 2011/0300205 | A1 * | 12/2011 | Geall et al. | 424/450 |
| 2011/0305727 | A1 * | 12/2011 | Swanson et al. | 424/211.1 |
| 2012/0030901 | A1 | 2/2012 | Manninen et al. | |
| 2012/0100207 | A1 | 4/2012 | Motokui et al. | |
| 2012/0156251 | A1 * | 6/2012 | Brito et al. | 424/400 |
| 2012/0177701 | A1 | 7/2012 | Ilyinskii et al. | |
| 2012/0195936 | A1 | 8/2012 | Rudolph et al. | |
| 2012/0237546 | A1 * | 9/2012 | Singh et al. | 424/211.1 |
| 2012/0251618 | A1 | 10/2012 | Schrum et al. | |
| 2013/0101609 | A1 * | 4/2013 | O'Hagan et al. | 424/184.1 |
| 2013/0149375 | A1 * | 6/2013 | Geall | 424/450 |
| 2013/0164289 | A1 * | 6/2013 | McVoy et al. | 424/134.1 |
| 2013/0171185 | A1 * | 7/2013 | Settembre et al. | 424/192.1 |
| 2013/0171241 | A1 * | 7/2013 | Geall | 424/450 |
| 2013/0177639 | A1 * | 7/2013 | Geall et al. | 424/450 |
| 2013/0177640 | A1 * | 7/2013 | Geall et al. | 424/450 |
| 2013/0183355 | A1 * | 7/2013 | Jain et al. | 424/400 |
| 2013/0189351 | A1 * | 7/2013 | Geall | 424/450 |
| 2013/0195968 | A1 * | 8/2013 | Geall et al. | 424/450 |
| 2013/0195969 | A1 * | 8/2013 | Geall et al. | 424/450 |
| 2013/0202684 | A1 * | 8/2013 | Geall et al. | 424/450 |
| 2013/0225409 | A1 | 8/2013 | Allen et al. | |
| 2013/0245105 | A1 | 9/2013 | de Fougerolles et al. | |
| 2013/0295043 | A1 | 11/2013 | Kallen et al. | |
| 2014/0023673 | A1 | 1/2014 | Weiner et al. | |
| 2014/0030292 | A1 * | 1/2014 | Franti | A61P 31/22 424/229.1 |
| 2014/0044751 | A1 * | 2/2014 | Dormitzer | 424/211.1 |
| 2014/0141070 | A1 * | 5/2014 | Geall et al. | 424/450 |
| 2014/0193484 | A1 * | 7/2014 | Bertholet Girardin et al. | 424/450 |
| 2014/0212498 | A1 * | 7/2014 | Brito et al. | 424/489 |
| 2014/0220083 | A1 * | 8/2014 | Brito et al. | 424/400 |
| 2014/0227346 | A1 * | 8/2014 | Geall et al. | 424/450 |
| 2014/0242152 | A1 * | 8/2014 | Geall et al. | 424/450 |
| 2014/0248314 | A1 * | 9/2014 | Swanson et al. | 424/211.1 |
| 2014/0255472 | A1 * | 9/2014 | Geall et al. | 424/450 |
| 2014/0271829 | A1 * | 9/2014 | Lilja et al. | 424/450 |
| 2014/0275227 | A1 | 9/2014 | Hoge et al. | |
| 2014/0303232 | A1 * | 10/2014 | Baryza et al. | 514/44 A |
| 2014/0348863 | A1 * | 11/2014 | Bianchi et al. | 424/186.1 |
| 2015/0017251 | A1 * | 1/2015 | Malyala et al. | 424/501 |
| 2016/0024167 | A1 | 1/2016 | Masignani et al. | |
| 2016/0129105 | A1 | 5/2016 | Von Der Mülbe et al. | |
| 2018/0094033 | A1 | 4/2018 | Telford et al. | |
| 2019/0343862 | A1 | 11/2019 | Geall et al. | |
| 2020/0048636 | A1 | 2/2020 | Geall | |
| 2020/0069793 | A1 | 3/2020 | Ciaramella | |
| 2020/0113830 | A1 | 4/2020 | Geall et al. | |
| 2020/0113831 | A1 | 4/2020 | Geall et al. | |
| 2020/0230058 | A1 | 7/2020 | Geall et al. | |
| 2020/0323896 | A1 | 10/2020 | Geall et al. | |
| 2021/0268013 | A1 | 9/2021 | Geall et al. | |
| 2021/0290755 | A1 | 9/2021 | Geall et al. | |
| 2022/0054525 | A1 | 2/2022 | Geall et al. | |
| 2022/0056449 | A1 | 2/2022 | Geall | |
| 2022/0119455 | A1 | 4/2022 | Franti et al. | |
| 2022/0192997 | A1 | 6/2022 | Geall et al. | |
| 2022/0213149 | A1 | 7/2022 | Franti et al. | |
| 2022/0323354 | A1 | 10/2022 | Geall | |
| 2022/0331248 | A1 | 10/2022 | Geall | |
| 2022/0347079 | A1 | 11/2022 | Geall | |
| 2022/0347097 | A1 | 11/2022 | Geall | |
| 2022/0362152 | A1 | 11/2022 | Geall | |

FOREIGN PATENT DOCUMENTS

| | | | |
|---|---|---|---|
| EP | 2 578 685 | A2 | 4/2013 |
| EP | 2 590 676 | B1 | 8/2015 |
| EP | 2 590 626 | B1 | 10/2015 |
| EP | 2 591 114 | B1 | 6/2016 |
| EP | 2 510 099 | B1 | 8/2017 |
| EP | 3 336 082 | A1 | 6/2018 |
| EP | 2 750 707 | B1 | 10/2018 |
| EP | 3 318 248 | B1 | 4/2019 |
| EP | 3 492 109 | A1 | 6/2019 |
| EP | 2 591 103 | B1 | 8/2019 |
| EP | 3 611 266 | A1 | 2/2020 |
| EP | 3 682 905 | A1 | 7/2020 |
| EP | 2 729 126 | B1 | 12/2020 |
| JP | 2000/505802 | A | 5/2000 |
| JP | 2001-514857 | A | 9/2001 |
| JP | 2007-112768 | A | 5/2007 |
| JP | 2007-521247 | A | 8/2007 |

(56) References Cited

FOREIGN PATENT DOCUMENTS

| | | | | |
|---|---|---|---|---|
| JP | 2008-501729 | A | 1/2008 | |
| JP | 2009-510097 | A | 3/2009 | |
| JP | 2009-539845 | A | 11/2009 | |
| JP | 2010-25644 | A | 2/2010 | |
| JP | 2010-528591 | A | 8/2010 | |
| JP | 2011-504802 | A | 2/2011 | |
| WO | WO 89/00812 | A1 | 2/1989 | |
| WO | WO 90/11072 | A1 | 10/1990 | |
| WO | WO 92/19752 | A1 | 11/1992 | |
| WO | WO 93/24640 | A2 | 12/1993 | |
| WO | WO 95/27721 | A1 | 10/1995 | |
| WO | WO 96/08235 | A1 | 3/1996 | |
| WO | WO 96/17072 | A2 | 6/1996 | |
| WO | 97/28818 | A1 | 8/1997 | |
| WO | WO 97/30170 | A1 | 8/1997 | |
| WO | WO 98/10748 | A1 | 3/1998 | |
| WO | WO 98/51278 | A2 | 11/1998 | |
| WO | WO 99/11808 | A1 | 3/1999 | |
| WO | 99/30733 | A1 | 6/1999 | |
| WO | WO 99/52503 | A2 | 10/1999 | |
| WO | WO 00/00617 | A2 | 1/2000 | |
| WO | WO 00/03683 | A2 | 1/2000 | |
| WO | WO 01/29233 | A2 | 4/2001 | |
| WO | WO 01/79253 | A1 | 10/2001 | |
| WO | WO 01/93836 | A2 | 12/2001 | |
| WO | WO 02/02606 | A2 | 1/2002 | |
| WO | 2002/09645 | A2 | 2/2002 | |
| WO | WO 02/09645 | A2 | 2/2002 | |
| WO | WO 02/26209 | A2 | 4/2002 | |
| WO | WO 02/34771 | A2 | 5/2002 | |
| WO | WO 02/061113 | A2 | 8/2002 | |
| WO | WO 02/072027 | A2 | 9/2002 | |
| WO | WO 02/079239 | A2 | 10/2002 | |
| WO | WO 02/095023 | A2 | 11/2002 | |
| WO | WO 02/098443 | A2 | 12/2002 | |
| WO | WO 03/018054 | A1 | 3/2003 | |
| WO | WO 03/068190 | A1 | 8/2003 | |
| WO | WO 2004/076645 | A2 | 9/2004 | |
| WO | WO 2004/096509 | A2 | 11/2004 | |
| WO | WO 2005/002619 | A2 | 1/2005 | |
| WO | WO 2005/007689 | A1 | 1/2005 | |
| WO | WO 2005007689 | A1 * | 1/2005 | ........... C07K 14/045 |
| WO | WO 2005/032582 | A2 | 4/2005 | |
| WO | 2005046621 | A2 | 5/2005 | |
| WO | WO 2005/060934 | A1 | 7/2005 | |
| WO | WO 2005/111066 | A2 | 11/2005 | |
| WO | WO 2005/113781 | A2 | 12/2005 | |
| WO | WO 2005/113782 | A1 | 12/2005 | |
| WO | WO 2005/120152 | A2 | 12/2005 | |
| WO | WO 2005/121348 | A1 | 12/2005 | |
| WO | WO 2006/053646 | A2 | 5/2006 | |
| WO | 2006/061643 | A1 | 6/2006 | |
| WO | WO 2006/078294 | A2 | 7/2006 | |
| WO | WO 2006/089264 | A2 | 8/2006 | |
| WO | WO 2006/091517 | A2 | 8/2006 | |
| WO | WO 2006/092607 | A1 | 9/2006 | |
| WO | WO 2006/094756 | A2 | 9/2006 | |
| WO | WO 2006/110413 | A2 | 10/2006 | |
| WO | WO 2006/138004 | A2 | 12/2006 | |
| WO | WO 2007/014754 | A1 | 2/2007 | |
| WO | WO 2007/024708 | A3 | 3/2007 | |
| WO | WO 2007/036366 | A2 | 4/2007 | |
| WO | WO 2007/041270 | A1 | 4/2007 | |
| WO | WO 2007/047749 | A1 | 4/2007 | |
| WO | WO 2007/049155 | A2 | 5/2007 | |
| WO | WO 2007/107304 | A2 | 9/2007 | |
| WO | WO 2007/146024 | A2 | 12/2007 | |
| WO | WO 2007/149518 | A2 | 12/2007 | |
| WO | WO 2008/020330 | A2 | 2/2008 | |
| WO | 2008033966 | A2 | 3/2008 | |
| WO | WO 2008/051245 | A2 | 5/2008 | |
| WO | WO 2008/083949 | A2 | 7/2008 | |
| WO | WO 2008/103276 | A2 | 8/2008 | |
| WO | WO 2008103276 | A2 * | 8/2008 | ............. C12N 15/88 |
| WO | WO 2008/137758 | A2 | 11/2008 | |
| WO | WO 2008/148068 | A1 | 12/2008 | |
| WO | WO 2008/155141 | A2 | 12/2008 | |
| WO | WO 2009/003975 | A1 | 1/2009 | |
| WO | WO 2009/016515 | A2 | 2/2009 | |
| WO | WO 2009/026328 | A2 | 2/2009 | |
| WO | WO 2009/031043 | A2 | 3/2009 | |
| WO | 2009/042794 | A2 | 4/2009 | |
| WO | WO 2009/040443 | A1 | 4/2009 | |
| WO | WO 2009/042794 | A2 | 4/2009 | |
| WO | 2009/074861 | A2 | 6/2009 | |
| WO | WO 2009/068485 | A1 | 6/2009 | |
| WO | WO 2009/079185 | A2 | 6/2009 | |
| WO | WO 2009/086558 | A1 | 7/2009 | |
| WO | WO 2009-104092 | A2 | 8/2009 | |
| WO | WO 2009/109860 | A2 | 9/2009 | |
| WO | WO 2009/111088 | A2 | 9/2009 | |
| WO | WO 2009/127230 | A1 | 10/2009 | |
| WO | WO 2009/132131 | A1 | 10/2009 | |
| WO | WO 2009/132206 | A1 | 10/2009 | |
| WO | 2009/156852 | A1 | 12/2009 | |
| WO | WO 2009/146867 | A1 | 12/2009 | |
| WO | WO 2010/007463 | A1 | 1/2010 | |
| WO | WO 2010/007533 | A2 | 1/2010 | |
| WO | WO 2010/015098 | A1 | 2/2010 | |
| WO | WO 2010/019718 | A2 | 2/2010 | |
| WO | 2010/036948 | A2 | 4/2010 | |
| WO | WO 2010/042877 | A1 | 4/2010 | |
| WO | WO 2010/053572 | A2 | 5/2010 | |
| WO | WO 2010/054401 | A1 | 5/2010 | |
| WO | WO 2010/059689 | A2 | 5/2010 | |
| WO | WO 2010/088537 | A2 | 8/2010 | |
| WO | WO 2010/119343 | A2 | 10/2010 | |
| WO | WO 2010/144740 | A1 | 12/2010 | |
| WO | 2011/005799 | A2 | 1/2011 | |
| WO | WO 2011/001780 | A1 | 1/2011 | |
| WO | WO 2011/005799 | A2 | 1/2011 | |
| WO | WO 2011/008974 | A2 | 1/2011 | |
| WO | WO 2011/012316 | A2 | 2/2011 | |
| WO | WO 2011/068810 | A1 | 6/2011 | |
| WO | WO 2011/071860 | A2 | 6/2011 | |
| WO | WO 2011/071931 | A2 | 6/2011 | |
| WO | WO 2011/075656 | A1 | 6/2011 | |
| WO | WO 2011/076807 | A2 | 6/2011 | |
| WO | WO 2011/112717 | A1 | 9/2011 | |
| WO | 2011/127316 | A1 | 10/2011 | |
| WO | WO 2011/140627 | A1 | 11/2011 | |
| WO | WO 2012/006369 | A2 | 1/2012 | |
| WO | WO 2012/006372 | A1 | 1/2012 | |
| WO | WO 2012/006376 | A2 | 1/2012 | |
| WO | WO 2012/006377 | A2 | 1/2012 | |
| WO | WO 2012/006378 | A1 | 1/2012 | |
| WO | WO 2012/006380 | A2 | 1/2012 | |
| WO | WO 2012/019168 | A2 | 2/2012 | |
| WO | 2012/030901 | A1 | 3/2012 | |
| WO | WO 2012/030901 | A1 | 3/2012 | |
| WO | WO 2012/031043 | A1 | 3/2012 | |
| WO | WO 2012/031046 | A2 | 3/2012 | |
| WO | WO 2012/034025 | A2 | 3/2012 | |
| WO | WO 2012/045075 | A1 | 4/2012 | |
| WO | WO 2012/045082 | A2 | 4/2012 | |
| WO | WO 2012/092569 | A2 | 7/2012 | |
| WO | WO 2012/135805 | A2 | 10/2012 | |
| WO | WO 2012/158736 | A1 | 11/2012 | |
| WO | WO 2012/170889 | A2 | 12/2012 | |
| WO | WO 2012/170930 | A1 | 12/2012 | |
| WO | WO 2013/006825 | A1 | 1/2013 | |
| WO | WO 2013/006837 | A1 | 1/2013 | |
| WO | WO 2013/033563 | A1 | 3/2013 | |
| WO | WO 2013/039861 | A2 | 3/2013 | |
| WO | WO 2013/052523 | A1 | 4/2013 | |
| WO | WO 2013/090648 | A1 | 6/2013 | |
| WO | WO 2013/096709 | A2 | 6/2013 | |
| WO | WO 2013/130161 | A1 | 9/2013 | |
| WO | WO 2013/151663 | A1 | 10/2013 | |
| WO | WO 2013/151664 | A1 | 10/2013 | |
| WO | WO 2013/151665 | A2 | 10/2013 | |
| WO | WO 2013/151666 | A2 | 10/2013 | |
| WO | WO 2013/151667 | A1 | 10/2013 | |
| WO | WO 2013/151668 | A2 | 10/2013 | |

(56) References Cited

FOREIGN PATENT DOCUMENTS

| | | | |
|---|---|---|---|
| WO | WO 2013/151669 | A1 | 10/2013 |
| WO | WO 2013/151670 | A2 | 10/2013 |
| WO | WO 2013/151671 | A1 | 10/2013 |
| WO | WO 2013/151672 | A2 | 10/2013 |
| WO | WO 2013/151736 | A2 | 10/2013 |
| WO | WO 2014/081507 | A1 | 5/2014 |
| WO | WO 2014/152211 | A1 | 9/2014 |
| WO | WO 2014/160243 | A1 | 10/2014 |
| WO | WO 2017/049245 | A2 | 3/2017 |
| WO | WO 2017/075531 | A1 | 5/2017 |
| WO | WO 2018/089790 | A1 | 5/2018 |
| WO | WO 2020/106946 | A1 | 5/2020 |
| WO | WO 2021/038508 | A1 | 3/2021 |
| WO | WO 2 791 160 | B1 | 3/2022 |
| WO | WO 2022/137133 | A1 | 6/2022 |

OTHER PUBLICATIONS

Shade RO, Blundell MC, Cotmore SF, Tattersall P, Astell CR. unknown protein [Human parvovirus B19]. GenBank: AAA66867. 1, Dep. May 17, 1995.*

Harvey et al., Kunjin Virus Replicon Vectors for Human Immunodeficiency Virus Vaccine Development, 2003, Journal of Virology, vol. 77, No. 14, pp. 7796-7803.*

Lee et al., Venezuelan equine encephalitis virus-vectored vaccines protect mice against anthrax spore challenge, 2003, Infection and Immunity, vol. 71, No. 3, pp. 1491-1496.*

Bernstein et al., "Randomized, double-blind, Phase 1 trial of an alphavirus replicon vaccine for cytomegalovirus in CMV seronegative adult volunteers," Vaccine, 28:484-493 (2010).

Xu et al., "Characterization of immune Responses Elicited in Macaques Immunized Sequentially with Chimeric VEE/SIN Alphavirus Replicon Particles Expressing SIVGag and/or HIVEnv and with Recombinant HIVgp140Env Protein," Aids Research and Human Retroviruses, Mary Ann Liebert, 22(10):1022-1030 (2006).

Barnett et al., "Antibody-Mediated Protection against Mucosal Simian-Human Immunodeficiency Virus Challenge of Macaques Immunized with Alphavirus Replicon Particles and Boosted with Trimeric Envelope Glycoprotein in MF59 Adjuvant," Journal of Virology, 84(12):5975-5985 (2010).

Mok et al., "Venezuelan equine encephalitis virus replicon particles encoding respiratory syncytial virus surface glycoproteins induce protective mucosal responses in mice and cotton rats," Journal of Virology, The American Society for Microbiology, 81(24):13710-13722 (2007).

Anderson et al. "Incorporation of pseudouridine into mRNA enhances translation by diminishing PKR activation," Nucleic Acids Research, 38(17):5884-5892 (2010).

Defang et al., "Induction of neutralizing antibodies to Hendra and Nipah glycoproteins using a Venezuelan equine encephalitis virus in vivo expression system," Vaccine Elsevier Ltd. GB, 29(2):212-220 (2010).

Genini et al., "Serum antibody response to the gH/gL/pUL128-131 five protein complex of Serum antibody response to the gH/gL/pUL128-131 five-protein complex of human cytomegalovirus (HCMV) in primary and reactivated HCMV infections," Journal of Clinical Virology, 52:113-118 (2011).

Graham, Barney, "Biological challenges and technological opportunities for respiratory syncytial virus vaccine development," Immunological Reviews, 239(1):149-166 (2011).

Hidmark et al.,"Humoral Responses against Coimmunized Protein Antigen but Not against Alphavirus-Encoded Antigens Require Alpha/Beta Interferon Signaling," Journal of Virology, 80(14):7100-7110 (2006).

Nä Slund et al., "Role of innate signailing pathways in the immunogenicity of alphaviral replicon-based vaccines," Virology Journal, 8(1):36 (2011).

Van Bleek et al., "RSV 2010: Recent advances in research on respiratory syncytial virus and other pneumoviruses," Vaccine, 29(43):7285-7291 (2011).

Carine et al., "Vaccination of calves using the BRSV nucleocapsid protein in a DNA prime-protein boost strategy stimulates cell-mediated immunity and protects the lungs against BRSV replication and pathology," Vaccine Elsevier Ltd, GB, 26(37):4840-4848 (2008).

Saccoccio, Frances Maria, "Thesis: CMV Vaccine Development based on Epithelial Entry Mediators UL128, UL130, and UL131," Jun. 3, 2011, Retrieved from the Internet: URL:https//digarchive.library.vcu.edu/bitstreamjhandle/10156/3452/SACCOCCIO FRANCES PhD.pdf?sequence=1-1 retrieved on Mar. 18, 2014] Impact on future vaccine design; p. 160 (2011). Chapter: Peptides to UL130 and UL131. Neutralize CMV Infection of Mucosal Epithelial Cells; p. 96.

Elliott et al., "Alphavirus replicon particles encoding the fusion or attachment glycoproteins of respiratory syncytial virus elicit protective immune responses in BALB/c mice and functional serum antibodies in rhesus macaques," Vaccine Elsevier Ltd, GB, 25(41):7132-7144, (2007).

Thompson et al., "Mucosal and systemic adjuvant activity of alphavirus replicon particles," Proceedings of the National Academy of Sciences, 103(10):3722-3727 (2006).

Reap et al., Development and preclinical evaluation of an alphavirus replicon particle vaccine for cytomegalovirus, Vaccine, Elsevier Ltd, GB, 25(42):7441-7449, (2007).

International Search Report for International Application No. PCT/US2012/045847 dated Oct. 10, 2012.

Fleeton, M.N. et al., "Self-replicative RNA vaccines elicit protection against influenza A virus, respiratory syncytial virus, and a tickborne encephalitis virus", Journal of Infectious Diseases, University of Chicago Press, Chicago, IL, vol. 183, No. 9, pp. 1395-1398, 2001.

Lee, et al. "Multiagent vaccines vectored by Venezuelan equine encephalitis virus replicon elicits immune responses to Marburg virus and protection against anthrax and botulinum neurotoxin in mice." Vaccine; 2006; pp. 6886-6892; vol. 24.

Lobue, et al. "Multivalent norovirus vaccines induce strong mucosal and systemic blocking antibodies against multiple strains." Vaccine; 2006; pp. 5220-5234; vol. 24.

Phumiamorn, et al., "Induction of humoral and cell-mediated immunity to hepatitis B surface antigen by a novel adjuvant activity of Oka varicella vaccine." Journal of General Virology; 2003; pp. 287-291; vol. 84.

Vajdy, et al., "Mucosal adjuvants and delivery systems for protein-, DNA- and RNA-based vaccines." Immunology and Cell Biology; 2004; pp. 617-627; vol. 82.

Strauss, J. H. et al., Microbiological Reviews, 58(3): 491-562 (1994) (excerpt).

Pushko, P. et al., Virology, 239: 389-401(1997).

Stedman's Medical Dictionary; 27th Edition; Lippincott, Williams & Wlkins; published.

Tonkin, D. R. et al., Vaccine, 28(18): 3238-3246 (2010).

Glaxosmithkline, SAM/Protein Mixed Modality Study Data, PowerPoint presentation (2019).

"Imagines• Immunization" Merriam Webster's Medical Desk Dictionary; 1993; pp. 326-327.

"Mengovirus", Wikipedia, (Apr. 29, 2020), pp. 1-2, URL:https://en.wikipedia.org/wiki/Mengovirus (Anonymous).

"Pschyrembel, Klinisches Wortenbuch" Immunisiserung, Immunreaktion; 1997; pp. 747-748.

Aberle, "Humerai and Cellular Immune Response to RNA Immunization with Flavivirus Replicons Derived from Tick-Borne Encephalitis Virus", Journal of Virology; 2005; pp. 15107-15113; vol. 79(24).

Acheampong, Samuel et al.; "Ionization and transfection activity of n-methyl-substituted carbamoyl-cholesterol derivatives", Journal of Biophysical Chemistry, vol. 2, No. 2, 53-62; 2011.

Atwood, J.L., (ed.), "Comprehensive Supramolecular Chemistry II" Oxford: Elsevier, vol. 1:Gen. Prin. of SupraMol. Chem. and Mol. Recogn.; pp. 141 (2017).

(56) References Cited

OTHER PUBLICATIONS

Auxiliary requests 1, 2, and 3 (claims 1-13) filed in relation to the Opposition of European Patent No. 2590676B1 (Application No. 11741348.4) 6 pages.
Babiuk, S., et al., "Electroporation improves the efficacy of DNA vaccines in large animals," Vaccine: 2002, pp. 3399-3406; vol. 20(27-28).
Bagarzzi, M. L., et al., "Immunotherapy against HPV 16/18 generates potent TH1 and cytotoxic cellular immune responses," Science Translational Medicine; 2012; vol. 4(155), pp. 1-14.
Bailey et al., "Modulation of membrane fusion by asymmetric transbilayer distributions of amino lipids", Biochemistry, 33:12573-80 (1994).
Barai, V.N. et al., "Isolation of Highly Purified Yeast RNA by Ca2+ Precipitation," Applied Biochemistry and Microbiology, 1995: 31(5): 421-424.
Birdi, K.S., (Ed.), Handbook of Surface and Colloidal Chemistry, CRC Press., Boca Raton, pp. 119-156.
BMGF Report, "Summary of stability data for licensed vaccines," Working in Tandem Ltd, 2012, pp. 1-17.
Bogers, et al., "Macaques Primed with Self-Amplifying RNA Vaccines Expressing HIV-1 Envelope and Boosted with Recombinant Protein Show Potent T-and-B-Cell Responses" poster at the AIDS Vaccine 2012 meeting; Sep. 9-12, 2012; Boston, MA USA, p. 107.
Bogers, et al., "Potent Immune Responses in Rhesus Macaques Induced by Nonviral Delivery of a Self-amplifying RNA Vaccines Expressing HIV Type 1 Envelope With a Cationic Nanoemulsion," J. Infectious Disease; vol. 211; 2015; pp. 947-955.
Boxus, M., et al., "DNA immunization with plasmids encoding fusion and nucleocapsid proteins of bovine respiratory syncytial virus induces a strong cell-mediated immunity and protects calves against challenge," Journal of Virology; 2007; pp. 6879-6689; vol. 81(13).
Bramwell, "The rational design of vaccines," (DDT.2005; 10(22): 1527-1534).
Bringmann et al., "RNA Vaccines in Cancer Treatment," Journal of Biomedicine and Biotechnology, 2010:1-12 (2010).
Brito et al., "Self-Amplifying mRNA Vaccines", Advances in Genetics, vol. 89; pp. 179-233; 2015.
Brito, et al., "A Cationic Nanoemulsion for the Delivery of Next-generation RNA Vaccines," Mol. Ther., 2014; pp. 2118-2129; vol. 22.
Broz, et al., "Newly described pattern recognition receptors team up against intracellular pathogents," Nat. Rev. Immunol. 13:8: 551-565 (2013).
Buyens et al., "Elucidating the encapsulation of short interfering RNA in PEGylated cationic liposomes", Langmuir, 25(9):4886-4891 (2009).
Buza, J. et al., "CD14+ cells are required for IL-12 response in bovine blood mononuclear cells activated with Toll-like receptor (TLR) 7 and TLR8 ligands", Vet. Immunol. Immunopath 126(3-4): 273-282 (2008).
Cannon, G., et al., "RNA Based Vaccines", DNA Cell Biol., 21(12): 953-961 (2002).
Caplen, N.J., "Nucleic acid transfer using cationic lipids", Methods In Mole. Biol., 133:1-19 (2000).
Carralot, J.P., et al., "Polarization of Immunity induced by direct injection of naked sequence-stabilized mRNA vaccines", Cell. Mole. Life Sci. 61(18):2418-2424 (2004).
U.S. Appl. No. 61/233,347, filed Jul. 6, 2009.
U.S. Appl. No. 61/265,653, filed Dec. 1, 2009.
U.S. Appl. No. 61/361,780, filed Jul. 6, 2010.
U.S. Appl. No. 61/361,794, filed Jul. 6, 2010.
Chambers, et al., "Vaccination of mice and cattle with plasmid DNA encoding the *Mycobacterium bovis* antigent MPB83," Clinical Infection Diseases; 2000; pp. S283-S287; vol. 30(3).
Cheng et al., "Enhancement of Sindbis virus self-replicating RNA vaccine potency by linkage of *Mycobacterium tuberculosis* heat shock protein 70 gene to an antigen gene", Journal of Immunology, 166:6218-6226 (2001).
Cheng, W.F., et al, "Enhancement of Sindbis Virus Self-Replicating RNA Vaccine Potency by Linkage of Herpes Simplex Virus Type 1 VP22 Protein to Antigen", J. Viral 75(5): 2368-2376 (2001).
Chiaramoni et al., "Liposome/DNA systems: correlation between hydrophobicity and DNA conformational change," J Biol Phys (2008) 34:179-188.
Chrai, et al, "Liposomes: A Review Part I: Manufacturing Issues," Apr. 2002, Biotech Trends, Pharmaceutical Technology, pp. 28-34.
Communication of the Board of Appeals pursuant to Art. 15(1) of the Rules of Procedure of the Boards of Appeal issued on Mar. 25, 2021 in European Patent Application Publication No. 2590676.
Conry, et al., "Characterization of a Messenger RNA Polynucleotide Vaccine Vector," Cancer Research, 1995: pp. 1397-1400; vol. 55.
Cox, et al., "Bovine herpesvirus 1: immune responses in mice and cattle injected with plasmid DNA," Journal of Virology; 1993; pp. 5664-5567; vol. 67(9).
Crooke Stanley T., (Ed.), "Antisense Drug Technology: Principles, Strategies, and Applications," 2nd ed., chapter 9 (2008), ages 237-270.
Cui, et al., "DNA Vaccine," Advanced in Genetics; 2005; pp. 257-289; vol. 54.
Cullis, Pieter et al.; U.S. Appl. No. 61/280,510, filed Nov. 4, 2009 (certified Priority Document from WO2011140627).
Cvagna, et al.; "7—Signs and Work of Man"; The National Park of the Casentine Forests; 2003; pp. 175.
Davis, et al., "DNA vaccine for hepatitis B: Evidence for immunogenicity in chimpanzees and comparison with other vaccines," Proc. Natl Acad Sci USA; 1996; pp. 7213-7218; vol. 93.
Declaration Andrew Geall dated Sep. 11, 2014.
Declaration by Prof. Peter Liljeström, dated Mar. 31, 2019 submitted in EP 2591114.
Declaration by Prof. Peter Liljeström, dated Aug. 7, 2018 submitted in EP 2591114.
Declaration of Professor Liljeström dated Dec. 11, 2018 submitted in EP2590676.
Deering, et al., "Nucleic acid vaccines: prospects for non-viral delivery of mRNA vaccines," Expert Opinion Drug Delivery; 2014; pp. 885-899; vol. 11(6).
Diebold, S.S., et al., "Innate Antiviral Responses by Means of TLR7-Mediated Recognition of Single-Stranded RNA", Science 303(5663): 1529-1531 (2004).
Dupuis et al., "Dendritic cells internalize vaccine adjuvant after intramuscular injection", Cellular Immunology, 186:18-27 (1998).
Dupuis et al., "Distribution of DNA vaccines determines their immunogenicity after intramuscular injection in mice," Journal of Immunology, 165:2850-2858 (2000).
El Ouahabi, A. et al., "Double long-chain amidine liposome-mediated self replicating RNA transfection", FEBS Letters, 380(1-2): 108-112 (1996).
Elbashir et al., "Duplexes of 21-nucleotide RNAs mediate RNA interference in cultured mammalian cells." Nature, 2001, 411(6836), 494-498.
Encyclopedia Britannica, House Mouse; 2005, p. 963.
Espuelas, Socorro, et al., "Effect of synthetic lipopeptides formulated in liposomes on the maturation of human dendritic cells," Molecular Immunology 42 (2005):721-729, and Corrigendum, Molecular Immunology 43 (2006) 772.
Evers, M., et al, "State-of-the-Art Design and Rapid-Mixing Production Techniques of Lipid Nanoparticles for Nucleic Acid Delivery", Small Methods, 2:1-20, (2018).
Zuckerman, "Principles and Practice of Travel Medicine," 2001, pp. 165-183.
Felgner, et al., "Lipofection: A Highly Efficient, Lipid-Mediated DNA-Transfection Procedure." Proc. Natl. Acad. Sci. USA: 1987, pp. 7413-7417; vol. 84.
Fenske, "Lipsomal Nanomedicines: An Emerging Field", Toxicologic Pathology; 2008; pp. 21-29; vol. 36, No. 1.
Final Decision and Upheld Claims from EP2591114 dated Nov. 12, 2018 (European Equivalent of U.S. Appl. No. 13/808,153).

(56) References Cited

OTHER PUBLICATIONS

Fleeton et al., "Self-Replicative RNA Vaccines Elicit Protection against Influenza A Virus, Respiratory Syncytial Virus, and a Tickborne Encephalitis Virus", Journal of Infectious Diseases 183:1395-1398 (2001).
Fraenkel-Conrat et al., (Ed.), Virology second edition, Prentice-Hall Inc., Englewood Cliffs, New Jersey; 1988; from Chapter 3, "Enveloped Plus-strand RNA Viruses:Togaviridae", pp. 96-103.
Freddolino, et al, "Molecular Dynamics Simulations of the Complete Satellite Tobacco Mosaic Virus." Structure; 2006; pp. 437-449: vol. 14.
Fynan, E.F., et al., "DNA vaccines: Proctective immunizations by parenteral, mucosal, and gene-gun inoculations," Proc Natl Acad Sci.: 1993; pp. 11478-11482; vol. 90.
Gamvrellis, A. et al. "Vaccines that facilitate antigen entry into dendritic cells." Immunol Cell Biol. Oct. 2004; 82(5): 506-516.
Geall, A. et al, "Nonviral delivey of self-amplifying RNA vaccines." Proceedings of the National Academy of Sciences of the United States of America, 2012, 109(36), 14604-14609.
Geall, et al, "Using self-amplifying mRNA vaccines to facilitate a rapid response to pandemic influenza" Eur. Pharma. Review 19:3 20-23 (2014).
Geisbert, et al., "Postexposure Protection of Guinea Pigs against a Lethal Ebola Virus Challenge Is Conferred by RNA Interference", Journal of Infectious Diseases; 2006; pp. 1650-1657; vol. 193.
Giuliani et al., "A universal vaccine for serogroup B meningococcus," Proc. Natl. Acad. Sci. U. S. A., 2006, vol. 103, No. 29, pp. 10834-10839.
Goncalves, et al, "The effect of liposome size on the final lipid/DNA ratio of cationic lipoplexes," Biophysical Journal, 2004, 86(3), 1554-1563.
Graham, et al., "Priming Immunization Determines T Helper Cytokine mRNA Expression Patterns in Lungs of Mice Challenged with Respiratory Syncytial Virus," The Journal of Immunology; Aug. 15, 1993; pp. 2032-2040; vol. 151, No. 4.
Granstein, et al., "Induction of Anti-Tumor Immunity with Epidermal Cells Pulsed with Tumor-Derived RNA or Intradermal Administration of RNA," Journal of Investigative Dermatology; 2000: pp. 632-636; vol. 114(4).
Greer, C, et al., "A chimeric alphavirus RNA replicon gene-based vaccine for human parainfluenza virus type 3 induces protective immunity against intranasal virus challenge", Vaccine 25(3): 481-489 (2007).
Hamm et al., "Immunostimulatory RNA is a potent inducer of antigen-specific cytotoxic and humoral immune response in vivo," International Immunology, 2007, vol. 19(3): 297-304.
Heidel, J.D., et al., "Administration in non-human primates of escalating intravenous doses of targeted nanoparticles containing ribonucleotide reductase subunit M2 siRNA," Proc. Natl Acad Sci USA; 2007; pp. 5715-5721; vol. 104(14).
Herweijer et al., "Self-amplifying vectors for gene delivery," Advanced Drug Delivery Reviews, 27; 1997; pp. 5-16.
Heyes et al., "Cationic lipid saturation influences intracellular delivery of encapsulated nucleic acids," J Control Release; vol. 107; 2005; pp. 276-287.
Hoerr et al. "In vivo application of RNA leads to induction of specific cytotoxic T lymphocytes and antibodies," Eur. J. Immunol. 30; pp. 1-7; 2000.
Hope, et al., "Chapter 8; Reduction of Liposome Size and Preparation of unilamellar Vesicles by Extrusion Techniques," Liposome Technology; 1993; pp. 123-139; vol. 1.
Hornung, et al., "5'-Triphosphate RNA is the Ligand for RIG-1" Science; 2006; vol. 314; pp. 994-997.
Huang, et al., "Immunization with a bovine herpesvirus 1 glycoprotein B DNA vaccine induces cytotoxic T-lymphocyte responses in mice and cattle," Journal of General Virology; 2005; pp. 887-898; vol. 86(4).
Iavarone et al., "A Point Mutation in the Amino Terminus of TLR7 Abolishes Signaling without Affecting Ligand Binding", J Immunol, (2011), vol. 186, pp. 4213-4222.
Jeffs et al., "A scalable, extrusion-free method for efficient liposomal encapsulation of plasmid DNA", Pharmaceutical Research, (2005), vol. 22, No. 3, pp. 362-372.
Johanning et al., "A Sindbis virus mRNA polynucleotide vector achieves prolonged and high level heterologous gene expression in vivo," Nucleic Acids Res, (1995), vol. 23, pp. 1495-1501.
Johnson, T. et al., "TLR9 agonist, but not TLR7/8, functions as an adjuvant to diminish FI-RSV vaccine-enhanced disease, while either agonist used as therapy during primary RSV infection increases disease severity", Vaccine 27(23): 3045-3052 (2009).
Jones et al. "DNA vaccination protects against an influenza challenge in a double-blind randomised placebo-controlled phase 1b clinical trial" Vaccine 27 (2009): 2506-2512.
Kariko et al., "mRNA is an Endogenous Ligand for Toll-like Receptor 3"; The Journal of Biological Chemistry; 2004; vol. 279, No. 13; pp. 12542-12550.
Khan, K. H., "DNA vaccines: roles against diseases," Germs; 2013; pp. 26-35; vol. 3(1).
Kirman, et al., "Enhanced Immunogenicity to *Mycobacterium tuberculosis* by Vaccination with an Alphavirus Plasmid Replicon Expressing Antigen 85A" Infection and Immunity; 2003; pp. 575-579; vol. 71(1).
Kita, H., et al. "Replication of Genetic Information with Self-Encoded Replicase in Liposomes," Chembiochem 9 (15): 2403-2410 (2008).
Knipe, et al., "Fields Virology," 4th edition, Lippincott Williams & Wilkins, 2001: pp. 690-692; vol. 1, p. 2.
Kofler, et al. "Mimicking live flavivirus immunization with a noninfectious RNA vaccine," Proc. Natl. Acad. Sci. USA; 2004; pp. 1951-1956; vol. 101(7).
Kornbluth at al. "Immunostimulatory combinations: designing the next generation of vaccine adjuvants," Journal of Leukocyte Biology, 2006, vol. 80, pp. 1084-1102.
Kulkarni, et al. "Factors affecting microencapsulation of drugs in liposomes." Journal of Microencapsulation, 1995, 12 (3), 229-246.
Kumar et al., "Toll-like receptors and innate immunity," Biochemical and Biophysical Research Communications, 388:621-625 (2009).
Kutzler, et al., "DNA vaccines; ready for prime time?" Nature Reviews; Genetics; 2008; pp. 776-788; vol. 9(10).
Lazzaro et al., "CD8 T-cell priming upon mRNA vaccination is restricted to bone-marrow-derived antigen-presenting cells and may involve antigen transfer from myocytes," Immunology, 146:312-326 (2015).
Lee, et al., "Venezuelan Equine Encephalitis Virus-Vectored Vaccines Protect Mice Against Anthrax Spore Challenge," Infection and Immunity; 2003; pp. 1491-1496; vol. 71.
Leitner, et al., "DNA and RNA-based vaccines: principles, progress and prospects", Vaccine, 18:765-777, 1999.
Levine, M., et al., "Vaccine development strategies for improving immunization: the role of modern immunology", Nature Immunol., 5(5): 460-464 (2004).
Levy; "Quantifation of supercoiled circular content in plasmid DNA solutions using a fluorescence-based method", Nucleic Acids Res.; 2000; 28:e57, pp. 1-7.
Liljeström Curriculum Vitae/Peter Liljeström.
Liljeström Publications/Peter Liljeström.
Liljeström, et al., "A new generation of animal cell expression vectors based on the Semliki Forest virus replicon," Biotechnology, 9:1356-1361 (1991).
Liljeström, et. al., "In vitro mutagenesis of a full-lenth cDNA clone of Semliki Forest virus: the small 6,000-molecular-weight membrane protein modulates virus release," Journal of Virology, Aug. 1991; 65(8): 4107-4113.
Ljungberg et al., "Increased Immunogenicity of a DNA-Launched Venezuelan Equine Encephalitis Virus-Based Replicon DNA Vaccine," Journal of Virology, Dec. 2007, pp. 13412-13423.
Lonez, C. et al., "Cationic liposomes lipids: From gene carriers to cell signaling", Progress in Lipid Research, 47 (5):340-347 (2008).
Lorenzi, et al. "Intranasal vaccination with messenger RNA as a new approach in gene therapy: use against uberculosis," BMC Biotechnology 10 (2010): 1-11.

(56) References Cited

OTHER PUBLICATIONS

Lu, et al., "Optimization of methods to achieve mRNA-mediated transfection of tumor cells in vitro and in vivo employing cationic liposome vectors," Cancer Gene Ther., 1(4):245-252 (1994) (abstract).
Lundstrom et al., "Biology and application of alphaviruses in gene therapy", Gene Therapy: vol. 12; Suppl 1: pp. S92-S97, 2005.
Lyubchenko, et al., "Visualization of supercoiled DNA with atomic force microscopy in situ" Proc. Natl. Acad Sci. USA; 1997; pp. 496-501; vol. 94.
Malone et al., "Cationic liposome-mediated RNA transfection", Proc. Natl. Acad. Sci. (PNAS) USA: Biochemistry; 86:16:6077-6081; 1989.
Manning, et al., "Infectivity of Liposomally Encapsulated Nucleic Acids Isolated From EMC Virus and Scaple-Infected Mouse Brain", Intervirology; vol. 20; 1983; pp. 164-168.
Martin, et al., "Characterization of formaldehyde-inactivated poliovirus preparations made from live-attenuated strains," Journal of General Virology; 2003; pp. 1781-1788; vol. 84.
Martinon et al. "Induction of virus-specific cytotoxic T lymphocytes in vivo by liposome-entrapped mRNA.," Eur. J. Immuno. 1993.23: 1719-1722.
Maurer, et al., "Spontaneous Entrapment of Polynucleotides upon Electrostatic Interaction with Ethanol-Destablilized Cationic Liposomes," Biophysical Journal; vol. 80; 2001: pp. 2310-2326.
McGlone, et al., "Pig Production: Biological Principles and Applications" Chapter 8; 2000; pp. 88-109.
Merriam-Webster definition of "virion" (downloaded Mar. 14, 2016).
Mockey, M., et al. "mRNA-based cancer vaccine; prevention of B16 melanoma progression and metastasis by systemic injection of MART1 mRNA histidylated lipopolyplexes," Cancer Gene Therapy 14(9): 802-814 (2007).
Morris-Downes, et al., "A recombinant Semliki Forest virus particle vaccine encoding the prME and NS1 proteins of louping ill virus is effective in a sheep challenge model." Vaccine; 2001; pp. 3877-3884; vol. 19.
Mosca et al., "Molecular and cellular signatures of human vaccine adjuvants," Proc. Natl. Acad. Sci. USA, 105:10501-10506 (2008).
Mossman, "Protection against Lethal Simian Immunodeficiency Virus SIVsmmPBj14 Disease by a Recombinant Semliki Forest Virus gp160 Vaccine and by a gp120 Subunit Vaccine." J. Virology, 1996; pp. 1953-1960; vol. 70.
NCBI reference sequence. "*Homo sapiens* coagulation factor VIII (FB), transcript variant 1, mRNA." Mar. 2016, pp. 1-18.
Notice of Opposition in relation to European Patent No 2591103B1 (Appln No. 11736498.4) dated May 28, 2020 (44 pages).
Obata, "Evaluation of pH-responsive liposomes containing amino acid-based zwitterionic lipids for improving intracellular drug delivery in vitro and in vivo", Journal of Controlled Release; 2010; pp. 267-276; vol. 142, No. 2.
O'Hagan et al., "Induction of potent immune responses by cationic microparticles with adsorbed human innunodeficiency virus DNA vaccines,"J Virology, (2001), vol. 75, pp. 9037-9043.
Opponents arguments by Dr. Georg Schnappauf filed on Jan. 14, 2022 in opposition to European Patent No. 2591103.
Opponents arguments by Janssen Vaccines & Prevention B.V. filed on Jan. 14, 2022 in opposition to European Patent No. 2591103.
Opposition Document D60—Declaration of Russell N. Johnson from EP2591114. European Equivalent of U.S. Appl. No. 13/808,153, filed Aug. 8, 2018.
Organism overview of Encephalomyocarditis virus and of Poliovirus obtained from PubMed "Encephalomyocarditis virus." retrieved on Jun. 4, 2019 from https://www.ncbi.nim.min.gov/genome/?term=encephalomyocarditis+virus, and "Enterovirus C" retrieved on Jun. 4, 2019 from https://www.ncbi nlm nih gov/genome/?term=poliovirus[orgn].
Ott, et al., "A Cationic sub-micron emulsion [M59/DOTAP] is an effective delivery system for DNA vaccines," Journal of Controlled Release; 2002; pp. 1-5; vol. 79(1-3).
Papahadjopoulos, et al., "Cochleate Lipid Cylinders: Formation by Fusion of Unilamellar Lipid Vesicles" Biochim et Biophys Acta; 1975; pp. 483-491; vol. 394.
Papahadjopoulos, et al., "Incorporation of Macromolecules within Large Unilamellar Vesicles (LUV)" Annals NY Academy of Sciences; 1978; pp. 259-267.
Patentee's Reply to Opposition in relation to European Patent No. 2591103B1 (EP Appln No. 11736498.4) dated Oct. 23, 2020 (28 pages).
Perri et al., "An alphavirus replicon particle chimera derived from venezuelan equine encephalitis and sindbis viruses is a potent gene-based vaccine delivery vector," J Virol. (2003), vol. 77, pp. 10394-10403.
Preliminary Opposition Opinion from EP2591114 (EP Appl. 11736497.6), European Equivalent of U.S. Appl. No. 13/808,153, dated Feb. 23, 2018.
Ramana, et al., "Development of a liposomal nanodelivery system for nevirapine." Journal of Biomedical Science, 2010, 17:57, pp. 1-9.
Rayner, et al., "Alphavirus vectors and vaccination", Reviews in Medical Virology; 2002; pp. 279-296; vol. 12.
Ren et al., "Immunogene therapy of recurrent glioblastoma multiforme with a lipsomally encapsulated replication-incompetent Semliki forest virus vector carrying the human interleukin-12 gene—a phase I/II clinical protocol", J. Neuro-Oncology, 2003, 64:147-154.
Rodriguez-Gascon, et al., "Development of nucleic acid vaccines: use of self-amplifying RNA in lipid nanoparticles," International Journal of Nanomedicine, 2014, vol. 9(1), 1833-1843.
Sacco, et al,"The Average Body Surface Area of Adult Cancer Patients in the UK: A Multicentre Retrospective Study." PLoS One; 2010; pp. 1-6; vol. 5(1).
Saeki, Y., et al., "Development and Characterization of Cationic Liposomes Conjugated with HVJ (Sendai Virus): reciprocal Effect of Cationic Lipid For In Vitro and In Vivo Gene Transfer", Human gene Therapy, 8(17):2133-2141 (1997).
Saenz-Badillos, et. al., "RNA as a tumor vaccine: a review of the literature", Experimental Dermatology; 2001; pp. 143-154; vol. 10, Issue 3.
Samad et al, "Liposomal drug delivery systems: an updated review," Curr Drug Deliv. Oct. 2007;4(4):297-305.
Saxena et al., "Induction of immune responses and protection in mice against rabies using a self-replicating RNA vaccine encoding rabies virus glycoprotein," Veterinary Microbiology; vol. 136(1-2); 2009; pp. 36-44.
Scheel, et al., "Toll-like receptor-dependent activation of several human blood cell types by protamine-condensed mRNA," European Journal of Immunology; 2005; pp. 1557-1566.
Schirrmacher, et al., "Intra-pinna anti-tumor vaccination with self-replicating infectious RNA or with DNA encoding a model tumor antigen and a cytokine," Gene Therapy; 2000, pp. 1137-1147; vol. 7.
Schlesinger et al., "Alphavirus vectors for gene expression and vaccines," Current Opinion in Biotechnology, 1999, 10:434-439.
Semple et al. "Efficient encapsulation of antisense oligonucleotides in lipid vesicles using ionizable aminolipids: formation of novel small multilamellar vesicle structures," Biochimica et Biophysica Acta (BBA)—Biomembranes, vol. 1510, 2001, pp. 152-166.
Semple et al., "Rational design of cationic lipids for siRNA delivery," Nature Biotechnology, v. 28:172-176 (2010).
Sharma, et al., "To scale or not to scale: the prinicples of dose extrapolation," British Journal of Pharmacology; 2009; pp. 907-921; vol. 157.
Silva, et al, "Effect of ultrasound parameters for unilamellar liposome preparation," Ultrasonics Sonochemistry, 2010, 17 (3), 628-32.
Singh et al., "The Effect of CTAB Concentration in Cationic PLG Microparticles on DNA Adsorption and in Vivo Performance," Pharmaceutical Research, (2003), vol. 20, pp. 247-251.
Singh, et al., "Cationic microparticles: A potent delivery system for DNA vaccines," Proc Natl Acad Sci USA; 2000; pp. 811-816; vol. 97(2).

(56) References Cited

OTHER PUBLICATIONS

Smerdou, et al., "Non-viral amplification systems for gene transfer: Vectors based on alphaviruses," Curr Opin Mol Ther; 1999; pp. 244-251; vol. 1(2).
Smith Korsholm, Karen, et al. "The adjuvant mechanisms of cationic dimethyldioctadeclammonium liposomes," Immunology 121(2) (2007): 216-226.
Strejan, "Suppression of Chronic-Relapsing Experimental Allergic Encephalomyelitis in Strain-13 Guinea Pigs by Administration of Liposome-Associated Myelin Basic Protein", Journal of Neuroimmunology; vol. 7; 1984; pp. 27-41.
Stuart, et al, "A new liposomal formulation for antisense oligodeoxynucleotides with small size, high incorporation efficiency and good stability", Biochimica et Biophysica Acta, 1463(2), 219-229 (2000).
Sugiyama, T., "Immunoadjuvant effects of polyadenylic:polyuridytic acids through TLR3 and TLR7", Int. Immunolo. 20(1): 1-9 (2007).
Summary of stability data for licensed vaccines as of Nov. 29, 2012.
Szoka, et al., "Procedure for preparation of liposomes with large internal aqueous space and high capture by reverse-phase evaporation," Proc Natl Acad Sci U S A, 75(9) (1978): 4194-4198.
Taylor, et al., "DNA vaccination against respiratory syncytial virus in young calves." Vaccine; 2005; pp. 1242-1250; vol. 23(10).
Zimmermann et al., "RNAi-mediated gene silencing in non-human primates," Nature. vol. 441, pp. 111-114 (2006).
ThermoFisher—Ribosomal RNA Sizes.
Third Party Observations under Art. 115 EPC Nov. 3, 2016 from EP Appl. No. 11736499.2; pp. 1-17.
Tseng et al., "Liposomes incorporated with cholesterol for drug release triggered by magnetic field," Journal of Medical and Biological Engineering, vol. 27, No. 1 (2007), 29-34.
U.S. Appl. No. 17/560,019, filed Dec. 22, 2021.
U.S. Appl. No. 17/560,052, filed Dec. 22, 2021.
U.S. Appl. No. 17/560,059, filed Dec. 22, 2021.
U.S. Appl. No. 17/560,092, filed Dec. 22, 2021.
U.S. Appl. No. 17/560,116, filed Dec. 22, 2021.
U.S. Appl. No. 17/560,138, filed Dec. 22, 2021.
Ulmer, et al., "Heterologous Protection Against Influenza by Injection of DNA Encoding a Viral Protein." Science; 1993; pp. 1745-1749; vol. 259.
Zuckerman, "The importance of injecting vaccines into muscle," BMJ, vol. 321, pp. 1237-1238 (2000).
Vajdy, et al., "Mucosal adjuvants and delivery systems for protein-, DNA- and RNA-based vaccines." Immunol Cell Biol. Dec. 2004;82(6):617-27.
Vasiljeva et al., "Identification of a novel function of the alphavirus capping apparatus," Journal of Biological Chemistry, 2000; 275(23):17281-17287.
Vassilev, et al., "Microparticle-mediated RNA immunization against bovine viral diarrhea virus," Vaccine; 2001; pp. 2012-2019; vol. 19.
Vignuzzi, et al., "Naked RNA immunization with replicons derived from poliovirus and Semliki Forest virus genomes for the generation of a cytotoxic T cell response against the influenza A virus nucleoprotein," Journal of General Virology; 2001; pp. 1737-1747; vol. 82(7).
Wang, et al., "pH-sensitive immunoliposomes mediated target-cell-specific delivery and controlled expression of a foreign gene in mouse," Proc. Natl. Acad. Sci. USA; 1987; pp. 7851-7855; vol. 84.
Ward, et al., "Generation of CTL responses using Kunjin replicon RNA," Immunology and Cell Biology; 2003; pp. 73-78; vol. 81(1).
Weide, et al., "Direct Injection of Protamine-protected mRNA: Results of a Phase 1/2 Vaccination Trial in Metastatic Melanoma Patients," Journal of Immunotherapy; 2009; pp. 498-507, vol. 32(5).
Weide, et al., "Results of the First Phase I/II Clinical Vaccination Trail with Direct Injection of mRNA," Journal of Immunotherapy; 2008; pp. 180-188; vol. 31(2).
Whitehead, et al., "Knocking down barriers: advances in siRNA delivery." Nature Reviews Drug Discovery; 2009; pp. 129-138; vol. 8.
Wilson et al., "Biological properties of poliovirus encapsulated in lipid vesicles: Antibody resistance and infectivity in virus-resistance cells", Proc. Natl. Acad. Sci. USA, 1977; pp. 3471-3475; vol. 74, No. 8.
Wilson, et al., "The Introduction of Poliovirus RNA into Cells via Lipid Vesicles (Liposomes)," Cell; 1979; pp. 77-84; vol. 17.
Wilson et al.; "The combination of stabilized plasmid lipid particles and lipid nanoparticle encapsulated CpG containing oligodexoynucleotides as a systemic genetic vaccine". The Journal of Gene Medicine; 11; pp. 14-25; 2009.
Wloch, et al., "Safety and Immunogenicity of a Bivalent of Cytomegalovirus DNA Vaccine in Healthy Adult Subjects," J Infect Dis; 2008; pp. 1634-1642; vol. 197(2).
Xiong et al., "Sindbis virus: an efficient, broade host range vector for gene expression in animal cells," Science, 243:1188-1191 (1989).
Yamamoto, et al., "Current prospects for mRNA gene delivery." Eur. Journal of Pharma and Biopharm, 2009, 71, 484-489.
Yi, et al., "A Cationic Lipid Emulsion/DNA Complex as a Physically Stable and Serum-Resistant Gene Delivery," Pharmaceutical Research; 2000; pp. 314-320; vol. 17(13).
Ying et al. "Cancer therapy using a self-replicating RNA vaccine" Nat. Med.; vol. 5(7); pp. 823-827; 1999.
Yoder, et al., "Role of Complement in Neutralization of Respiratory Syncytial Virus" J Med Virol; 2004; pp. 688-694; vol. 72.
Yoffe, et al., "Predicting the sizes of large RNA molecules" PNAS; vol. 105(43); 2008; pp. 16153-16158.
Yoneyama, et al, "RIG-I family RNA helicases; cytoplasmic sensor for antiviral innate immunity," Cytokine & Growth Factor Reviews. (2007), vol. 18, pp. 545-551.
Yoon, et al., "DNA-Mediated Immunization of Mice with Plasmid Encoding HBs Antigen." J. Korean Med Sci; 1999; pp. 187-192; vol. 14.
Zhang, J., et al., "Ionization Behavior of Amino Lipids for siRNA Delivery; Determination of Ionization Constants, SAR, and the Impact of Lipid pKa on Cationic Lipid-Biomembrane Interactions," Langmuir, 27(5): 1907-1914 (2011).
Zhou, et al., "RNA Melanoma Vaccine: Induction of Antitumor Immunity by Human Glycoprotein 100 mRNA Immunization", Human Gene Therapy, 10(16): 2719-2724 (1999).
Zhou, X., et al., "Self-replicating Semliki Forest virus RNA as recombinant vaccine", Vaccine 12(16): 1510-1514 (1994).
Amidi et al., "Antigen-expressing immunostimulatory liposomes as a genetically programmable synthetic vaccine." Systems and Synthetic Biology, vol. 5, 2011, pp. 21-31 (2011).
Amidi et al., "Optimization and quantification of protein synthesis inside liposomes." Journal of Liposome Research, vol. 20(1), 2010, pp. 73-83 (2010).
Bauer et al., "Toll-Like Receptors (TLRs) and Innate Immunity," Handbook of Experimental Phamacology, ISBN 978-3-540-72166-6, 2008, pp. i-xi, 1-240, and a cover page (2008).
"Chapter 27: RNA-based therapies," Drug Discovery Handbook, Shayne Cox Gad (Ed.), Wiley Interscience, Cary, 2005, pp. 1259-1308.
"DLinDMA," Excerpt from "Chemical Book" on DLinDMA Sep. 9, 2021, https://www.chemicalbook.com/Chemical/ProductProperty_EN_CB44797047.htm.
"mRNA-ONLY™ Prokaryotic mRNA Poly(A)-Tailing," Oct. 2006 www.EpiBio.com.
"Revised Release on the Pressure along the Melting and Sublimation Curves of Ordinary Water Substance," The International Association for the Properties of Water and Steam, Pizen, Czech Republic, Sep. 2011, pp. 1-7.
"Stocking Up: Reagents and Supplies Quick Reference Guide," discover bio-rad.com, BioRad Product catalog post-published evidence in EP Opposition No. 3682905.
"Third Party Observations in accordance with Article 115 EPC," dated Mar. 8, 2019, filed in EP Application No. 12738679.5.
"Transfectam," PubChem, Sep. 11, 2021, https://pubchem.ncbi/nlm.nih.gov/compound/Transfectam.
"Virus-Like Particles (VLPs) in Supramolecular Chemistry," Comprehensive Supermolecular Chemistry II, vol. 1, J. L. Atwood, G. W. Gokel, (Eds.), Elsevier, Amsterdam, 2017.

(56) References Cited

OTHER PUBLICATIONS

Adler et al., "Role of human cytomegalovirus UL131A in cell type-specific virus entry and release," J. Gen. Virol. (2006), vol. 87, pp. 2451-2460.
Afeyan et al.; U.S. Appl. No. 61/361,828, filed Jul. 6, 2010.
Afeyan et al., U.S. Appl. No. 61/404,413, filed Oct. 1, 2010.
Agris et al., "Thermodynamic Contribution of Nucleoside Modifications to Yeast tRNAphe Anticodon Stem Loop Analogs," Acta Biochimica Polonica (1999), vol. 46, No. 1, pp. 163-172.
Aissaoui et al., "Efficient topical delivery of plasmid DNA to lung in vivo mediated by putative triggered, PEGylated pDNA nanoparticles", Journal of Controlled Release (2011), vol. 154, No. 3, pp. 275-284.
Amidi, "Induction of humoral and cellular immune responses by antigen-expressing immunostimulatory liposomes." Journal of Controlled Release (2012), vol. 164, pp. 323-330.
Anderson et al., "Nucleoside modifications in RNA limit activation of 2'-5'-oligoadenylate synthetase and increase resistance to cleavage by RNase L," Nucleic Acids Research (2011), vol. 39, No. 21, pp. 9329-9338.
Andries et al., "N(1)-Methylpseudouridine—Incorporated mRNA Outperforms Pseudouridine-Incorporated mRNA by Providing Enhanced Protein Expression and Reduced Immunogenicity in Mammalian Cell Lines and Mice," Journal of Controlled Release (2015), vol. 217, pp. 337-344.
Annex to the communication in Opposition against EP 3 492 109 B1 by the Opposition Division, Apr. 13, 2022, EP Application No. 18 213 451.0.
A-Plus™ Poly(A) Polymerase Tailing Kit Protocol Nov. 16, 2006 (Capture Date).
Application as filed with the application No. EP 18 153 312.6, filed Jun. 8, 2012.
Arvin, A. M. and Gershon, A. A., "Live Attenuated Varicella Vaccine," Annu. Rev. Microbial. (1996), vol. 50, pp. 59-100.
Aso and Yoshioka, "Effect of freezing rate on physical stability of lyophilized cationic liposomes," Chem. Pharm. Bull. (2005), vol. 53, No. 3, pp. 301-304.
Ausubel et al., Short protocols in molecular biology., Chapter 11, "Immunology" 2002.
Bahl et al., "Preclinical and Clinical Demonstration of Immunogenicity by mRNA Vaccines against H10N8 and H7N9 Influenza Viruses," Mol. Ther. (2017), vol. 25, No. 6, pp. 1316-1327.
Bai et al., "Gene Transfer to Vein Graft Wall by HVJ-Liposome Method: Time Course and Localization of Gene Expression," Ann. Thorac. Surg. (1998), vol. 66, pp. 814-820.
Balasuriya et al., "Expression of the two major envelope proteins of equine arteritis virus as a heterodimer is necessary for induction of neutralizing antibodies in mice immunized with recombinant Venezuelan Equine Encepahalitis Virus Replicon Particles," J. Virol. (2000), vol. 74, No. 22, pp. 10623-10630.
Bancel et al., U.S. Appl. No. 61/618,862, filed Apr. 2, 2012.
Bancel, U.S. Appl. No. 61/570,690, filed Dec. 14, 2011.
Bancel, U.S. Appl. No. 61/578,271, filed Dec. 21, 2011.
Barichello et al., Chapter 32 Complexation of siRNA and pDNA with cationic liposomes: the important aspects in lipoplex preparation, Liposomes, Methods Molecular Biology, Volkmar Weissig (Ed.), Humana Press, Arizona, 2010.
Barratt, "Therapeutic applications of colloidal drug carriers." PSTT (2000), vol. 3, No. 5, pp. 163-171.
Bauer et al., "Toll-like receptors (TLRs) and innate immunity", Handbook of Experimental Pharmacology, ISBN 978-3-540-72166-6, 2008, pp. i-xi, 1-240, and a cover page (2008).
Bettinger T et al., "Peptide-mediated RNA delivery: a novel approach for enhanced transfection of primary and post-mitotic cells," Nucleic Acids Research (2001), vol. 29, No. 18, pp. 3882-3891.
Bettinger, T. and Reed, M. L., "Recent Developments in RNA-Based strategies for cancer gene therapy", Current Opinion in Molecular Therapeutics (2001), vol. 3, No. 2, pp. 116-124.
Blakney, "The next generation of RNA vaccines: self-amplifying RNA," Biochem (Lond) (2021), vol. 43, No. 4, pp. 14-17.
Brand et al., "Biosynthesis of a Hypermodified Nucleotide in *Saccharomyces carlsbergensis* 17S and HeLa-Cell 18S Ribosomal Ribonucleic Acid," Biochem. J. (1978), vol. 169, pp. 71-77.
Britt et al., "Cell surface expression of human cytomegalovirus (HCMV) gp55-116 (GB): use of HCMV-recombinant vaccinia virus-infected cells in analysis of the human neutralizing antibody response," J. Virol. (1990), vol. 64, No. 3. pp. 1079-1085.
Britt et al., "Cytomegalovirus," In Fields Virology, 3rd edition, BN Fields, DM Knipe, PM Howley (Ed.), Lippincott-Raven, Philadelphia, 1996, pp. 2493-2523.
Britt et al., "Human cytomegalovirus virion proteins," Hum. Immunol. (2004), vol. 65, pp. 395-402.
Cha et al., "Human cytomegalovirus clinical isolates carry at least 19 genes not found in laboratory strains," J. Virol. (1996), vol. 70, No. 1, pp. 78-83.
Chang et al., "Synthesis and Solution Conformation Studies of 3-substituted Uridine and Pseudouridine Derivatives," Bioorganic & Medicinal Chemistry (2008), vol. 16, pp. 2676-2686.
Chatterjee et al., "The Archaeal COG1901/DUF358 SPOUT-Methyltransferase Members, Together. with Pseudouridine Synthase Pus 10, Catalyze the Formation of 1-Methylpseudouridine at Position 54 of tRNA," RNA (2012), vol. 18, No. 3, pp. 421-433.
Chee et al., "Analysis of the protein-coding content of the sequence of human cytomegalovirus strain AD169," Curr. Top. Microbiol. Immunol. (1990), vol. 154, pp. 125-169.
Chee et al., Uncharacterized Protein UL128, UniProtKB/Swiss-Prot: Primary Accession No. P16837, Dep. Feb. 1, 1991.
Chen et al., "An Overview of Liposome Lyophilization and its Future Potential," Journal of Controlled Release (2010), vol. 142, No. pp. 299-311.
Chen et al., "Influence of particle size on the in vivo potency of lipid nanoparticle formulations of SiRNA," J. Control Release, (2016), vol. 235, pp. 236-244.
Cheng et al., "Naked RNA vaccine controls tumors with down-regulated MHC class I expression through NK cells and perforin-dependent pathways," Eur J Immunol. (2004), vol. 34, No. 7, pp. 1892-1900.
Christ, "Gefriertrocknung mit System" (with D6a, a timestamp, showing that this document was available as of Jan. 22, 2010).
Christ, "Smart Freeze Drying" Manual, Basic Principles, Optimum Procedures and Applications, Jan. 2010.
Communication of the Board of Appeal dated Mar. 25, 2021, in relation to the Opposition of European Patent No. 2590676B1 (Application No. 11741348.4), 12 pages.
Compton, "Receptors and immune sensors: the complex entry path of human cytomegalovirus," Trends Cell. Bio. (2004), vol. 14, No. 1, pp. 5-8.
Cortesi et al.: "Effect of DNA complexation and freeze-drying on the physicochemical characteristics of cationic liposomes," Antisense & Nucleic Acid Drug Development, (2000), vol. 10, pp. 205-215.
CRC Handbook of Chemistry and Physics, 101st Edition, CRC Press, Boca Raton, 2020—Section 6, Vapor Pressure of Ice.
Cullis et al., U.S. Appl. No. 61/280,510, filed Nov. 4, 2009.
Davis, F. F. and Allen, F. W. "Ribonucleic Acids from Yeast which Contain a Fifth Nucleotide" Journal of Biological Chemistry (1957), vol. 227, pp. 907-915.
Davison et al., "The human cytomegalovirus genome revisited: comparison with the chimpanzee cytomegalovirus genome," J. Gen. Virol. (2003), vol. 84, pp. 17-28.
Davison, A. J., "UL115; gL [Human Herpesvirus 5]," NCBI Reference Sequence: YP_081555.1, Dep. Sep. 16, 2004.
Davison, A. J., "Ul 130 [Human Herpesvirus 5]," NCBI Reference Sequence: YP_081565.1, Dep. Sep. 16, 2004.
Davison, A. J., "UL75; gH [Human Herpesvirus 5]," NCBI Reference Sequence: YP_081523.1, Dep. Sep. 16, 2004.
Davison. A. J., "UL131A [Human Herpesvirus 5]," NCBI Reference Sequence: YP_081566.1, Dep. Sep. 16, 2004.
De Fougerolles, U.S. Appl. No. 61/576,705, filed Dec. 16, 2011.
Depledge et al., "Deep Sequencing of Distinct Preparations of the Live Attenuated Varicella-Zoster Virus Vaccine Reveals a Conserved Core of Attenuating Single-Nucleotide Polymorphisms," J. Virology (2016), vol. 90, No. 19, pp. 8698-8704.

(56) References Cited

OTHER PUBLICATIONS

Dolan et al, "Genetic Content of Wild-Type Human Cytomegalovirus", J. Gen. Virol. (2004), vol. 85, pp. 1301-1312.
Dunn et al., "Functional profiling of a human cytomegalovirus genome," Proc. Natl. Acad. Sci. USA (2003), vol. 100, No. 24, pp. 14223-14228.
Durbin et al., "RNAs Containing Modified Nucleotides Fail To Trigger RIG-I Conformational Changes for Innate Immune Signaling." mBio. (2016), vol. 7, No. 5:e00833-16, pp. 1-11.
Dwarki et al., "Cationic Liposome-Mediated RNA Transfection," Methods in Enzymology (1993), vol. 217, pp. 644-654.
Earl and Townsend "A Chemical Synthesis of the Nucleoside I-Methylpseudouridine," J. Heterocyclic Chem (1977), vol. 15, pp. 699-700.
Eastman et al., "Influence of Phospholipid Asymmetry on Fusion between Large Unilamellar Vesicles," Biochemistry, vol. 31, (1992), pp. 4262-4268.
Eberhardt et al. "Modulation of mRNA Stability as a Novel Therapeutic Approach," Pharmacology & Therapeutics (2007), vol. 114, pp. 56-73.
Elkington et al., "Ex Vivo Profiling of CD8+ -T-Cell Responses to Human Cytomegalovirus Reveals Broad and Multispecific Reactivities in Healthy Virus Carriers," Journal of Virology (2003), vol. 77, No. 9, pp. 5226-5240.
Er et al., "The encapsulation and release of guanosine from PEGylated liposomes," Journal of Liposome Research (2009), vol. 19, No. 1, pp. 29-36.
Ernsting et al., "Factors controlling the pharmacokinetics, biodistribution and intratumoral penetration of nanoparticles," J. Control Release (2013), vol. 172, No. 3, pp. 782-794.
Faneca, H et al., "Cationic Liposome-Based Systems for Nucleic Acid Delivery: From the Formulation Development to Therapeutic Applications," Drug Delivery Systems: Advanced Technologies Potentially Applicable in Personalised Treatment, Advances in Predictive, Preventive and Personalised Medicine (2013). vol. 4, pp. 153-184.
Faure et al., "Control of the in vivo Biodistribution of Hybrid Nanoparticles with Different Poly(ethylene glycol) Coatings," Small (2009), vol. 5, No. 22, pp. 2565-2575.
Felgner et al., "Cationic Lipid-Mediated Transfection in Mammalian Cells: Lipofection", J. Tiss. Cult. Meth. (1993), vol. 15, pp. 63-68.
Fraenkel-Conrat, "Togaviridae", Virology Second Edition, Prentice-Hall Inc., Englewood, 1988; p. 2 p. 99.
Franti et al., U.S. Appl. No. 16/114,621, filed Aug. 28, 2018.
Freer, G. and Pistello, M., "Varicella-zoster virus infection: natural history, clinical manifestations, immunity and current and future vaccination strategies," New Microbial. (2018), vol. 41, No. 2, pp. 95-105.
Frolov et al., "Alphavirus-based expression vectors: Strategies and applications," Proc. Natl. Acad. Sci. USA (1996), vol. 93, pp. 11371-11377.
Gao, H. and Hui, K.M., "Synthesis of a novel series of cationic lipids that can act as efficient gene delivery vehicles thorugh systematic heterocyclic substitution of cholesterol derivatives," Gene Therapy (2001), vol. 8, pp. 855-863.
Garcia-Valcarcel et al. "Induction of neutralizing antibody and T-cell responses to varicella zoster virus (VZV) using Ty-virus-like particles carrying fragments of glycoprotein E (gE)," Vaccine (1997) vol. 15, No. 6-7, pp. 709-719.
Geall et al., U.S. Appl. No. 16/714,877, filed Dec. 16, 2019.
Geall et al., U.S. Appl. No. 17/511,762, filed Oct. 27, 2021.
Geall et al., U.S. Appl. No. 61/223,347, filed Jul. 6, 2009.
Geall et al., U.S. Appl. No. 61/505,088, filed Jul. 16, 2011.
Geall et al., U.S. Appl. No. 61/529,878, filed Aug. 31, 2011.
Geall, U.S. Appl. No. 17/512,258, filed Oct. 27, 2021.
Geall, U.S. Appl. No. 17/848,294, filed Jun. 23, 2022.
Geall, U.S. Appl. No. 17/848,299, filed Jun. 23, 2022.
Geall, U.S. Appl. No. 17/848,337, filed Jun. 23, 2022.
Geldmacher et al., "Therapeutic vaccination for cancer immunotherapy: Antigen selection and clinical responses", Human Vaccines (2011), vol. 7 Supl., 1, pp. 115-119.
Gennaro, "Parenteral Preparations,"Remington: The Science and Practice of Pharmacy, vol. 1, 20th Edition, Alfonso R. Gennaro (Ed.), Philadelphia College of Pharmacy and Science, Philadephia, 2000.
Giraud et al., "Generation of monoclonal antibodies to native human immunodeficiency virus type 1 envelope glycoprotein by immunization of mice with naked RNA," J. Virol, Methods, (1999), vol. 79, No. 1, pp. 75-84.
Goel et al., "Distinct antibody and memory B cell responses in SARS-COV-2 naïve and recovered individuals after mRNA vaccination," Science Immunology (2021), vol. 6, pp. 1-19.
Guild et al., U.S. Appl. No. 61/494,745, filed Jun. 8, 2011.
Guild et al., U.S. Appl. No. 61/494,882, filed Jun. 8, 2011.
Hahn et al., "Deletion Mapping of the Encephalomyocarditis Virus Primary Cleavage Site". J. Virol. (2001), vol. 75, No. 15, pp. 7215-7218.
Hassett et al., "Optimization of Lipid Nanoparticles for Intramuscular Administration of mRNA Vaccines," Mol. Ther. Nucleic Acids (2019), vol. 15, pp. 1-11.
Hatakeyama, et al., "Systemic delivery of siRNA to tumors using a lipid nanoparticle containing a tumor-specific cleavable PEG-lipid," Biomaterials (2011), vol. 32, pp. 4306-4316.
Ho, "Cytomegalovirus," In Principles and Practice of Infectious Diseases, GL Mandell, RG Douglas, and JE Bennett (Ed.), Wiley, New York, 1979, pp. 1307-1323.
Hobo et al., "Immunogenicity of Dendritic Cells Pulsed with MAGE3, Survivin and B-Cell Maturation Antigen mRNA for Vaccination of Multiple Myeloma Patients," Cancer Immunol. Immunother. (2013), vol. 62, pp. 1381-1392.
Hobo et al., "Improving Dendritic Cell Vaccine Immunogenicity by Silencing PD-1 Ligands using siRNA-lipid Nanoparticles Combined with Antigen mRNA Electroporation," Cancer Immunol. Immunother. (2013), vol. 62, pp. 285-297.
Hobom et al., "Fast screening procedures for random transposon libraries of cloned herpesvirus genomes: mutational analysis of human cytomegalovirus envelope glycoprotein genes," J. Virol. (2000), vol. 74, No. 17, pp. 7720-7729.
Hoerr, "Plenary Lectures and Oral Presentations," Tissue Engineering (2007), vol. 13, No. 4, pp. 886-887.
Hoffmann et al., "Physiochemical Properties of Bile Acids and their Relationship to Biological Properties: An Overview of the Problem," J. Lip. Res. (1984), vol. 25, pp. 1477-1489.
https://www.convertunits.com/from/atmosphere+[standard]/to/mtorr; Cited in opposition proceeding in EP18153312.6 dated Mar. 4, 2022.
Hwang et al., "alpha-Methylprednisolone Conjugated Cyclodextrin Polymer-Based Nanoparticles for Rheumatoid Arthritis Therapy," International Journal of Nanomedicine (2008), vol. 3, No. 3, pp. 359-371.
Immordino et al., "Stealth liposomes: review of the basic science, rationale, and clinical applications, existing and potential," International Journal of Nanomedicine (2006) vol. 1, No. 3, pp. 297-315.
International Search Report for International Application No. PCT/2012/045854 dated May 9, 2014.
Janeway et al., Immunobiology: The Immune System in Health and Disease, 5th edition. Garland Science, New York; 2001. Induced innate responses to infection. Part I, Chapter 2, "Induced innate responses to infection" pp. 87-106: Available from: https://www.ncbi.nlm.nih.oov/books/NBK27122/.
Jones et al., "Long-term storage of DNA-free RNA for use in vaccine studies," Bio Techniques (2007), vol. 43, No. 5, pp. 675-681.
Ju et al., "Novel Cholesterol-Based Cationic Lipids as Transfecting Agends of DNA for Efficient Gene Delivery," int. J. Mol. Sci. (2005), vol. 16, pp. 5666-5681.
Kamrud et al., "Development and characterization of promoterless helper RNAs for the production of alphavirus replicon particle," J. Gen. Virol. (2010), vol. 91, pp. 1723-1727.

(56) References Cited

OTHER PUBLICATIONS

Karikó et al., "Increased Erythropoiesis in Mice Injected with Submicrogram Quantities of Pseudouridine—Containing mRNA Encoding Erythropoietin," Mal. Ther. (2012), vol. 20, No. 5, pp. 948-953.
Karikó et al., "Generating the optimal mRNA for therapy: HPLC purification eliminates immune activation and irmpoves translation of nucleoside-modified, protein-encoding mRNA," Nucleic Acids Research (2011), vol. 39, No. 21, e142, pp. 1-10.
Karikó et al., "Incorporation of Pseudouridine Into mRNA Yields Superior Nonimmunogenic Vector With Increased Translational Capacity and Biological Stability," Molecular Therapy (2008), vol. 16, No. 11, pp. 1833-1840.
Karikó et al., "Suppression of RNA Recognition by Toll-Like Receptors: The Impact of Nucleoside Modification and the Evolutionary Origin of RNA," Immunity (2005), vol. 23, pp. 165-175.
Karikó, K. and Weissman, D., "Naturally Occurring Nucleoside Modifications Suppress the Immunostimulatory Activity of RNA: Implication for Therapeutic RNA Development," Curr Opin Drug Disc & Dev. (2007), vol. 10, No. 5, pp. 523-532.
Kawano et al., "Effects of Polyethylene Glycol Spacer Length and Ligand Density on Folate Receptor Targeting of Liposomal Doxorubicin In Vitro." Journal of Drug Delivery (2011), vol. 2011, No. 160967, pp. 1-6.
Kawauchi et al., "Gene Therapy for Attenuating Cardiac Allograft Arteriopathy using Ex Vivo E2F Decoy Transfection by HVJ-AVE-Liposome Method in Mice and Nonhuman Primates," Circ. Res. (2000), vol. 87, pp. 1063-1068.
Kierzek, E., and Kierzek, R., "Influence of N6-Isopentenyladenosine ($k^6A$) on Thermal Stability of RNA Duplexes," Biophysical Chemistry (2001), vol. 91, pp. 135-140.
Kimura et al., "Recombinant Varicella-Zoster Virus Glycoproteins E and I: Immunologic Responses and Clearance of Virus in a Guinea Pig Model of Chronic Uveitis," J. Infect. Disease (1998), vol. 178, pp. 310-317.
Kimura et al., "Varicella-Zoster Virus Glycoproteins E and | Expressed in Insect Cells Form a Heterodimer That Requires the N-Terminal Domain of Glycoprotein 1;" Virology (1997), vol. 233, pp. 382-391.
Kirman et al., "Enhanced Immunogenicity to Mycobacterium tuberculosis by Vaccination with an Alphavirus Plasmid Replicon Expressing Antigen 85A," Infection and Immunity (2003), vol. 71, No. 1. pp. 575-579.
Kit Protocol Nov. 16, 2006 (Capture Date).
Kita et al., "Replication of Genetic Information with Self-Encoded Replicase in Liposomes." ChemBioChem (2008), vol. 9, No. 15, pp. 2403-2410.
Kitajima et al., "Efficient Transfer of Synthetic Ribozymes into Cells using Hemagglutinating Virus of Japan (HVJ)-Cationic Liposomes," The Journal of Biological Chemistry (1997), vol. 272, No. 43, pp. 27099-27106.
Klibanov et al.; "Amphipathic polyethyleneglycols effectively prolong the circulation time of liposomes", FEBS Letters (1990), vol. 268, No. 1, pp. 235-237.
Kreiter et al., "Tumor Vaccination using Messenger RNA: Prospects of a Future Therapy," Current Opinion in Immunology (2011), vol. 23, pp. 399-406.
Kumar et al., "New Histidylated Cationic Lipids for DNA- and MRNA—Based Lipofection," Molecular Therapy (2004), vol. 9, Suppl. 1, pp. S258-S259.
Kumar et al., "Single histidine residue in head-group region is sufficient to impart remarkable gene transfection properties to cationic lipids: evidence for histidine-mediated membrane fusion at acidic pH," Gene Therapy (2003), vol. 10, pp. 1206-1215.
Kutinova et al., "Immune response to vaccinia virus recombinants expressing glycoproteins gE, GB, gH, and gL of varicella-zoster virus," Virol. (2001), vol. 280, pp. 211-220.
Leroueil et al., "Wide varieties of cationic nanoparticles induce defects in supported lipid bilayers" Nano Lett. (2008), vol. 8, No. 2. pp. 420-424.
Li et al., "Protection against Respiratory Syncytial Virus Infection by DNA Immunization," J Exp Med. (1998), vol. 188, pp. 681-688.
Liu, D. and Huang, L., "Size Homogeneity of a Liposome Preparation is Crucial for Liposome Biodistribution In Vivo," Journal of Liposome Research (1992), vol. 2, No. 1, pp. 57-66.
Liu, Y. and Huang L., "Designer Lipids Advance Systemic siRNA Delivery." Molecular Therapy (2010), vol. 18, No. 4, pp. 669-670.
Ljungman et al., "Definitions of cytomegalovirus infection and disease in transplant recipients," Clin. Infect. Dis. (2002), vol. 34, pp. 1094-1097.
Lui et al., U.S. Appl. No. 17/828,519, filed May 31, 2022.
Lundstrom, "Semliki Forest Virus Vectors for Gene Therapy," Expert Opinion on Biological Therapy (2003), vol. 3, No. 5, pp. 771-777.
Lv et al., "Toxicity of cationic lipids and cationic polymers in gene delivery," Journal of Controlled Release (2006), vol. 114, pp. 100-109.
Macagno et al., "Isolation of Human Monoclonal Antibodies That Potently Neutralize Human Cytomegalovirus Infection by Targeting Different Epitopes on the gH/gL/UL128-131A Complex," Journal of Virology (2010), vol. 84, No. 2, pp. 1005-1013.
MacLachlan, I., "Liposomal formulations for nucleic acid delivery," Antisense Drug Technologies, 2nd Edition, Chapter 9, 237-270, 2007.
Mahato, "Water insoluble and soluble lipids for gene delivery," Adv. Drug Delivery Rev. (2005), vol. 57; pp. 699-712.
Mandal et al., "Delivery of Macromolecules into Cytosol using Liposomes Containing Hemolysin," Methods in Enzymology (2003), vol. 372, pp. 319-339.
Mann et al., "DNA Transfer into Vascular Smooth Muscle using Fusigenic Sendai Virus (HJV)-Liposomes," Molecular and Cellular Biochemistry (1997), vol. 172, pp. 3-12.
Matsuura, et al., "Polycation liposome-mediated gene transfer in vivo," Biochimica et Biophysica Acta (2003), vol. 1612, pp. 136-143.
McGown, "UV Absorbance Measurements of DNA in Microplates," BioTechniques (2000), vol. 28, No. 1, pp. 60-64.
Mocarski et al., "Cytomegalovirus and their replication," In Fields Virology, 4th edition, vol. 2, 2001, DM Knipe and PM Howley (Ed.), Lippincott Williams and Wilkins, Philadelphia, pp. 2629-2673.
Molina et al., "The stability of lyophilized lipid/DNA complexes during prolonged storage," Journal of Pharmaceutical Sciences (2004), vol. 93, No. 9, pp. 2259-2273.
Monslow et al., "Immunogenicity generated by mRNA vaccine encoding VZV gE antigen is comparable to adjuvanted subunit vaccine and better than live attenuated vaccine in nonhuman primates," Vaccine (2020), vol. 38, pp. 5793-5802.
Montana et al. "Employment of Cationic Solid-Lipid Nanoparticles as RNA Carriers," Bioconjugate Chem. (2007), vol. 18, pp. 302-308.
Motorin and Helm "5-Methylcytosine in RNA: Detection, Enzymatic Formation and Biological Functions," Nucleic Acids Research (2010), vol. 38, No. 5. pp. 1415-1430.
Motorin and Helm, "RNA Nucleotide Methylation," Advanced Review (2011), vol. 2, pp. 611-631.
Murphy et al., "Coding potential of laboratory and clinical strains of cytomegalovirus," Proc. Natl. Acad. Sci. USA (2003), vol. 100, No. 25, pp. 14976-14981.
Narang et al., "Cationic Lipids with Increased DNA Binding Affinity for Nonviral Gene Transfer in dividing and Nondividing Cells," Bioconjugate Chem.(2005), vol. 16, pp. 156-166.
Notice of Opposition in relation to European Patent No. 2591103B1 (Appln No. 11736498.4) dated May 27, 2020 (17 pages).
Nucleic Acids in Innate Immunity, K. J. Ishii and S. Akira (Eds.), CRC Press, Boca Raton (2008).
Office Action dated Apr. 22, 2022. in U.S. Appl. No. 16/837,115.
Office Action dated Aug. 30, 2022, in U.S. Appl. No. 17/696,143.
Office Action dated Aug. 4, 2022, in U.S. Appl. No. 17/560,092.
Office Action dated Dec. 8, 2022, in U.S. Appl. No. 17/560,116.
Office Action dated Aug. 23, 2022, in U.S. Appl. No. 17/560,138.
Office Action dated Jul. 12, 2022, in U.S. Appl. No. 17/560,052.
Office Action dated Jul. 15, 2022, in U.S. Appl. No. 17/560,059.

(56) References Cited

OTHER PUBLICATIONS

Office Action dated May 25, 2022, in U.S. Appl. No. 13/808,080.
Office Action dated May 26, 2022, in U.S. Appl. No. 16/714,891.
Office Action dated May 31, 2022, in U.S. Appl. No. 17/560,019.
Office Action dated May 31, 2022, in U.S. Appl. No. 17/560,116.
Office Action dated Nov. 23, 2022, in U.S. Appl. No. 17/560,019.
Office Action dated Nov. 23, 2022, in U.S. Appl. No. 17/560,052.
Office Action dated Nov. 25, 2022, in U.S. Appl. No. 17/560,059.
Office Action dated Sep. 15, 2022, in U.S. Appl. No. 17/511,762.
Operating Manual Freeze-Dryer, Alpha 1-4 LCS Plus and Alpha 2-4 LSC Plus, Christ Rev. 1.5, Martin Christ Gefriertrocknungsanlagen GmbH, Harz, 2013.
Oussoren et al., "Lymphatic Uptake and Biodistribution of Liposomes After Subcutaneous Injection: III. Influence of Surface Modification with Poly(ethyleneglycol)," Pharmaceutical Research (1997), vol. 14, No. 10, pp. 1479-1484.
Pang et al., "Structure of a Modified Nucleoside in Archaebacterial tRNA which Replaces Ribosylthymine," The Journal of Biological Chemistry (1982), vol. 257, No. 7, pp. 3589-3592.
Parham, P.,"Innate Immunity", The Immune System Third edition, Janet Foltin (Ed.), Garland Science, Taylor & Francis Group, LLC, New York, 2009. Cover page, Table contents and pp. 49 and 50 common general knowledge.
Pascolo, "Messenger RNA-based vaccines", Expert Opin. Biol Ther. (2004), vol. 4, No. 8, pp. 1285-1294.
Pascolo, "Vaccination With Messenger RNA," Methods in Molecular Medicine (2006), vol. 127, pp. 23-40.
Patel et al., "The Importance of Apparent pKa in the Development of Nanoparticles Encapsulating SiRNA and mRNA," Trends Pharmacol. Sci. (2021), vol. 42, No. 6, pp. 448-460.
Peng et al., "The gH-gL complex of herpes simplex virus (HSV) stimulates neutralizing antibody and protects mice against HSV type 1 challenge," J. Virol., (1998), vol. 72, No. 1, pp. 65-72.
Pomeroy et al., "Cyotmegalovirus: epidemiology and infection control," Am. J. Infect. Control (1987), vol. 15, No. 3, pp. 107-119.
Poveda et al., "Establishing Preferred Product Characterization for the Evaluation of RNA Vaccine Antigens," Vaccines (2019), vol. 7, No. 131, pp. 1-14.
Qa'Dan et al., "pH-Induced Conformational Changes in Clostridium Difficile Toxin B," Infect & Immun. (2000), vol. 68, pp. 2470-2474.
Reap et al., "Cellular and humoral immune responses to alphavirus replicon vaccines expressing cytomegalovirus pp65, IE1 and GB proteins," Clin. Vacc. Immunol. (2007), vol. 14, No. 6, pp. 748-755.
Reichman et al., Nucleosides. CVI. Syntheses of 1-N-Methyl-5-(B-D-Ribofuranosyl)uracil (1-N-methyl-ψ-uridine) and its identity with a metabolite elaborated by Streptomyces Platensis var. Clarensis, The Journal of Antibiotics (1997), vol. XXX, No. 2, pp. 129-131.
Reijenga et al., "Development of Methods for the Determination of pKa Values, " Analytical Chemistry Insights (2013), vol. 8, pp. 53-71.
Response to Communication Pursuant to Article 94(3) submitted Jun. 26, 2017, in European Patent Application No. 12738679.5.
Response to Communication Under Rule 164(2)(b) and Article 94(3) of EPC of Mar. 9, 2018, in EP 12 722 942.5 (Moderna's submission of Jul. 9, 2018).
Robbins et al., "2'-O-Methyl-Modified RNAs Act as TLR7 Antagonists," Mol. Ther. (2007), vol. 15, No. 9, pp. 1663-1669.
Rubin, "Clinical approach to infection in the compromised host," In Infection in the Organ Transplant Recipient, 4th edition, R Rubin and LS Young (Ed.), Kluwer Academic Press, New York, NY, 2002, pp. 573-679.
Ryckman et al., "Characterization of the human cytomegalovirus gH/gL/UL 128-131 complex that mediates entry into epithelial and endothelial cells," J. Virol. (2008), vol. 82, No. 1, pp. 60-70.
Ryckman et al., "Human cytomegalovirus TR strain glycoprotein O acts as a chaperone promoting gH/gL incorporation into virions, but is not present in virions," J. Virol. (2010), vol. 84, No. 5, pp. 2597-2609.
Sadzuka et al., "Effect of Polyethyleneglycol (PEG) Chain on Cell Uptake of PEG-Modified Liposomes," J. Liposome Res. (2003), vol. 13, No. 2, pp. 157-172.
Sahin et al., "mRNA-based therapeutics—developing a new class of drugs," Nature Reviews Drug Discovery (2014), vol. 13, pp. 759-780.
Sambrook et al.., Molecular Cloning: A Laboratory Manual, 3rd edition, Cold Spring Harbor Laboratory Press, Plainview, 1989.
Sawai et al., "A Novel Method of Cell-Specific mRNA Transfection" Molecular Genetics and Metabolism (1998), vol. 64, pp. 44-51.
Schedin-Weiss et al., "Antiangiogenic Forms of Antithrombin Specifically Bind to the Anticoagulant Heparin Sequence," Biochemistry (2008), vol. 47, pp. 13610-13619.
Schlake et al., "Developing mRNA-Vaccine Technologies," RNA Biology (2012), vol. 9, No. 11., pp. 1319-1330.
Schleiss, "Cytomegalovirus vaccine development," Curr. Top. Microbiol. Immunol. (2008), vol. 325, pp. 361-382.
Schoenmaker, et al., "mRNA-lipid nanoparticle COVID-19 vaccines: Structure and stability," International Journal of Pharmaceutics (2021), vol. 601, 120586, pp. 1-13.
Search Report issued in EP Application No. 21298987 3, dated May 25, 2022.
Shah et al., "Shingrix for Herpes Zoster: A Review," Skin Therapy Lett. (2019) vol. 24, No. 4, pp. 5-7.
Shimamura et al., "Human cytomegalovirus infection elicits a glycoprotein M (gM)/gN-specific virus-neutralizing antibody response," J. Virol. (2006), vol. 80, No. 9, pp. ):4591-4600.
Soong et al., "PEG Molecular Weight and Lateral Diffusion of PEG-ylated Lipids in Magnetically Aligned Bicelles," Biochimica et Biophysica Acta (2007), vol. 1768, pp. 1805-1814.
Spelios et al., "Effect of spacer attachment sites in pH-sensitive headgroup expansion on cationic lipid-mediated gene delivery of three novel myristoyl derivatives," Biophys, Chem. (2007), vol. 129, pp. 137-147.
Sriwongsitanont, et al. "Physiochemical Properties of PEG-Grafted Liposomes." Chem Pharm Bull (2002), vol. 50, No. 9, pp. 1238-1244.
Stagno et al., "Cytomegalovirus," In Infectious Diseases of the Fetus and Newborn Infant, 6th edition, JS Remington and JO Klein (Ed.), WB Saunders, Philadelphia, PA, 1995, pp. 312-353.
Stryer, Chapter 2, Protein Structure and Function, Biochemistry 4th Ed., W. H. Freeman and Company, New York, 1995.
Su et al., "In Vitro and in Vivo mRNA Delivery using Lipid-Enveloped pH-Responsive Polymer Nanoparticles," Molecular Pharmaceutics (2011) vol. 8, pp. 774-787.
Submitted claims to the EPO on Sep. 30, 2008 in the case EP 06 81 3536.7 (EP1979364) prior art under Art. 54(2) EPC.
Szebeni et al., "Activation of complement by therapeutic liposomes and other lipid excipient-based therapeutic products: prediction and prevention," Adv. Drug Deliv. Rev. (2011) vol. 63, No. 12, pp. 1020-1030.
Szebeni, "Complement activation-related pseudoallergy: a stress reaction in blood triggered by nanomedicines and biologicals," Mol. Immunol.. (2014) vol. 61, No. 2, pp. 163-173.
Szebeni, J. and Storm, G., "Complement activation as a bioequivalence issue relevant to the development of generic liposomes and other nanoparticulate drugs," Biochem. Biophys. Res. Commun. (2015), vol. 468, No. 3, pp. 490-4977.
Tang et al. "Design of Freeze-Drying Processes for Pharmaceuticals: Practical Advice," Pharmaceutical Research (2004), vol. 21, No. 2, pp. 191-200.
Tannous et al., "Secreted blood reporters: Insights and applications," Biotechnol. Adv. (2011), vol. 29, No. 6, pp. 997-1003.
Tcherepanova et al., "Ectopic Expression of a Truncated CD40L Protein from Synthetic Post-Transcriptionally Capped RNA in Dendritic Cells Induces High Levels of IL-12 Secretion," BMC Molecular Biology (2008), vol. 9, No. 90, pp. 1-13.
Torchilin et al., "Poly(ethylene glycol) on the liposome surface: on the mechanism of polymer-coated liposome longevity," Biochimica et Biophysica Acta (1994), vol. 1195, pp. 11-20.
Tranchant et al., "Physiocochemical optimisation of plasmid delivery by cationic lipids," J. Gene Med. (2004), vol. 6, pp. S24-S35.

(56) References Cited

OTHER PUBLICATIONS

Tubulekas et al., "Alphavirus expression vectors and their use as recombinant vaccines: a minireview," Gene (1997), vol. 190, pp. 191-195.
Uddin, "Cationic lipids used in non-viral gene delivery systesm," Biotechnology and Molecular Biology Review (2007), vol. 2, No. 3, pp. 058-067.
Van Der Velden et al., "Vector Design for Optimal Protein Expression", Bio Techniques (Sep. 2001), vol. 31, pp. 572-282.
Van Winden, "Freeze-drying of liposomes: theory and practice "Methods Enzymol. (2003), vol. 367, pp. 99-110.
Varnum et al., "Identification of proteins in human cytomegalovirus (HCMV) particles: the HCMV proteome," J. Virol. (2004), vol. 78, No. 20, pp. 10960-10966.
VirTis Advantage Plus Benchtop Freeze Dryer, Specification Sheet 2013, www.SPScientific.com.
VirTis Advantage PlusPersonal Freeze Dryers, Marketing Brochure 2008, www.SPindustries.com.
Wang, D. and Shenk, T., "Human cytomegalovirus virion protein complex required for epithelial and endothelial cell tropism," Proc. Natl. Acad. Sci. USA (2005), vol. 102, No. 50, pp. 18153-18158.
Weissman et al., "HIV Gag mRNA Transfection of Dendritic Cells (DC) Delivers Encoded Antigen to MHC Class I and II Molecules, Causes DC Maturation, and Induces a Potent Human In Vitro Primary Immune Response," J. Immunol. (2000), vol. 165, No. 8, pp. 4710-4717.
Wille et al., "A human cytomegalovirus gO-null mutant fails to incorporate gH/gL into the virion envelope and is unable to enter fibroblasts and epithelial and endothelial cells," J. Virol. (2010), vol. 84, No. 5, pp. 2585-2596.
Willis et al., "Liposome-Anchored Vascular Endothelial Growth Factor Aptamers," Bioconjugate Chem. (1998), vol. 9, pp. 573-582.
Wisse et al., "The size of endothelial fenestrae in human liver sinudoids: implication for 'hepatocyte-directed gene transfer," Gene Therapy (2008), vol. 15, pp. 1193-1199.
Woodward et al., "Varicella Virus Vaccine Live: A 22-Year Review of Postmarketing Safety Data," Open Forum Infect. Dis. (2019), pp. 1-13.
Xu et al., "Physicochemical characterization and purification of cationic lipoplexes," Biophys J. (1999), vol. 77, No. 1, pp. 341-353.
Xu et al., "Sequential priming and boosting with heterologous HIV immunogens predominantly stimulated T cell immunity against conserved epitopes," AIDS (2006), vol. 20, No. 18, pp. 2293-2303.
Xu, et al., "Drug Delivery Trends in Clinical Trials and Translational Medicine: Challenges and Opportunities in the Delivery of Nucleic Acid-Based Therapeutics," J. Pharm. Sci. (2011), vol. 100, No. 1, pp. 38-52.
Xue et al., "Lipid-Based Nanocarriers for RNA Delivery," Curr. Pharm. Des. (2015), vol. 21, No. 22, pp. 3140-3147.
Yadava et al., "Effect of lyophilization and freeze-thawing on the stability of siRNA-liposome complexes," AAPS Pharm Sci Tech (2008), vol. 9. No. 2, pp. 335-341.
Yang et al., "Overcoming the inhibitory effect of serum on lipofection by increasing the charge ratio of cationic liposome to DNA," Gene Therapy (1997), vol. 4, pp. 950-960.
Yarian et al., "Structural and Functional Roles of the N1- and N3-Protons of ψ at tRNA's Position 39," Nucleic Acids Research (1999), vol. 27, No. 17, pp. 3542-3549.
Yu et al., "Effects of Moisture Content on the Storage Stability of Dried Lipoplex Formulations," Journal of Pharmaceutical Sciences (2009), vol. 98, No. 9, pp. 3278-3289.
Zhao et al., "N/P ratio significantly influences the transfection efficiency and cytotoxicity of a polyethylenimine/chitosan/DNA complex," Biol. Pharm. Bull. (2009), vol. 32, No. 4, pp. 706-710.
Zhu et al. "Vaccines for Gonorrhea: Can We Rise to the Challenge?" Frontiers in Microbiology (Jun. 2011), vol. 2, pp. 1-13.
Zhu et al., "Systemic Gene Expression After Intravenous DNA Delivery into Adult Mice," Science (1993), vol. 261, pp. 209-211.
Zhu, L. and Mahato, R. I., "Lipid and polymeric carrier-mediated nucleic acid delivery," Expert Opin Drug Deliv. (2010). vol. 7, No. 10, pp. 1209-1226.
Zimmer et al., "RNA Replicons—A New Approach for Influenza Virus Immunoprophylaxis," Viruses (2010), vol. 2, pp. 413-434.
Züst et al., "Ribose 2'-O-Methylation Provides a Molecular Signature for the Distinction of Self and Non-self mRNA Dependent on the RNA Sensor Mda5,"Nature Immunology (2011), vol. 12, No. 2. pp. 137-144.
"ProductInforNow,"Modern Drug Discovery, vol. 6, No. 6, (2003), pp. 57-62.
Akinc et al., "The Onpattro Story and the Clinical Translation of Nanomedicines Containing Nucleic Acid-Based Drugs," Nature Nanotechnology, vol. 14, (2019), pp. 1084-1087.
Ambegia et al., "Stabilized Plasmid-Lipid Particles Containing PEG-diacylglycerols Exhibit Extended Circulation Lifetimes and Tumor Selective Gene Expression," Biochimica el Biophysica Acta., vol. 1669, (2005), pp. 155-163.
Annex A, "Effects of Charge Ration on SAM-LNP Formulation and In Vitro Activity," by Russell Johnson, filed by proprietor on Nov. 19, 2018 in EP2729126 (EP 12738679.5). and filed on Sep. 23, 2021 as D26 in opposition in EP2729126 (EP 12738679.5).
Banerjee, "5'-Terminal Cap Structure in Eucaryotic Messenger Ribonucleic Acids," Microbiological Reviews, vol. 44, No. 2, (1989), pp. 175-205.
Bangs et al., "Mass Spectrometry of mRNA cap 4 from Trypanosomatids Reveals Two Novel Nucleosides," The Journal of Biological Chemistry, vol. 267, No. 14, (1992), pp. 9805-9815.
Cox et al., "Plasmid DNA and Messenger RNA for Therapy," Hanbook of Pharmaceutical Biotechnology, Chapter 7.2, (2007), pp. 971-1011.
Declaration of Kimberly J. Hassett, dated Nov. 18, 2021, filed on Nov. 26, 2021 in EP2506857 (EP 10835016.6).
Declaration of Prof. Liljestrom dated Dec. 11, 2018, submitted on Dec. 11, 2018 to the European Patent Office in the opposition proceedings concerning EP2590676 B1 (EP 11741348.4).
Declaration of Russell Johnson dated Sep. 21, 2022, filed during opposition on Sep. 23, 2022 in EP2591103 (EP 11736498.4), Int'l filing date Jul. 6, 2012, (2 pages).
Declaration of Russell Johnson dated Aug. 6, 2018, filed on Aug. 8, 2018 in EP 2 519 114 (EP 11736497.6).
Declaration of Russell Johnson dated Dec. 10, 2018, filed on Dec. 11, 2022 in EP 2 590 676 (EP 11741348.4).
Declaration of Russell Johnson dated May 6, 2021, filed on May 7, 2021 in EP 2 750 707 (EP 12769787.8).
Declaration with CV from Dr Olatokumbo Ogunleye Mar. 1, 2022, filed as D43 on Mar. 4, 2022 in EP3336082 (EP 18153312.6).
Excerpt from Moderna, Inc. (2018), Form 10-K, httpsL//www.annualreports.com/HostedData/AnnualReportArchive/m/NASDAQ_MRNA_2018.pdf.
Expert Opinion of Dr. Rolf Schubert, Jan. 8, 2018, filed as E30 on Jan. 12, 2018 in EP 2 590 626 B1 (EP 11736500.7).
Fechter et al., "Recognition of mRNA Cap Structures by Viral and Cellular Proteins," Journal of General Virology, vol. 86, (2005), pp. 1239-1249.
Furuichi et al., "Viral and Cellular mRNA Capping: Past and Prospects," Advances in Virus Research, vol. 55, (2000), pp. 135-184.
Hess et al., "Vaccination with mRNAs encoding Tumor-Associated Antigens and Granulocyte-Macrophage Colony-Stimulating Factor Efficiently Primes CTL Responses, but is Insufficient to Overcome Tolerance to a Model Tumor/Self Antigen," Cancer Immunol Immunother, vol. 55, (2006), pp. 672-683.
Kim et al., "Enhanced siRNA Delivery using Cationic Liposomes with new Polyarginine-Conjugated PEG-Lipid," International Journal of Pharmaceutics, vol. 392, (2010), pp. 141-147.
Lambert et al., "Intradermal Vaccine Delivery: Will New Delivery Systems Transform Vaccine Administration?" Vaccine, vol. 26, (2008), pp. 3197-3208.
Li et al., "Low-pH-Sensitive Poly(ethylene glycol) (PEG)-Stabilized Plasmid Nanolipoparticles: Effects of PEG Chain Length, Lipid Composition and Assembly Conditions on Gene Delivery," The Journal of Gene Medicine, vol. 7, (2005), pp. 67-79.

(56) References Cited

OTHER PUBLICATIONS

Morais et al., "The Critical Contribution of Pseuduouridine to mRNA COVID-19 Vaccines," Frontiers in Cell and Development Biology, vol. 9, (2021), pp. 1-9.
Pardi et al., "Nucleoside-Modified mRNA Vaccines Induce Potent T Follicular Helper and Germinal Center B Cell Responses," Journal of Experimental Medicine, vol. 215, No. 6, (2018), pp. 1571-1586.
Pascolo, "Vaccination with Messenger RNA (mRNA)," Handboook of Experimental Pharmacology, vol. 183, (2008), pp. 221-235.
Patentee Submission to EPO in EP Application No. 11758014.2, dated Nov. 13, 2016.
Post-filed evidence *Annes A* submitted with response filed on Jun. 12, 2014 during prosecution of EP2578685 B1 (EP Appl. No. 12008048.6) (D1a).
Post-filing experimental evidence submitted by the Patentee during the examination phase of EP 18 153 312.6 on Apr. 5, 2019.
Print-out of the entry for the m7G(5')ppp(5')G RNA Cap Structure Analog from the New England Biolabs homepage, from Apr. 2010, pp. 1-2, (web.archive.org/web/20100420121944/http://www.neb.com/nebecomm/products/productS 1404.asp).
Print-out of the entry for the ScriptCap™ m7G Capping System Analog from the Epicentre Biotechnologies homepage from Nov. 2006, pp. 1-2. (https://web.archive.org/web/20061116032247/http://www.epibio.com/item.asp?ID=498&Cati0=26).
Roos, "European Approves Sanofi's Intradermal Flu Vaccine," University of Minnesota Center for Infections Disease Research and Policy [online:cidrap.umn.edu/news-perspective/2009/02/europe-approves-sanofis-intradermal-flu-vaccine], (2009), pp. 1-2.
Santos et al., "Design of Peptide-Targeted Liposomes Containing Nucleic Acids," Biochimica et Biophysica Acta, vol. 1796, (2010), pp. 433-441.
Sonoke et al., "Tumor Regression in Mice by Delivery of Bcl-2 Small Interfering RNA with Pegylated/Cationic Liposomes," Cancer Research, vol. 68, (2008), pp. 8843-8851.
Spikevax Patient Information, European Medicines Agency, (2002), pp. 1-5.
Sticchi et al., "The Intradermal Vaccination: Past Experiences and Current Perspectives," J Prev Med Hyg, vol. 51, (2010), pp. 7-14.
Van Den Berg et al., "Shielding the Cationic Charge of Nanoparticle-Formulated Dermal DNA Vaccines is Essential for Antigen Expression and Immunogenicity,"Journal of Controlled Release, vol. 141, (2010), pp. 234-240.
U.S. Office Action for U.S. Appl. No. 17/512,258, dated Jan. 20, 2023.
U.S. Office Action for U.S. Appl. No. 17/696,143, dated Jan. 24, 2023.
CV Dr Olatokumbo Ogunleye, submitted on Mar. 4, 2022.
Declaration by Russell Johnson dated Sep. 21, 2022 in opposition filed in EP2591103, Int'l filed Jul. 6, 2012, (2 pages).
Declaration entitled "Annex A" by Russell Johnson cited in EP2729126 in opposition filed Sep. 23, 2021 (4 pages).
Declaration from Dr Olatokumbo Ogunleye, dated Mar. 1, 2022.
Declaration of Russell N. Johnson dated Dec. 10, 2018.
Johnson signed Declaration dated Oct. 22, 2020 (9 pages).
Opposition Document D60—Declaration of Russell N. Johnson, dated Aug. 6, 2018, from EP2591114, European Equivalent of U.S. Appl. No. 13/808,153, filed Aug. 8, 2018.
Russell Johnson Declaration dated May 6, 2021, filed in Opposition proceeding in EP2750707.
Geall, U.S. Appl. No. 17/808,519, filed Jun. 23, 2022.
Noe, V., et al., "mRNA technologies Insight Report," European Patent Office, Oct. 2023, pp. 1-35.

* cited by examiner

SEQUENCE LISTING

<160> NUMBER OF SEQ ID NOS: 26

<210> SEQ ID NO 1

<211> LENGTH: 2727
<212> TYPE: DNA
<213> ORGANISM: Cytomegalovirus

<400> SEQUENCE: 1
atggaaagcc ggatctggtg cctggtcgtg tgcgtgaacc tgtgcatcgt gtgcctggga 60
gccgccgtga gcagcagcag caccagaggc accagcgcca cacacagcca ccacagcagc 120
cacaccacct ctgccgccca cagcagatcc ggcagcgtgt cccagagagt gaccagcagc 180
cagaccgtgt cccacggcgt gaacgagaca atctacaaca ccaccctgaa gtacggcgac 240
gtcgtgggcg tgaataccac caagtacccc tacagagtgt gcagcatggc ccagggcacc 300
gacctgatca gattcgagcg gaacatcgtg tgcaccagca tgaagcccat caacgaggac 360
ctggacgagg gcatcatggt ggtgtacaag agaaacatcg tggcccacac cttcaaagtg 420
cgggtgtacc agaaggtgct gaccttccgg cggagctacg cctacatcca caccacatac 480
ctgctgggca gcaacaccga gtacgtggcc cctcccatgt gggagatcca ccacatcaac 540
agccacagcc agtgctacag cagctacagc cgcgtgatcg ccggcacagt gttcgtggcc 600
taccaccggg acagctacga gaacaagacc atgcagctga tgcccgacga ctacagcaac 660
acccacagca ccagatacgt gaccgtgaag gaccagtggc acagcagagg cagcacctgg 720
ctgtaccggg agacatgcaa cctgaactgc atggtcacca tcaccaccgc cagaagcaag 780 taccccttacc acttcttcgc cacctccacc ggcgacgtgg tggacatcag cccccttctac 840 aacggcacca accggaacgc cagctacttc ggcgagaacg ccgacaagtt cttcatcttc 900
cccaactaca ccatcgtgtc cgacttcggc agacccaaca gcgctctgga aacccacaga 960
ctggtggcct ttctggaacg ggccgacagc gtgatcagct gggacatcca ggacgagaag 1020
aacgtgacct gccagctgac cttctgggag gcctctgaga gaaccatcag aagcgaggcc 1080
gaggacagct accacttcag cagcgccaag atgaccgcca ccttcctgag caagaaacag 1140
gaagtgaaca tgagcgactc cgccctggac tgcgtgaggg acgaggccat caacaagctg 1200
cagcagatct tcaacaccag ctacaaccag acctacgaga agtatggcaa tgtgtccgtg 1260
ttcgagacaa caggcggcct ggtggtgttc tggcagggca tcaagcagaa aagcctggtg 1320
gagctggaac ggctcgccaa ccggtccagc ctgaacctga cccacaaccg gaccaagcgg 1380
agcaccgacg gcaacaacgc aacccacctg tccaacatgg aaagcgtgca caacctggtg 1440
tacgcacagc tgcagttcac ctacgacacc ctgcggggct acatcaacag agccctggcc 1500
cagatcgccg aggcttggtg cgtggaccag cggcggaccc tggaagtgtt caaagagctg 1560
tccaagatca accccagcgc catcctgagc gccatctaca acaagcctat cgccgccaga 1620
ttcatgggcg acgtgctggg cctggccagc tgcgtgacca tcaaccagac cagcgtgaag 1680
gtgctgcggg acatgaacgt gaaagagagc ccaggccgct gctactccag acccgtggtc 1740
atcttcaact tcgccaacag ctcctacgtg cagtacggcc agctgggcga ggacaacgag 1800
atcctgctgg ggaaccaccg gaccgaggaa tgccagctgc ccagcctgaa gatctttatc 1860
gccggcaaca gcgcctacga gtatgtggac tacctgttca agcggatgat cgacctgagc 1920
agcatctcca ccgtggacag catgatcgcc ctggacatcg accccctgga aaacaccgac 1980
ttccgggtgc tggaactgta cagccagaaa gagctgcgga gcagcaacgt gttcgacctg 2040
gaagagatca tgcgggagtt caacagctac aagcagcgcg tgaaatacgt ggaggacaag 2100
gtggtggacc ccctgcctcc ttacctgaag ggcctggacg acctgatgag cggactgggc 2160
gctgccggaa aagccgtggg agtggccatt ggagctgtgg gcggagctgt ggcctctgtc 2220

-continued gtggaaggcg tcgccacctt tctgaagaac cccttcggcg ccttcaccat catcctggtg 2280
gccattgccg tcgtgatcat cacctacctg atctacaccc ggcagcggag actgtgtacc 2340
cagcccctgc agaacctgtt cccctacctg gtgtccgccg atggcaccac agtgaccagc 2400
ggctccacca aggataccag cctgcaggcc ccacccagct acgaagagag cgtgtacaac 2460
agcggcagaa agggccctgg ccctcccagc tctgatgcca gcacagccgc ccctccctac 2520
accaacgagc aggcctacca gatgctgctg gccctggcta gactggatgc cgagcagagg 2580
gcccagcaga acggcaccga cagcctggat ggcagaaccg gcacccagga caagggccag 2640
aagcccaacc tgctggaccg gctgcggcac cggaagaacg gctaccggca cctgaaggac 2700
agcgacgagg aagagaacgt ctgataa 2727

<210> SEQ ID NO 2
<211> LENGTH: 907
<212> TYPE: PRT
<213> ORGANISM: Cytomegalovirus

<400> SEQUENCE: 2

Met Glu Ser Arg Ile Trp Cys Leu Val Val Cys Val Asn Leu Cys Ile
1 5 10 15

Val Cys Leu Gly Ala Ala Val Ser Ser Ser Ser Thr Arg Gly Thr Ser
20 25 30

Ala Thr His Ser His His Ser Ser His Thr Thr Ser Ala Ala His Ser
35 40 45

Arg Ser Gly Ser Val Ser Gln Arg Val Thr Ser Ser Gln Thr Val Ser
50 55 60

His Gly Val Asn Glu Thr Ile Tyr Asn Thr Thr Leu Lys Tyr Gly Asp
65 70 75 80

Val Val Gly Val Asn Thr Thr Lys Tyr Pro Tyr Arg Val Cys Ser Met
85 90 95

Ala Gln Gly Thr Asp Leu Ile Arg Phe Glu Arg Asn Ile Val Cys Thr
100 105 110

Ser Met Lys Pro Ile Asn Glu Asp Leu Asp Glu Gly Ile Met Val Val
115 120 125

Tyr Lys Arg Asn Ile Val Ala His Thr Phe Lys Val Arg Val Tyr Gln
130 135 140

Lys Val Leu Thr Phe Arg Arg Ser Tyr Ala Tyr Ile His Thr Thr Tyr
145 150 155 160

Leu Leu Gly Ser Asn Thr Glu Tyr Val Ala Pro Pro Met Trp Glu Ile
165 170 175

His His Ile Asn Ser His Ser Gln Cys Tyr Ser Ser Tyr Ser Arg Val
180 185 190

Ile Ala Gly Thr Val Phe Val Ala Tyr His Arg Asp Ser Tyr Glu Asn
195 200 205

Lys Thr Met Gln Leu Met Pro Asp Asp Tyr Ser Asn Thr His Ser Thr
210 215 220

Arg Tyr Val Thr Val Lys Asp Gln Trp His Ser Arg Gly Ser Thr Trp
225 230 235 240

Leu Tyr Arg Glu Thr Cys Asn Leu Asn Cys Met Val Thr Ile Thr Thr
245 250 255

Ala Arg Ser Lys Tyr Pro Tyr His Phe Phe Ala Thr Ser Thr Gly Asp
260 265 270

Val Val Asp Ile Ser Pro Phe Tyr Asn Gly Thr Asn Arg Asn Ala Ser

-continued

```
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln Arg Val Lys Tyr Val Glu Asp Lys Val Val Asp Pro
    690                 695                 700
```

```
Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
            740                 745                 750

Gly Ala Phe Thr Ile Ile Leu Val Ala Ile Ala Val Val Ile Ile Thr
        755                 760                 765

Tyr Leu Ile Tyr Thr Arg Gln Arg Arg Leu Cys Thr Gln Pro Leu Gln
    770                 775                 780

Asn Leu Phe Pro Tyr Leu Val Ser Ala Asp Gly Thr Thr Val Thr Ser
785                 790                 795                 800

Gly Ser Thr Lys Asp Thr Ser Leu Gln Ala Pro Pro Ser Tyr Glu Glu
                805                 810                 815

Ser Val Tyr Asn Ser Gly Arg Lys Gly Pro Gly Pro Pro Ser Ser Asp
            820                 825                 830

Ala Ser Thr Ala Ala Pro Pro Tyr Thr Asn Glu Gln Ala Tyr Gln Met
        835                 840                 845

Leu Leu Ala Leu Ala Arg Leu Asp Ala Glu Gln Arg Ala Gln Gln Asn
    850                 855                 860

Gly Thr Asp Ser Leu Asp Gly Arg Thr Gly Thr Gln Asp Lys Gly Gln
865                 870                 875                 880

Lys Pro Asn Leu Leu Asp Arg Leu Arg His Arg Lys Asn Gly Tyr Arg
                885                 890                 895

His Leu Lys Asp Ser Asp Glu Glu Glu Asn Val
            900                 905
```

<210> SEQ ID NO 3
<211> LENGTH: 2256
<212> TYPE: DNA
<213> ORGANISM: Cytomegalovirus

<400> SEQUENCE: 3

```
atggaaagcc ggatctggtg cctggtcgtg tgcgtgaacc tgtgcatcgt gtgcctggga     60

gccgccgtga gcagcagcag caccagaggc accagcgcca cacacagcca ccacagcagc    120

cacaccacct ctgccgccca cagcagatcc ggcagcgtgt cccagagagt gaccagcagc    180

cagaccgtgt cccacggcgt gaacgagaca atctacaaca ccaccctgaa gtacggcgac    240

gtcgtgggcg tgaataccac caagtacccc tacagagtgt gcagcatggc ccagggcacc    300

gacctgatca gattcgagcg gaacatcgtg tgcaccagca tgaagcccat caacgaggac    360

ctggacgagg gcatcatggt ggtgtacaag agaaacatcg tggcccacac cttcaaagtg    420

cgggtgtacc agaaggtgct gaccttccgg cggagctacg cctacatcca caccacatac    480

ctgctgggca gcaacaccga gtacgtggcc cctcccatgt gggagatcca ccacatcaac    540

agccacagcc agtgctacag cagctacagc cgcgtgatcg ccggcacagt gttcgtggcc    600

taccaccggg acagctacga gaacaagacc atgcagctga tgcccgacga ctacagcaac    660

acccacagca ccagatacgt gaccgtgaag gaccagtggc acagcagagg cagcacctgg    720

ctgtaccggg agacatgcaa cctgaactgc atggtcacca tcaccaccgc cagaagcaag    780

taccccttacc acttcttcgc cacctccacc ggcgacgtgg tggacatcag ccccttctac    840

aacggcacca accggaacgc cagctacttc ggcgagaacg ccgacaagtt cttcatcttc    900

cccaactaca ccatcgtgtc cgacttcggc agacccaaca gcgctctgga aacccacaga    960
```

-continued

```
ctggtggcct ttctggaacg ggccgacagc gtgatcagct gggacatcca ggacgagaag   1020

aacgtgacct gccagctgac cttctgggag gcctctgaga gaaccatcag aagcgaggcc   1080

gaggacagct accacttcag cagcgccaag atgaccgcca ccttcctgag caagaaacag   1140

gaagtgaaca tgagcgactc cgccctggac tgcgtgaggg acgaggccat caacaagctg   1200

cagcagatct tcaacaccag ctacaaccag acctacgaga agtatggcaa tgtgtccgtg   1260

ttcgagacaa caggcggcct ggtggtgttc tggcagggca tcaagcagaa aagcctggtg   1320

gagctggaac ggctcgccaa ccggtccagc ctgaacctga cccacaaccg gaccaagcgg   1380

agcaccgacg gcaacaacgc aacccacctg tccaacatgg aaagcgtgca caacctggtg   1440

tacgcacagc tgcagttcac ctacgacacc ctgcggggct acatcaacag agccctggcc   1500

cagatcgccg aggcttggtg cgtggaccag cggcggaccc tggaagtgtt caaagagctg   1560

tccaagatca accccagcgc catcctgagc gccatctaca acaagcctat cgccgccaga   1620

ttcatgggcg acgtgctggg cctggccagc tgcgtgacca tcaaccagac cagcgtgaag   1680

gtgctgcggg acatgaacgt gaaagagagc ccaggccgct gctactccag acccgtggtc   1740

atcttcaact tcgccaacag ctcctacgtg cagtacggcc agctgggcga ggacaacgag   1800

atcctgctgg ggaaccaccg gaccgaggaa tgccagctgc ccagcctgaa gatctttatc   1860

gccggcaaca gcgcctacga gtatgtggac tacctgttca agcggatgat cgacctgagc   1920

agcatctcca ccgtggacag catgatcgcc ctggacatcg accccctgga aaacaccgac   1980

ttccgggtgc tggaactgta cagccagaaa gagctgcgga gcagcaacgt gttcgacctg   2040

gaagagatca tgcgggagtt caacagctac aagcagcgcg tgaaatacgt ggaggacaag   2100

gtggtggacc ccctgcctcc ttacctgaag ggcctggacg acctgatgag cggactgggc   2160

gctgccggaa aagccgtggg agtggccatt ggagctgtgg gcggagctgt ggcctctgtc   2220

gtggaaggcg tcgccacctt tctgaagaac tgataa                             2256
```

<210> SEQ ID NO 4
<211> LENGTH: 750
<212> TYPE: PRT
<213> ORGANISM: Cytomegalovirus

<400> SEQUENCE: 4

```
Met Glu Ser Arg Ile Trp Cys Leu Val Val Cys Val Asn Leu Cys Ile
1               5                   10                  15

Val Cys Leu Gly Ala Ala Val Ser Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140
```

```
Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560
```

-continued

```
Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln Arg Val Lys Tyr Val Glu Asp Lys Val Val Asp Pro
    690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn
            740                 745                 750
```

<210> SEQ ID NO 5
<211> LENGTH: 2082
<212> TYPE: DNA
<213> ORGANISM: Cytomegalovirus

<400> SEQUENCE: 5

```
atggaaagcc ggatctggtg cctggtcgtg tgcgtgaacc tgtgcatcgt gtgcctggga     60

gccgccgtga gcagcagcag caccagaggc accagcgcca cacacagcca ccacagcagc    120

cacaccacct ctgccgccca cagcagatcc ggcagcgtgt cccagagagt gaccagcagc    180

cagaccgtgt cccacggcgt gaacgagaca atctacaaca ccaccctgaa gtacggcgac    240

gtcgtgggcg tgaataccac caagtacccc tacagagtgt gcagcatggc ccagggcacc    300

gacctgatca gattcgagcg gaacatcgtg tgcaccagca tgaagcccat caacgaggac    360

ctggacgagg gcatcatggt ggtgtacaag agaaacatcg tggcccacac cttcaaagtg    420

cgggtgtacc agaaggtgct gaccttccgg cggagctacg cctacatcca caccacatac    480

ctgctgggca gcaacaccga gtacgtggcc cctcccatgt gggagatcca ccacatcaac    540

agccacagcc agtgctacag cagctacagc cgcgtgatcg ccggcacagt gttcgtggcc    600

taccaccggg acagctacga gaacaagacc atgcagctga tgcccgacga ctacagcaac    660

acccacagca ccagatacgt gaccgtgaag gaccagtggc acagcagagg cagcacctgg    720

ctgtaccggg agacatgcaa cctgaactgc atggtcacca tcaccaccgc cagaagcaag    780

taccccttacc acttcttcgc cacctccacc ggcgacgtgg tggacatcag ccccttctac    840

aacggcacca accggaacgc cagctacttc ggcgagaacg ccgacaagtt cttcatcttc    900

cccaactaca ccatcgtgtc cgacttcggc agacccaaca gcgctctgga aacccacaga    960

ctggtggcct ttctggaacg ggccgacagc gtgatcagct gggacatcca ggacgagaag   1020

aacgtgacct gccagctgac cttctgggag gcctctgaga gaaccatcag aagcgaggcc   1080
```

```
gaggacagct accacttcag cagcgccaag atgaccgcca ccttcctgag caagaaacag   1140

gaagtgaaca tgagcgactc cgccctggac tgcgtgaggg acgaggccat caacaagctg   1200

cagcagatct tcaacaccag ctacaaccag acctacgaga agtatggcaa tgtgtccgtg   1260

ttcgagacaa caggcggcct ggtggtgttc tggcagggca tcaagcagaa aagcctggtg   1320

gagctggaac ggctcgccaa ccggtccagc ctgaacctga cccacaaccg gaccaagcgg   1380

agcaccgacg gcaacaacgc aacccacctg tccaacatgg aaagcgtgca caacctggtg   1440

tacgcacagc tgcagttcac ctacgacacc ctgcggggct acatcaacag agccctggcc   1500

cagatcgccg aggcttggtg cgtggaccag cggcggaccc tggaagtgtt caaagagctg   1560

tccaagatca accccagcgc catcctgagc gccatctaca acaagcctat cgccgccaga   1620

ttcatgggcg acgtgctggg cctggccagc tgcgtgacca tcaaccagac cagcgtgaag   1680

gtgctgcggg acatgaacgt gaaagagagc ccaggccgct gctactccag acccgtggtc   1740

atcttcaact tcgccaacag ctcctacgtg cagtacggcc agctgggcga ggacaacgag   1800

atcctgctgg ggaaccaccg gaccgaggaa tgccagctgc ccagcctgaa gatctttatc   1860

gccggcaaca gcgcctacga gtatgtggac tacctgttca agcggatgat cgacctgagc   1920

agcatctcca ccgtggacag catgatcgcc ctggacatcg accccctgga aaacaccgac   1980

ttccgggtgc tggaactgta cagccagaaa gagctgcgga gcagcaacgt gttcgacctg   2040

gaagagatca tgcgggagtt caacagctac aagcagtgat aa                      2082
```

<210> SEQ ID NO 6
<211> LENGTH: 692
<212> TYPE: PRT
<213> ORGANISM: Cytomegalovirus

<400> SEQUENCE: 6

```
Met Glu Ser Arg Ile Trp Cys Leu Val Val Cys Val Asn Leu Cys Ile
1               5                   10                  15

Val Cys Leu Gly Ala Ala Val Ser Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190
```

-continued

```
Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
```

-continued

```
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln
    690


<210> SEQ ID NO 7
<211> LENGTH: 2232
<212> TYPE: DNA
<213> ORGANISM: Cytomegalovirus

<400> SEQUENCE: 7

atgaggcctg gcctgccctc ctacctgatc atcctggccg tgtgcctgtt cagccacctg      60

ctgtccagca gatacggcgc cgaggccgtg agcgagcccc tggacaaggc tttccacctg     120

ctgctgaaca cctacggcag acccatccgg tttctgcggg agaacaccac ccagtgcacc     180

tacaacagca gcctgcggaa cagcaccgtc gtgagagaga acgccatcag cttcaacttt     240

ttccagagct acaaccagta ctacgtgttc cacatgccca gatgcctgtt tgccggccct     300

ctggccgagc agttcctgaa ccaggtggac ctgaccgaga cactggaaag ataccagcag     360

cggctgaata cctacgccct ggtgtccaag gacctggcca gctaccggtc ctttagccag     420

cagctcaagg ctcaggatag cctcggcgag cagcctacca ccgtgccccc tcccatcgac     480

ctgagcatcc cccacgtgtg gatgcctccc cagaccaccc ctcacggctg gaccgagagc     540

cacaccacct ccggcctgca cagaccccac ttcaaccaga cctgcatcct gttcgacggc     600

cacgacctgc tgtttagcac cgtgaccccc tgcctgcacc agggcttcta cctgatcgac     660

gagctgagat acgtgaagat caccctgacc gaggatttct tcgtggtcac cgtgtccatc     720

gacgacgaca cccccatgct gctgatcttc ggccacctgc ccagagtgct gttcaaggcc     780

ccctaccagc gggacaactt catcctgcgg cagaccgaga agcacgagct gctggtgctg     840

gtcaagaagg accagctgaa ccggcactcc tacctgaagg accccgactt cctggacgcc     900

gccctggact tcaactacct ggacctgagc gccctgctga gaaacagctt ccacagatac     960

gccgtggacg tgctgaagtc cggacggtgc cagatgctcg atcggcggac cgtggagatg    1020

gccttcgcct atgccctcgc cctgttcgcc gctgccagac aggaagaggc tggcgcccag    1080

gtgtcagtgc ccagagccct ggatagacag gccgccctgc tgcagatcca ggaattcatg    1140

atcacctgcc tgagccagac cccccctaga accaccctgc tgctgtaccc cacagccgtg    1200

gatctggcca agagggccct gtggaccccc aaccagatca ccgacatcac aagcctcgtg    1260

cggctcgtgt acatcctgag caagcagaac cagcagcacc tgatccccca gtgggccctg    1320

agacagatcg ccgacttcgc cctgaagctg cacaagaccc atctggccag ctttctgagc    1380

gccttcgcca ggcaggaact gtacctgatg ggcagcctgg tccacagcat gctggtgcat    1440

accaccgagc ggcgggagat cttcatcgtg gagacaggcc tgtgtagcct ggccgagctg    1500

tcccacttta cccagctgct ggcccaccct caccacgagt acctgagcga cctgtacacc    1560

ccctgcagca gcagcggcag acgggaccac agcctggaac ggctgaccag actgttcccc    1620
```

gatgccaccg tgcctgctac agtgcctgcc gccctgtcca tcctgtccac catgcagccc 1680
agcaccctgg aaaccttccc cgacctgttc tgcctgcccc tgggcgagag ctttagcgcc 1740
ctgaccgtgt ccgagcacgt gtcctacatc gtgaccaatc agtacctgat caagggcatc 1800
agctaccccg tgtccaccac agtcgtgggc cagagcctga tcatcaccca gaccgacagc 1860
cagaccaagt gcgagctgac ccggaacatg cacaccacac acagcatcac cgtggccctg 1920
aacatcagcc tggaaaactg cgctttctgt cagtctgccc tgctggaata cgacgatacc 1980
cagggcgtga tcaacatcat gtacatgcac gacagcgacg acgtgctgtt cgccctggac 2040
ccctacaacg aggtggtggt gtccagcccc cggacccact acctgatgct gctgaagaac 2100
ggcaccgtgc tggaagtgac cgacgtggtg gtggacgcca ccgacagcag actgctgatg 2160
atgagcgtgt acgccctgag cgccatcatc ggcatctacc tgctgtaccg gatgctgaaa 2220
acctgctgat aa 2232

<210> SEQ ID NO 8
<211> LENGTH: 742
<212> TYPE: PRT
<213> ORGANISM: Cytomegalovirus

<400> SEQUENCE: 8

Met Arg Pro Gly Leu Pro Ser Tyr Leu Ile Ile Leu Ala Val Cys Leu
1 5 10 15

Phe Ser His Leu Leu Ser Ser Arg Tyr Gly Ala Glu Ala Val Ser Glu
20 25 30

Pro Leu Asp Lys Ala Phe His Leu Leu Leu Asn Thr Tyr Gly Arg Pro
35 40 45

Ile Arg Phe Leu Arg Glu Asn Thr Thr Gln Cys Thr Tyr Asn Ser Ser
50 55 60

Leu Arg Asn Ser Thr Val Val Arg Glu Asn Ala Ile Ser Phe Asn Phe
65 70 75 80

Phe Gln Ser Tyr Asn Gln Tyr Tyr Val Phe His Met Pro Arg Cys Leu
85 90 95

Phe Ala Gly Pro Leu Ala Glu Gln Phe Leu Asn Gln Val Asp Leu Thr
100 105 110

Glu Thr Leu Glu Arg Tyr Gln Gln Arg Leu Asn Thr Tyr Ala Leu Val
115 120 125

Ser Lys Asp Leu Ala Ser Tyr Arg Ser Phe Ser Gln Gln Leu Lys Ala
130 135 140

Gln Asp Ser Leu Gly Glu Gln Pro Thr Thr Val Pro Pro Pro Ile Asp
145 150 155 160

Leu Ser Ile Pro His Val Trp Met Pro Pro Gln Thr Thr Pro His Gly
165 170 175

Trp Thr Glu Ser His Thr Thr Ser Gly Leu His Arg Pro His Phe Asn
180 185 190

Gln Thr Cys Ile Leu Phe Asp Gly His Asp Leu Leu Phe Ser Thr Val
195 200 205

Thr Pro Cys Leu His Gln Gly Phe Tyr Leu Ile Asp Glu Leu Arg Tyr
210 215 220

Val Lys Ile Thr Leu Thr Glu Asp Phe Phe Val Val Thr Val Ser Ile
225 230 235 240

Asp Asp Asp Thr Pro Met Leu Leu Ile Phe Gly His Leu Pro Arg Val
245 250 255

Leu Phe Lys Ala Pro Tyr Gln Arg Asp Asn Phe Ile Leu Arg Gln Thr

-continued

```
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
    370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
        435                 440                 445

Lys Leu His Lys Thr His Leu Ala Ser Phe Leu Ser Ala Phe Ala Arg
    450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Ser Gly Arg Arg
        515                 520                 525

Asp His Ser Leu Glu Arg Leu Thr Arg Leu Phe Pro Asp Ala Thr Val
    530                 535                 540

Pro Ala Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Ile Val Thr
            580                 585                 590

Asn Gln Tyr Leu Ile Lys Gly Ile Ser Tyr Pro Val Ser Thr Thr Val
        595                 600                 605

Val Gly Gln Ser Leu Ile Ile Thr Gln Thr Asp Ser Gln Thr Lys Cys
    610                 615                 620

Glu Leu Thr Arg Asn Met His Thr Thr His Ser Ile Thr Val Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
            660                 665                 670

Asp Asp Val Leu Phe Ala Leu Asp Pro Tyr Asn Glu Val Val Val Ser
        675                 680                 685
```

```
Ser Pro Arg Thr His Tyr Leu Met Leu Leu Lys Asn Gly Thr Val Leu
    690                 695                 700

Glu Val Thr Asp Val Val Val Asp Ala Thr Asp Ser Arg Leu Leu Met
705                 710                 715                 720

Met Ser Val Tyr Ala Leu Ser Ala Ile Ile Gly Ile Tyr Leu Leu Tyr
                725                 730                 735

Arg Met Leu Lys Thr Cys
            740


<210> SEQ ID NO 9
<211> LENGTH: 2151
<212> TYPE: DNA
<213> ORGANISM: Cytomegalovirus

<400> SEQUENCE: 9

atgaggcctg gcctgccctc ctacctgatc atcctggccg tgtgcctgtt cagccacctg     60

ctgtccagca gatacggcgc cgaggccgtg agcgagcccc tggacaaggc tttccacctg    120

ctgctgaaca cctacggcag acccatccgg tttctgcggg agaacaccac ccagtgcacc    180

tacaacagca gcctgcggaa cagcaccgtc gtgagagaga acgccatcag cttcaacttt    240

ttccagagct acaaccagta ctacgtgttc cacatgccca gatgcctgtt tgccggccct    300

ctggccgagc agttcctgaa ccaggtggac ctgaccgaga cactggaaag ataccagcag    360

cggctgaata cctacgccct ggtgtccaag gacctggcca gctaccggtc ctttagccag    420

cagctcaagg ctcaggatag cctcggcgag cagcctacca ccgtgccccc tcccatcgac    480

ctgagcatcc cccacgtgtg gatgcctccc cagaccaccc ctcacggctg gaccgagagc    540

cacaccacct ccggcctgca cagaccccac ttcaaccaga cctgcatcct gttcgacggc    600

cacgacctgc tgtttagcac cgtgaccccc tgcctgcacc agggcttcta cctgatcgac    660

gagctgagat acgtgaagat caccctgacc gaggatttct tcgtggtcac cgtgtccatc    720

gacgacgaca cccccatgct gctgatcttc ggccacctgc ccagagtgct gttcaaggcc    780

ccctaccagc gggacaactt catcctgcgg cagaccgaga agcacgagct gctggtgctg    840

gtcaagaagg accagctgaa ccggcactcc tacctgaagg accccgactt cctggacgcc    900

gccctggact tcaactacct ggacctgagc gccctgctga gaaacagctt ccacagatac    960

gccgtggacg tgctgaagtc cggacggtgc cagatgctcg atcggcggac cgtggagatg   1020

gccttcgcct atgccctcgc cctgttcgcc gctgccagac aggaagaggc tggcgcccag   1080

gtgtcagtgc ccagagccct ggatagacag gccgccctgc tgcagatcca ggaattcatg   1140

atcacctgcc tgagccagac cccccctaga accaccctgc tgctgtaccc cacagccgtg   1200

gatctggcca agagggccct gtggaccccc aaccagatca ccgacatcac aagcctcgtg   1260

cggctcgtgt acatcctgag caagcagaac cagcagcacc tgatccccca gtgggccctg   1320

agacagatcg ccgacttcgc cctgaagctg cacaagaccc atctggccag ctttctgagc   1380

gccttcgcca ggcaggaact gtacctgatg ggcagcctgg tccacagcat gctggtgcat   1440

accaccgagc ggcgggagat cttcatcgtg gagacaggcc tgtgtagcct ggccgagctg   1500

tcccacttta cccagctgct ggcccaccct caccacgagt acctgagcga cctgtacacc   1560

ccctgcagca gcagcggcag acgggaccac agcctggaac ggctgaccag actgttcccc   1620

gatgccaccg tgcctgctac agtgcctgcc gccctgtcca tcctgtccac catgcagccc   1680

agcaccctgg aaaccttccc cgacctgttc tgcctgcccc tgggcgagag ctttagcgcc   1740
```

```
ctgaccgtgt ccgagcacgt gtcctacatc gtgaccaatc agtacctgat caagggcatc   1800

agctaccccg tgtccaccac agtcgtgggc cagagcctga tcatcaccca gaccgacagc   1860

cagaccaagt gcgagctgac ccggaacatg cacaccacac acagcatcac cgtggccctg   1920

aacatcagcc tggaaaactg cgctttctgt cagtctgccc tgctggaata cgacgatacc   1980

cagggcgtga tcaacatcat gtacatgcac gacagcgacg acgtgctgtt cgccctggac   2040

ccctacaacg aggtggtggt gtccagcccc cggacccact acctgatgct gctgaagaac   2100

ggcaccgtgc tggaagtgac cgacgtggtg gtggacgcca ccgactgata a            2151


<210> SEQ ID NO 10
<211> LENGTH: 715
<212> TYPE: PRT
<213> ORGANISM: Cytomegalovirus

<400> SEQUENCE: 10

Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
            20                  25                  30

Pro Leu Asp Lys Ala Phe His Leu Leu Leu Asn Thr Tyr Gly Arg Pro
        35                  40                  45

Ile Arg Phe Leu Arg Glu Asn Thr Thr Gln Cys Thr Tyr Asn Ser Ser
    50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
        115                 120                 125

Ser Lys Asp Leu Ala Ser Tyr Arg Ser Phe Ser Gln Gln Leu Lys Ala
    130                 135                 140

Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
    290                 295                 300
```

Asn Tyr Leu Asp Leu Ser Ala Leu Leu Arg Asn Ser Phe His Arg Tyr
305 310 315 320

Ala Val Asp Val Leu Lys Ser Gly Arg Cys Gln Met Leu Asp Arg Arg
325 330 335

Thr Val Glu Met Ala Phe Ala Tyr Ala Leu Ala Leu Phe Ala Ala Ala
340 345 350

Arg Gln Glu Glu Ala Gly Ala Gln Val Ser Val Pro Arg Ala Leu Asp
355 360 365

Arg Gln Ala Ala Leu Leu Gln Ile Gln Glu Phe Met Ile Thr Cys Leu
370 375 380

Ser Gln Thr Pro Pro Arg Thr Thr Leu Leu Leu Tyr Pro Thr Ala Val
385 390 395 400

Asp Leu Ala Lys Arg Ala Leu Trp Thr Pro Asn Gln Ile Thr Asp Ile
405 410 415

Thr Ser Leu Val Arg Leu Val Tyr Ile Leu Ser Lys Gln Asn Gln Gln
420 425 430

His Leu Ile Pro Gln Trp Ala Leu Arg Gln Ile Ala Asp Phe Ala Leu
435 440 445

Lys Leu His Lys Thr His Leu Ala Ser Phe Leu Ser Ala Phe Ala Arg
450 455 460

Gln Glu Leu Tyr Leu Met Gly Ser Leu Val His Ser Met Leu Val His
465 470 475 480

Thr Thr Glu Arg Arg Glu Ile Phe Ile Val Glu Thr Gly Leu Cys Ser
485 490 495

Leu Ala Glu Leu Ser His Phe Thr Gln Leu Leu Ala His Pro His His
500 505 510

Glu Tyr Leu Ser Asp Leu Tyr Thr Pro Cys Ser Ser Ser Gly Arg Arg
515 520 525

Asp His Ser Leu Glu Arg Leu Thr Arg Leu Phe Pro Asp Ala Thr Val
530 535 540

Pro Ala Thr Val Pro Ala Ala Leu Ser Ile Leu Ser Thr Met Gln Pro
545 550 555 560

Ser Thr Leu Glu Thr Phe Pro Asp Leu Phe Cys Leu Pro Leu Gly Glu
565 570 575

Ser Phe Ser Ala Leu Thr Val Ser Glu His Val Ser Tyr Ile Val Thr
580 585 590

Asn Gln Tyr Leu Ile Lys Gly Ile Ser Tyr Pro Val Ser Thr Thr Val
595 600 605

Val Gly Gln Ser Leu Ile Ile Thr Gln Thr Asp Ser Gln Thr Lys Cys
610 615 620

Glu Leu Thr Arg Asn Met His Thr Thr His Ser Ile Thr Val Ala Leu
625 630 635 640

Asn Ile Ser Leu Glu Asn Cys Ala Phe Cys Gln Ser Ala Leu Leu Glu
645 650 655

Tyr Asp Asp Thr Gln Gly Val Ile Asn Ile Met Tyr Met His Asp Ser
660 665 670

Asp Asp Val Leu Phe Ala Leu Asp Pro Tyr Asn Glu Val Val Val Ser
675 680 685

Ser Pro Arg Thr His Tyr Leu Met Leu Leu Lys Asn Gly Thr Val Leu
690 695 700

Glu Val Thr Asp Val Val Val Asp Ala Thr Asp
705 710 715

<210> SEQ ID NO 11
<211> LENGTH: 840
<212> TYPE: DNA
<213> ORGANISM: Cytomegalovirus

<400> SEQUENCE: 11
atgtgcagaa ggcccgactg cggcttcagc ttcagccctg gacccgtgat cctgctgtgg 60
tgctgcctgc tgctgcctat cgtgtcctct gccgccgtgt ctgtggcccc tacagccgcc 120
gagaaggtgc cagccgagtg ccccgagctg accagaagat gcctgctggg cgaggtgttc 180
gagggcgaca agtacgagag ctggctgcgg cccctggtca acgtgaccgg cagagatggc 240
cccctgagcc agctgatccg gtacagaccc gtgacccccg aggccgccaa tagcgtgctg 300
ctggacgagg ccttcctgga taccctggcc ctgctgtaca acaaccccga ccagctgaga 360
gccctgctga ccctgctgtc cagcgacacc gcccccagat ggatgaccgt gatgcggggc 420
tacagcgagt gtggagatgg cagccctgcc gtgtacacct gcgtggacga cctgtgcaga 480
ggctacgacc tgaccagact gagctacggc cggtccatct tcacagagca cgtgctgggc 540
ttcgagctgg tgccccccag cctgttcaac gtggtggtgg ccatccggaa cgaggccacc 600
agaaccaaca gagccgtgcg gctgcctgtg tctacagccg ctgcacctga gggcatcaca 660
ctgttctacg gcctgtacaa cgccgtgaaa gagttctgcc tccggcacca gctggatccc 720
cccctgctga gacacctgga caagtactac gccggcctgc ccccagagct gaagcagacc 780
agagtgaacc tgcccgccca cagcagatat ggccctcagg ccgtggacgc cagatgataa 840

<210> SEQ ID NO 12
<211> LENGTH: 278
<212> TYPE: PRT
<213> ORGANISM: Cytomegalovirus

<400> SEQUENCE: 12

Met Cys Arg Arg Pro Asp Cys Gly Phe Ser Phe Ser Pro Gly Pro Val
1               5                   10                  15

Ile Leu Leu Trp Cys Cys Leu Leu Leu Pro Ile Val Ser Ser Ala Ala
            20                  25                  30

Val Ser Val Ala Pro Thr Ala Ala Glu Lys Val Pro Ala Glu Cys Pro
        35                  40                  45

Glu Leu Thr Arg Arg Cys Leu Leu Gly Glu Val Phe Glu Gly Asp Lys
    50                  55                  60

Tyr Glu Ser Trp Leu Arg Pro Leu Val Asn Val Thr Gly Arg Asp Gly
65                  70                  75                  80

Pro Leu Ser Gln Leu Ile Arg Tyr Arg Pro Val Thr Pro Glu Ala Ala
                85                  90                  95

Asn Ser Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
    130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

-continued

Val Ala Ile Arg Asn Glu Ala Thr Arg Thr Asn Arg Ala Val Arg Leu
195 200 205

Pro Val Ser Thr Ala Ala Ala Pro Glu Gly Ile Thr Leu Phe Tyr Gly
210 215 220

Leu Tyr Asn Ala Val Lys Glu Phe Cys Leu Arg His Gln Leu Asp Pro
225 230 235 240

Pro Leu Leu Arg His Leu Asp Lys Tyr Tyr Ala Gly Leu Pro Pro Glu
245 250 255

Leu Lys Gln Thr Arg Val Asn Leu Pro Ala His Ser Arg Tyr Gly Pro
260 265 270

Gln Ala Val Asp Ala Arg
275

<210> SEQ ID NO 13
<211> LENGTH: 1119
<212> TYPE: DNA
<213> ORGANISM: Cytomegalovirus

<400> SEQUENCE: 13
atggccccca gccacgtgga caaagtgaac acccggactt ggagcgccag catcgtgttc 60
atggtgctga ccttcgtgaa cgtgtccgtg cacctggtgc tgtccaactt cccccacctg 120
ggctacccct gcgtgtacta ccacgtggtg gacttcgagc ggctgaacat gagcgcctac 180
aacgtgatgc acctgcacac ccccatgctg tttctggaca gcgtgcagct cgtgtgctac 240
gccgtgttca tgcagctggt gtttctggcc gtgaccatct actacctcgt gtgctggatc 300
aagatcagca tgcggaagga caagggcatg agcctgaacc agagcacccg ggacatcagc 360
tacatgggcg acagcctgac cgccttcctg ttcatcctga gcatggacac cttccagctg 420
ttcaccctga ccatgagctt ccggctgccc agcatgatcg ccttcatggc cgccgtgcac 480
tttttctgtc tgaccatctt caacgtgtcc atggtcaccc agtaccggtc ctacaagcgg 540
agcctgttct tcttctcccg gctgcacccc aagctgaagg gcaccgtgca gttccggacc 600
ctgatcgtga acctggtgga ggtggccctg ggcttcaata ccaccgtggt ggctatggcc 660
ctgtgctacg gcttcggcaa caacttcttc gtgcggaccg gccatatggt gctggccgtg 720
ttcgtggtgt acgccatcat cagcatcatc tactttctgc tgatcgaggc cgtgttcttc 780
cagtacgtga aggtgcagtt cggctaccat ctgggcgcct ttttcggcct gtgcggcctg 840
atctacccca tcgtgcagta cgacaccttc ctgagcaacg agtaccggac cggcatcagc 900
tggtccttcg gaatgctgtt cttcatctgg gccatgttca ccacctgcag agccgtgcgg 960
tacttcagag gcagaggcag cggctccgtg aagtaccagg ccctggccac agcctctggc 1020
gaagaggtgg ccgccctgag ccaccacgac agcctggaaa gcagacggct gcgggaggaa 1080
gaggacgacg acgacgagga cttcgaggac gcctgataa 1119

<210> SEQ ID NO 14
<211> LENGTH: 371
<212> TYPE: PRT
<213> ORGANISM: Cytomegalovirus

<400> SEQUENCE: 14

Met Ala Pro Ser His Val Asp Lys Val Asn Thr Arg Thr Trp Ser Ala
1 5 10 15

Ser Ile Val Phe Met Val Leu Thr Phe Val Asn Val Ser Val His Leu
20 25 30

Val Leu Ser Asn Phe Pro His Leu Gly Tyr Pro Cys Val Tyr Tyr His

```
        35                  40                  45

Val Val Asp Phe Glu Arg Leu Asn Met Ser Ala Tyr Asn Val Met His
    50                  55                  60

Leu His Thr Pro Met Leu Phe Leu Asp Ser Val Gln Leu Val Cys Tyr
65                  70                  75                  80

Ala Val Phe Met Gln Leu Val Phe Leu Ala Val Thr Ile Tyr Tyr Leu
                85                  90                  95

Val Cys Trp Ile Lys Ile Ser Met Arg Lys Asp Lys Gly Met Ser Leu
            100                 105                 110

Asn Gln Ser Thr Arg Asp Ile Ser Tyr Met Gly Asp Ser Leu Thr Ala
        115                 120                 125

Phe Leu Phe Ile Leu Ser Met Asp Thr Phe Gln Leu Phe Thr Leu Thr
    130                 135                 140

Met Ser Phe Arg Leu Pro Ser Met Ile Ala Phe Met Ala Ala Val His
145                 150                 155                 160

Phe Phe Cys Leu Thr Ile Phe Asn Val Ser Met Val Thr Gln Tyr Arg
                165                 170                 175

Ser Tyr Lys Arg Ser Leu Phe Phe Phe Ser Arg Leu His Pro Lys Leu
            180                 185                 190

Lys Gly Thr Val Gln Phe Arg Thr Leu Ile Val Asn Leu Val Glu Val
        195                 200                 205

Ala Leu Gly Phe Asn Thr Thr Val Val Ala Met Ala Leu Cys Tyr Gly
    210                 215                 220

Phe Gly Asn Asn Phe Phe Val Arg Thr Gly His Met Val Leu Ala Val
225                 230                 235                 240

Phe Val Val Tyr Ala Ile Ile Ser Ile Ile Tyr Phe Leu Leu Ile Glu
                245                 250                 255

Ala Val Phe Phe Gln Tyr Val Lys Val Gln Phe Gly Tyr His Leu Gly
            260                 265                 270

Ala Phe Phe Gly Leu Cys Gly Leu Ile Tyr Pro Ile Val Gln Tyr Asp
        275                 280                 285

Thr Phe Leu Ser Asn Glu Tyr Arg Thr Gly Ile Ser Trp Ser Phe Gly
    290                 295                 300

Met Leu Phe Phe Ile Trp Ala Met Phe Thr Thr Cys Arg Ala Val Arg
305                 310                 315                 320

Tyr Phe Arg Gly Arg Gly Ser Gly Ser Val Lys Tyr Gln Ala Leu Ala
                325                 330                 335

Thr Ala Ser Gly Glu Glu Val Ala Ala Leu Ser His His Asp Ser Leu
            340                 345                 350

Glu Ser Arg Arg Leu Arg Glu Glu Glu Asp Asp Asp Asp Glu Asp Phe
        355                 360                 365

Glu Asp Ala
    370


<210> SEQ ID NO 15
<211> LENGTH: 411
<212> TYPE: DNA
<213> ORGANISM: Cytomegalovirus

<400> SEQUENCE: 15

atggaatgga acaccctggt cctgggcctg ctggtgctgt ctgtcgtggc cagcagcaac      60

aacacatcca cagccagcac ccctagacct agcagcagca cccacgccag cactaccgtg     120

aaggctacca ccgtggccac cacaagcacc accactgcta ccagcaccag ctccaccacc     180
```

```
tctgccaagc ctggctctac cacacacgac cccaacgtga tgaggcccca cgcccacaac    240

gacttctaca acgctcactg caccagccac atgtacgagc tgtccctgag cagctttgcc    300

gcctggtgga ccatgctgaa cgccctgatc ctgatgggcg ccttctgcat cgtgctgcgg    360

cactgctgct tccagaactt caccgccacc accaccaagg gctactgata a             411
```

<210> SEQ ID NO 16
<211> LENGTH: 135
<212> TYPE: PRT
<213> ORGANISM: Cytomegalovirus

<400> SEQUENCE: 16

```
Met Glu Trp Asn Thr Leu Val Leu Gly Leu Leu Val Leu Ser Val Val
1               5                   10                  15

Ala Ser Ser Asn Asn Thr Ser Thr Ala Ser Thr Pro Arg Pro Ser Ser
            20                  25                  30

Ser Thr His Ala Ser Thr Thr Val Lys Ala Thr Thr Val Ala Thr Thr
        35                  40                  45

Ser Thr Thr Thr Ala Thr Ser Thr Ser Ser Thr Thr Ser Ala Lys Pro
    50                  55                  60

Gly Ser Thr Thr His Asp Pro Asn Val Met Arg Pro His Ala His Asn
65                  70                  75                  80

Asp Phe Tyr Asn Ala His Cys Thr Ser His Met Tyr Glu Leu Ser Leu
                85                  90                  95

Ser Ser Phe Ala Ala Trp Trp Thr Met Leu Asn Ala Leu Ile Leu Met
            100                 105                 110

Gly Ala Phe Cys Ile Val Leu Arg His Cys Cys Phe Gln Asn Phe Thr
        115                 120                 125

Ala Thr Thr Thr Lys Gly Tyr
    130                 135
```

<210> SEQ ID NO 17
<211> LENGTH: 1422
<212> TYPE: DNA
<213> ORGANISM: Cytomegalovirus

<400> SEQUENCE: 17

```
atgggcaaga aagaaatgat catggtcaag ggcatcccca agatcatgct gctgattagc     60

atcacctttc tgctgctgtc cctgatcaac tgcaacgtgc tggtcaacag ccggggcacc    120

agaagatcct ggccctacac cgtgctgtcc taccggggca aagagatcct gaagaagcag    180

aaagaggaca tcctgaagcg gctgatgagc accagcagcg acggctaccg gttcctgatg    240

taccccagcc agcagaaatt ccacgccatc gtgatcagca tggacaagtt cccccaggac    300

tacatcctgg ccggacccat ccggaacgac agcatcaccc acatgtggtt cgacttctac    360

agcacccagc tgcggaagcc cgccaaatac gtgtacagcg agtacaacca caccgcccac    420

aagatcaccc tgaggcctcc cccttgtggc accgtgccca gcatgaactg cctgagcgag    480

atgctgaacg tgtccaagcg gaacgacacc ggcgagaagg gctgcggcaa cttcaccacc    540

ttcaacccca tgttcttcaa cgtgccccgg tggaacacca agctgtacat cggcagcaac    600

aaagtgaacg tggacagcca gaccatctac tttctgggcc tgaccgccct gctgctgaga    660

tacgcccagc ggaactgcac ccggtccttc tacctggtca acgccatgag ccggaacctg    720

ttccgggtgc ccaagtacat caacggcacc aagctgaaga acaccatgcg gaagctgaag    780

cggaagcagg ccctggtcaa agagcagccc cagaagaaga acaagaagtc ccagagcacc    840
```

```
accacccct acctgagcta caccacctcc accgccttca acgtgaccac caacgtgacc    900

tacagcgcca cagccgccgt gaccagagtg gccacaagca ccaccggcta ccggcccgac    960

agcaacttta tgaagtccat catggccacc cagctgagag atctggccac ctgggtgtac   1020

accaccctgc ggtacagaaa cgagcccttc tgcaagcccg accggaacag aaccgccgtg   1080

agcgagttca tgaagaatac ccacgtgctg atcagaaacg agacacccta caccatctac   1140

ggcaccctgg acatgagcag cctgtactac aacgagacaa tgagcgtgga gaacgagaca   1200

gccagcgaca acaacgaaac cacccccacc tcccccagca cccggttcca gcggaccttc   1260

atcgaccccc tgtgggacta cctggacagc ctgctgttcc tggacaagat ccggaacttc   1320

agcctgcagc tgcccgccta cggcaatctg acccccccctg agcacagaag ggccgccaac  1380

ctgagcaccc tgaacagcct gtggtggtgg agccagtgat aa                      1422
```

<210> SEQ ID NO 18
<211> LENGTH: 472
<212> TYPE: PRT
<213> ORGANISM: Cytomegalovirus

<400> SEQUENCE: 18

```
Met Gly Lys Lys Glu Met Ile Met Val Lys Gly Ile Pro Lys Ile Met
1               5                   10                  15

Leu Leu Ile Ser Ile Thr Phe Leu Leu Leu Ser Leu Ile Asn Cys Asn
            20                  25                  30

Val Leu Val Asn Ser Arg Gly Thr Arg Arg Ser Trp Pro Tyr Thr Val
        35                  40                  45

Leu Ser Tyr Arg Gly Lys Glu Ile Leu Lys Lys Gln Lys Glu Asp Ile
    50                  55                  60

Leu Lys Arg Leu Met Ser Thr Ser Ser Asp Gly Tyr Arg Phe Leu Met
65                  70                  75                  80

Tyr Pro Ser Gln Gln Lys Phe His Ala Ile Val Ile Ser Met Asp Lys
                85                  90                  95

Phe Pro Gln Asp Tyr Ile Leu Ala Gly Pro Ile Arg Asn Asp Ser Ile
            100                 105                 110

Thr His Met Trp Phe Asp Phe Tyr Ser Thr Gln Leu Arg Lys Pro Ala
        115                 120                 125

Lys Tyr Val Tyr Ser Glu Tyr Asn His Thr Ala His Lys Ile Thr Leu
    130                 135                 140

Arg Pro Pro Pro Cys Gly Thr Val Pro Ser Met Asn Cys Leu Ser Glu
145                 150                 155                 160

Met Leu Asn Val Ser Lys Arg Asn Asp Thr Gly Glu Lys Gly Cys Gly
                165                 170                 175

Asn Phe Thr Thr Phe Asn Pro Met Phe Phe Asn Val Pro Arg Trp Asn
            180                 185                 190

Thr Lys Leu Tyr Ile Gly Ser Asn Lys Val Asn Val Asp Ser Gln Thr
        195                 200                 205

Ile Tyr Phe Leu Gly Leu Thr Ala Leu Leu Leu Arg Tyr Ala Gln Arg
    210                 215                 220

Asn Cys Thr Arg Ser Phe Tyr Leu Val Asn Ala Met Ser Arg Asn Leu
225                 230                 235                 240

Phe Arg Val Pro Lys Tyr Ile Asn Gly Thr Lys Leu Lys Asn Thr Met
                245                 250                 255

Arg Lys Leu Lys Arg Lys Gln Ala Leu Val Lys Glu Gln Pro Gln Lys
            260                 265                 270
```

```
Lys Asn Lys Lys Ser Gln Ser Thr Thr Thr Pro Tyr Leu Ser Tyr Thr
        275                 280                 285

Thr Ser Thr Ala Phe Asn Val Thr Thr Asn Val Thr Tyr Ser Ala Thr
    290                 295                 300

Ala Ala Val Thr Arg Val Ala Thr Ser Thr Thr Gly Tyr Arg Pro Asp
305                 310                 315                 320

Ser Asn Phe Met Lys Ser Ile Met Ala Thr Gln Leu Arg Asp Leu Ala
                325                 330                 335

Thr Trp Val Tyr Thr Thr Leu Arg Tyr Arg Asn Glu Pro Phe Cys Lys
            340                 345                 350

Pro Asp Arg Asn Arg Thr Ala Val Ser Glu Phe Met Lys Asn Thr His
        355                 360                 365

Val Leu Ile Arg Asn Glu Thr Pro Tyr Thr Ile Tyr Gly Thr Leu Asp
    370                 375                 380

Met Ser Ser Leu Tyr Tyr Asn Glu Thr Met Ser Val Glu Asn Glu Thr
385                 390                 395                 400

Ala Ser Asp Asn Asn Glu Thr Thr Pro Thr Ser Pro Ser Thr Arg Phe
                405                 410                 415

Gln Arg Thr Phe Ile Asp Pro Leu Trp Asp Tyr Leu Asp Ser Leu Leu
            420                 425                 430

Phe Leu Asp Lys Ile Arg Asn Phe Ser Leu Gln Leu Pro Ala Tyr Gly
        435                 440                 445

Asn Leu Thr Pro Pro Glu His Arg Arg Ala Ala Asn Leu Ser Thr Leu
    450                 455                 460

Asn Ser Leu Trp Trp Trp Ser Gln
465                 470


<210> SEQ ID NO 19
<211> LENGTH: 519
<212> TYPE: DNA
<213> ORGANISM: Cytomegalovirus

<400> SEQUENCE: 19

atgagcccca aggacctgac ccccttcctg acaaccctgt ggctgctcct gggccatagc      60

agagtgccta gagtgcgggc cgaggaatgc tgcgagttca tcaacgtgaa ccaccccccc     120

gagcggtgct acgacttcaa gatgtgcaac cggttcaccg tggccctgag atgccccgac     180

ggcgaagtgt gctacagccc cgagaaaacc gccgagatcc ggggcatcgt gaccaccatg     240

acccacagcc tgacccggca ggtggtgcac aacaagctga ccagctgcaa ctacaacccc     300

ctgtacctgg aagccgacgg ccggatcaga tgcggcaaag tgaacgacaa ggcccagtac     360

ctgctgggag ccgccggaag cgtgccctac cggtggatca acctggaata cgacaagatc     420

acccggatcg tgggcctgga ccagtacctg gaaagcgtga agaagcacaa gcggctggac     480

gtgtgcagag ccaagatggg ctacatgctg cagtgataa                            519


<210> SEQ ID NO 20
<211> LENGTH: 171
<212> TYPE: PRT
<213> ORGANISM: Cytomegalovirus

<400> SEQUENCE: 20

Met Ser Pro Lys Asp Leu Thr Pro Phe Leu Thr Thr Leu Trp Leu Leu
1               5                   10                  15

Leu Gly His Ser Arg Val Pro Arg Val Arg Ala Glu Glu Cys Cys Glu
            20                  25                  30
```

```
Phe Ile Asn Val Asn His Pro Pro Glu Arg Cys Tyr Asp Phe Lys Met
        35                  40                  45

Cys Asn Arg Phe Thr Val Ala Leu Arg Cys Pro Asp Gly Glu Val Cys
    50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
    130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170


<210> SEQ ID NO 21
<211> LENGTH: 648
<212> TYPE: DNA
<213> ORGANISM: Cytomegalovirus

<400> SEQUENCE: 21

atgctgcggc tgctgctgag acaccacttc cactgcctgc tgctgtgtgc cgtgtgggcc      60

acccccttgtc tggccagccc ttggagcacc ctgaccgcca accagaaccc tagcccccct    120

tggtccaagc tgacctacag caagccccac gacgccgcca ccttctactg cccctttctg    180

taccccagcc ctcccagaag ccccctgcag ttcagcggct tccagagagt gtccaccggc    240

cctgagtgcc ggaacgagac actgtacctg ctgtacaacc gggagggcca gacactggtg    300

gagcggagca gcacctgggt gaaaaaagtg atctggtatc tgagcggccg gaaccagacc    360

atcctgcagc ggatgcccag aaccgccagc aagcccagcg acggcaacgt gcagatcagc    420

gtggaggacg ccaaaatctt cggcgcccac atggtgccca agcagaccaa gctgctgaga    480

ttcgtggtca acgacggcac cagatatcag atgtgcgtga tgaagctgga aagctgggcc    540

cacgtgttcc gggactactc cgtgagcttc caggtccggc tgaccttcac cgaggccaac    600

aaccagacct acaccttctg cacccacccc aacctgatcg tgtgataa                  648


<210> SEQ ID NO 22
<211> LENGTH: 214
<212> TYPE: PRT
<213> ORGANISM: Cytomegalovirus

<400> SEQUENCE: 22

Met Leu Arg Leu Leu Leu Arg His His Phe His Cys Leu Leu Leu Cys
1               5                   10                  15

Ala Val Trp Ala Thr Pro Cys Leu Ala Ser Pro Trp Ser Thr Leu Thr
            20                  25                  30

Ala Asn Gln Asn Pro Ser Pro Pro Trp Ser Lys Leu Thr Tyr Ser Lys
        35                  40                  45

Pro His Asp Ala Ala Thr Phe Tyr Cys Pro Phe Leu Tyr Pro Ser Pro
    50                  55                  60

Pro Arg Ser Pro Leu Gln Phe Ser Gly Phe Gln Arg Val Ser Thr Gly
65                  70                  75                  80
```

```
Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Arg Thr
        115                 120                 125

Ala Ser Lys Pro Ser Asp Gly Asn Val Gln Ile Ser Val Glu Asp Ala
    130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
        195                 200                 205

His Pro Asn Leu Ile Val
    210
```

<210> SEQ ID NO 23
<211> LENGTH: 393
<212> TYPE: DNA
<213> ORGANISM: Cytomegalovirus

<400> SEQUENCE: 23

```
atgcggctgt gcagagtgtg gctgtccgtg tgcctgtgtg ccgtggtgct gggccagtgc      60

cagagagaga cagccgagaa gaacgactac taccgggtgc cccactactg ggatgcctgc     120

agcagagccc tgcccgacca gacccggtac aaatacgtgg agcagctcgt ggacctgacc     180

ctgaactacc actacgacgc cagccacggc ctggacaact tcgacgtgct gaagcggatc     240

aacgtgaccg aggtgtccct gctgatcagc gacttccggc ggcagaacag aagaggcggc     300

accaacaagc ggaccacctt caacgccgct ggctctctgg cccctcacgc cagatccctg     360

gaattcagcg tgcggctgtt cgccaactga taa                                  393
```

<210> SEQ ID NO 24
<211> LENGTH: 129
<212> TYPE: PRT
<213> ORGANISM: Cytomegalovirus

<400> SEQUENCE: 24

```
Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr Tyr Arg
            20                  25                  30

Val Pro His Tyr Trp Asp Ala Cys Ser Arg Ala Leu Pro Asp Gln Thr
        35                  40                  45

Arg Tyr Lys Tyr Val Glu Gln Leu Val Asp Leu Thr Leu Asn Tyr His
    50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95

Arg Arg Gly Gly Thr Asn Lys Arg Thr Thr Phe Asn Ala Ala Gly Ser
            100                 105                 110
```

-continued

```
Leu Ala Pro His Ala Arg Ser Leu Glu Phe Ser Val Arg Leu Phe Ala
        115                 120                 125

Asn


<210> SEQ ID NO 25
<211> LENGTH: 2371
<212> TYPE: DNA
<213> ORGANISM: Parvovirus

<400> SEQUENCE: 25

acgcgtacaa aacaaaatgt ctaagaaatc tggtaaatgg tgggaatctg atgataaatt     60

tgctaaggct gtttaccaac aatttgttga attttacgaa aaggttactg gtactgattt    120

ggaattgatt caaattttga aggatcatta caacatttct ttggataatc cattggaaaa    180

tccatcttca ttgtttgatt tggttgctag aattaagaac aacttgaaga actctccaga    240

tttgtattct catcatttcc aatctcatgg tcaattgtct gatcatccac atgctttatc    300

ttcatcttca tctcatgctg aaccaagagg tgaaaatgct gttttatctt ctgaagattt    360

gcataaacca ggtcaagttt ctgttcaatt gccaggtact aattacgttg gtccaggtaa    420

tgaattgcaa gctggtccac cacaatctgc tgttgattct gctgctagaa ttcatgattt    480

cagatactct caattggcta agttgggtat taatccatat actcattgga ctgttgctga    540

tgaagaattg ttgaagaaca ttaagaatga aactggtttt caagctcaag ttgttaaaga    600

ttacttcact ttgaaaggtg ctgctgctcc agttgctcat tttcaaggtt ctttgccaga    660

agttccagct tataacgctt ctgaaaaata tccatctatg acatctgtta attctgctga    720

agcatctact ggtgcaggtg gaggtggttc taattctgtt aaatctatgt ggtctgaagg    780

tgctactttt tctgctaatt cagttacttg tactttctct agacaattct tgattccata    840

tgatccagaa catcattaca aagttttttc accagctgct tcatcttgtc ataatgcttc    900

aggtaaagaa gctaaggttt gtactatttc tccaattatg ggttattcta ctccttggag    960

atacttggat tttaatgctt tgaacttgtt tttttctcca ttggaatttc aacatttgat   1020

tgaaaactac ggttctattg ctccagatgc tttgactgtt actatttctg aaattgctgt   1080

taaggatgtt actgataaaa caggtggtgg tgttcaagtt actgattcta ctactggtag   1140

attgtgcatg ttggttgatc atgaatacaa atacccatac gttttgggtc aaggtcaaga   1200

tactttggct ccagaattgc caatttgggt ttattttcca ccacaatacg cttatttgac   1260

tgttggtgat gttaatactc aaggtatttc tggtgattct aaaaagttgg cttctgaaga   1320

atctgctttt tacgttttgg aacattcttc ttttcaattg ttgggtactg gtggtactgc   1380

ttctatgtct tacaaatttc caccagttcc acctgaaaat ttggaaggtt gttctcaaca   1440

tttttacgaa atgtacaatc cattgtatgg ttctagattg ggtgttccag atactttggg   1500

tggtgatcca aaatttagat ctttgactca tgaagatcat gctattcaac cacaaaattt   1560

catgccaggt ccattggtta attctgtttc tactaaagaa ggtgattctt ctaatacagg   1620

tgctggtaaa gcattgactg gtttgtctac tggtacttct caaaacacta gaatttcttt   1680

aagaccaggt ccagtttcac aaccatatca tcattgggat actgataagt acgttactgg   1740

tattaatgct atttcacatg gtcaaactac ttatggtaat gctgaagata aagaatatca   1800

acaaggtgtt ggtagatttc caaacgaaaa agaacaattg aaacaattgc aaggtttgaa   1860

tatgcatact tactttccaa acaaaggtac tcaacaatac actgatcaaa ttgaaagacc   1920

attgatggtt ggttctgttt ggaatagaag agctttgcat tatgaatctc aattgtggtc   1980
```

-continued

```
taagattcca aatttagatg attctttcaa gactcaattt gctgctttgg gtggttgggg   2040

tttgcatcaa cctccaccac aaattttctt gaagattttg ccacaatctg gtccaattgg   2100

tggtattaaa tctatgggta ttactacttt ggttcaatat gctgttggta ttatgactgt   2160

tacaatgact tttaagttgg gtccaagaaa agctacaggt agatggaatc cacaaccagg   2220

tgtttatcca ccacatgctg ctggtcattt gccttacgtt ttgtatgatc caactgctac   2280

tgatgctaaa caacatcata gacatggtta tgaaaaacct gaagaattgt ggactgctaa   2340

atctagagtt catccattgt aatgagtcga c                                  2371
```

<210> SEQ ID NO 26
<211> LENGTH: 1692
<212> TYPE: DNA
<213> ORGANISM: Parvovirus

<400> SEQUENCE: 26

```
cctaggacaa aacaaaatga catctgttaa ttctgctgaa gcatctactg gtgcaggtgg     60

aggtggttct aattctgtta aatctatgtg gtctgaaggt gctacttttt ctgctaattc    120

agttacttgt actttctcta gacaattctt gattccatat gatccagaac atcattacaa    180

agtttttca ccagctgctt catcttgtca taatgcttca ggtaaagaag ctaaggtttg     240

tactatttct ccaattatgg gttattctac tccttggaga tacttggatt ttaatgcttt    300

gaacttgttt ttttctccat tggaatttca acatttgatt gaaaactacg gttctattgc    360

tccagatgct ttgactgtta ctatttctga aattgctgtt aaggatgtta ctgataaaac    420

aggtggtggt gttcaagtta ctgattctac tactggtaga ttgtgcatgt tggttgatca    480

tgaatacaaa tacccatacg ttttgggtca aggtcaagat actttggctc cagaattgcc    540

aatttgggtt tattttccac cacaatacgc ttatttgact gttggtgatg ttaatactca    600

aggtatttct ggtgattcta aaaagttggc ttctgaagaa tctgcttttt acgttttgga    660

acattcttct tttcaattgt tgggtactgg tggtactgct tctatgtctt acaaatttcc    720

accagttcca cctgaaaatt tggaaggttg ttctcaacat tttacgaaa tgtacaatcc     780

attgtatggt tctagattgg gtgttccaga tactttgggt ggtgatccaa aatttagatc    840

tttgactcat gaagatcatg ctattcaacc acaaaatttc atgccaggtc cattggttaa    900

ttctgtttct actaaagaag gtgattcttc taatacaggt gctggtaaag cattgactgg    960

tttgtctact ggtacttctc aaaacactag aatttcttta agaccaggtc cagtttcaca   1020

accatatcat cattgggata ctgataagta cgttactggt attaatgcta tttcacatgg   1080

tcaaactact tatggtaatg ctgaagataa agaatatcaa caaggtgttg gtagatttcc   1140

aaacgaaaaa gaacaattga aacaattgca aggtttgaat atgcatactt actttccaaa   1200

caaaggtact caacaataca ctgatcaaat tgaaagacca ttgatggttg gttctgtttg   1260

gaatagaaga gctttgcatt atgaatctca attgtggtct aagattccaa atttagatga   1320

ttctttcaag actcaatttg ctgctttggg tggttggggt ttgcatcaac ctccaccaca   1380

aattttcttg aagattttgc cacaatctgg tccaattggt ggtattaaat ctatgggtat   1440

tactactttg gttcaatatg ctgttggtat tatgactgtt acaatgactt ttaagttggg   1500
```

-continued

| | | | | | | |
|---|---|---|---|---|---|---|
| tccaagaaaa | gctacaggta | gatggaatcc | acaaccaggt | gtttatccac | cacatgctgc | 1560 |
| tggtcatttg | ccttacgttt | tgtatgatcc | aactgctact | gatgctaaac | aacatcatag | 1620 |
| acatggttat | gaaaaacctg | aagaattgtg | gactgctaaa | tctagagttc | atccattgta | 1680 |
| atgagcggcc | gc | | | | | 1692 |

IMMUNOGENIC COMBINATION COMPOSITIONS AND USES THEREOF

RELATED APPLICATION

This application is a U.S. National Phase of International Application No. PCT/US2012/045847, filed Jul. 6, 2012 and published in English, which claims the benefit of U.S. Provisional Application No. 61/505,093 filed on Jul. 6, 2011. The entire contents of the foregoing applications are hereby incorporated by reference.

SEQUENCE LISTING

The instant application contains a Sequence Listing which has been submitted in ASCII format via EFS-Web and is hereby incorporated by reference in its entirety. Said ASCII copy, created on Jul. 5, 2012, is named PAT54676.txt and is 76,996 bytes in size.

BACKGROUND OF THE INVENTION

Combination vaccines merge antigens that prevent different diseases or that protect against multiple strains of infectious agents causing the same disease into a single product. Thus, they reduce the number of injections required to prevent some diseases. Potential advantages of combination vaccines include a) reducing the cost of stocking and administering separate vaccines, b) reducing the cost for extra health-care visits, and c) facilitating the addition of new vaccines into immunization programs.

Nucleic acid based vaccines are an attractive approach to vaccination. For example, intramuscular (IM) immunization of plasmid DNA encoding an antigen can induce cellular and humoral immune responses and protect against challenge. DNA vaccines offer certain advantages over traditional vaccines using protein antigens, or attenuated pathogens. For example, as compared to protein vaccines, DNA vaccines can be more effective in producing a properly folded antigen in its native conformation, and in generating a cellular immune response. DNA vaccines also do not have some of the safety problems associated with killed or attenuated pathogens. For example, a killed viral preparation may contain residual live viruses, and an attenuated virus may mutate and revert to a pathogenic phenotype. DNA vaccines are generally effective in generating cell mediated immunity (such as interferon-γ secreting antigen-specific T-cells and antigen-specific cytotoxic T-cells), but less effective in generating antibodies against the encoded and expressed antigen.

WO 97/28818 discloses a vaccine that delivers a nucleic acid and a protein antigen to antigen presenting cells. The nucleic acid may encode the same protein as the protein antigen. The nucleic acid and protein are "complexed," e.g., by covalent conjugation. The complex may be formulated as a synthetic virus-like particle. It is also suggested that liposomal systems may be used.

U.S. Pat. No. 7,604,803 discloses the co-delivery of nucleic acid and its encoded protein to the same cell using a liposomal system. The DNA molecule and its encoded protein are entrapped within the same liposomal vehicle, such that the two entities arrive at antigen-presenting cells together, resulting in the processing and presentation of the protein form of the antigen, together with the expression of the DNA-encoded form of the antigen in the same cell.

WO 2009/074861 discloses a vaccine comprising (i) a nucleic acid sequence encoding at least one influenza virus antigen coated onto carrier particles, and (ii) an assistor protein for sequential or concomitant administration. The assistor protein and the antigen encoded by the nucleic acid molecule share at least one common epitope.

It is known that non-coding plasmid DNA has an immuno-adjuvant action when co-entrapped with peptides in liposomal vesicles (Gursel, M. et al. Vaccine (1999) 17: 1376-1383) and that DNA with CpG motifs has an adjuvant effect on naked DNA and peptide vaccines (Klinman, D. M. et al. Vaccine (1999) 17: 19-25).

Concerns have been raised regarding the safety of DNA-based vaccines. The introduced DNA molecules could potentially integrate into the host genome or, due to their distribution to various tissues, could lead to undesirable sustained expression of antigens. In addition, certain DNA viruses have also been used to deliver DNA molecules. Because of their infectious properties, such viruses achieve a very high transfection rate. The viruses used are genetically modified to prevent the formation of functional infectious particles in the transfected cell. Despite these precautions, however, it is not possible to rule out the risk of uncontrolled propagation of the introduced gene and viral genes, for example due to potential recombination events. This also entails the risk of the DNA being inserted into an intact gene of the host cell's genome by e.g. recombination, with the consequence that the host gene may be mutated and thus completely or partially inactivated or may give rise to misinformation. In other words, synthesis of a host gene product which is vital to the cell may be completely suppressed or, alternatively, a modified or incorrect gene product is expressed.

RNA molecules encoding an antigen or a derivative thereof may also be used as vaccines. RNA vaccines offer certain advantages as compared to DNA vaccines. However, compared with DNA-based vaccines, relatively minor attention has been given to RNA-based vaccines. RNAs are highly susceptible to degradation by nucleases when administered as a therapeutic or vaccine. See, e.g., Vajdy, M., et al., *Mucosal adjuvants and delivery systems for protein-, DNA- and RNA-based vaccines*, Immunol Cell Biol, 2004. 82(6): p. 617-27.

Toll-like receptors (TLRs) are a group of pattern recognition receptors which bind to pathogen-associated molecular patterns (PAMPS) from bacteria, fungi, protozoa and viruses, and act as a first line of defense against invading pathogens. Many TLRs have been identified in humans, mice, and other mammalian species. DNA molecules (such as bacterial or viral DNA) are recognized by TLR9, whereas RNA molecules (such as single stranded viral RNA) are recognized by TLR7 or TLR8.

T-cells and B-cells recognize antigens in different ways. T-cells recognize peptide fragments of proteins that are embedded in class-II or class-I MHC molecules at the surface of cells, whereas B-cells recognize surface features of an unprocessed antigen, via immunoglobulin-like cell surface receptors. The difference in antigen recognition mechanisms of T-cells and B-cells are reflected in the different natures of their epitopes. Thus, whereas B-cells recognize surface features of an antigen or a pathogen, T-cell epitopes (which comprise peptides of about 8-12 amino acids in length) can be "internal" as well as "surface" when viewed in the context of the three-dimensional structure of the antigen. Accordingly, a B-cell epitope is preferably exposed on the surface of the antigen or pathogen, and can be linear or conformational, whereas a T-cell epitope is typically linear but is not required to be available or on the surface of the antigen.

U.S. Pat. No. 7,862,829 discloses a method of producing an immune response by administering to an antigen and an alpha-virus-based adjuvant. The method is based on the discovery that alphavirus, a (+) ssRNA virus, can act as an adjuvant to enhance an immune response against an antigen, even though the antigen is not presented on or expressed by the virus. The alphavirus particles may be delivered by liposomal system.

There is a need to improve the efficacy of protein subunit vaccines and nucleic acid vaccines such as RNA vaccines.

SUMMARY OF THE INVENTION

This invention generally relates to immunogenic compositions that comprise an RNA component and a polypeptide component. The immunogenic compositions deliver a combination of antigenic epitopes in two different forms—a first epitope from a pathogen, in RNA-coded form; and a second epitope from a different pathogen, in polypeptide form—and can induce an immune response to both pathogens (e.g., without the need for a separate adjuvant). A practical benefit of the immunogenic compositions described herein is that the total number of immunogenic compositions needed to be administered to the patient is reduced due to the combination of two or more antigens in a single immunogenic composition. This is especially beneficial for infants and children who receive a large number of routine vaccinations.

The invention also relates to methods for treating or preventing two or more infectious diseases, methods for inducing an immune response against two or more pathogens, or methods of vaccinating a subject, by co-delivery of an RNA molecule and a polypeptide molecule (co-administration).

In one aspect, the invention provides an immunogenic composition comprising (i) a first polypeptide antigen, and (ii) a self-replicating RNA molecule that encodes a second polypeptide antigen, wherein the first and second antigens are antigens from different pathogens. In some embodiments, the first polypeptide antigen is a Cytomegalovirus (CMV) antigen. In some embodiments, the second polypeptide antigen is a Parvovirus antigen. The second polypeptide antigen can be in the form of a virus-like particle (CLP).

In some embodiments, the first polypeptide antigen is a soluble polypeptide, and the second polypeptide antigen is a soluble or membrane anchored polypeptide.

In some embodiments, the self-replicating RNA is an alphavirus-derived RNA replicon. The self-replicating RNA molecule may comprise one or more modified nucleotides.

In some embodiments, the immunogenic composition further comprises a cationic lipid, a liposome, a cochleate, a virosome, an immune-stimulating complex, a microparticle, a microsphere, a nanosphere, a unilamellar vesicle, a multilamellar vesicle, an oil-in-water emulsion, a water-in-oil emulsion, an emulsome, a polycationic peptide or a cationic nanoemulsion.

In some embodiments, the RNA molecule is encapsulated in, bound to or adsorbed on a cationic lipid, a liposome, a cochleate, a virosome, an immune-stimulating complex, a microparticle, a microsphere, a nanosphere, a unilamellar vesicle, a multilamellar vesicle, an oil-in-water emulsion, a water-in-oil emulsion, an emulsome, a polycationic peptide, a cationic nanoemulsion, or combinations thereof.

In some embodiments, the first and second polypeptide antigens are independently derived from a viral pathogen, a bacterial pathogen, a fungal pathogen, a protozoan pathogen, and a multi-cellular parasitic pathogen. The first polypeptide antigen and the second polypeptide antigen can both be viral antigens. In such instances, one viral antigen can be from CMV. In another instance, one viral antigen can be from Parvovirus. The parvovirus antigen can comprise an amino acid sequence selected from SEQ ID NOs:25-26. The viral antigen from CMV can be a gB antigen, a gH antigen, or a gL antigen. In some embodiments, the viral antigen from CMV can be a gH antigen or a gL antigen.

In some embodiments, the RNA molecule encodes a gH antigen and a gL antigen. In some embodiments, the immunogenic composition comprises a gH polypeptide antigen and gL polypeptide antigen.

In some embodiments, the immunogenic composition further comprises an adjuvant.

The invention also relates to immunogenic compositions that comprise (i) a Parvovirus polypeptide antigen, and (ii) a self-replicating RNA molecule that encodes a CMV polypeptide antigen.

The invention also relates to immunogenic compositions and a pharmaceutically acceptable carrier and/or a pharmaceutically acceptable vehicle.

The invention also relates to methods for treating or preventing an infectious disease. In some embodiments, a therapeutically effective amount of an immunogenic composition is administered to a subject.

The invention also relates to methods for inducing an immune response in a subject. In some embodiments, a therapeutically effective amount of an immunogenic composition is administered to the subject.

The invention also relates to methods of vaccinating a subject. In some embodiments, an immunogenic composition is administered to the subject.

DETAILED DESCRIPTION OF THE INVENTION

Certain terms that are used to describe the invention in this are defined and explained herein in Section 7.

1. Overview

One particular advantage of an RNA vaccine is that RNA molecules are self-adjuvanting. For example, RNA molecules can induce the production of cytokines, which can enhance the host immune response to the protein antigen that is encoded by the RNA molecule.

Vaccination strategies that combine an RNA molecule and a polypeptide molecule (e.g., administering an immunogenic composition that has an RNA component and a protein component) provide several benefits. RNA molecules promote type 1 T helper responses (Th1, IFN-$\gamma^{hi}$, IL-$4^{lo}$), whereas protein molecules promote type 2 T helper responses. Thus, combining an RNA molecule and a polypeptide molecule can promote both T cell-mediated immunity as well as humoral immunity. In addition, RNA molecules may be delivered to cells using delivery systems such as liposomes or oil-in-water emulsions. Liposomes and oil-in-water emulsions are also known to have adjuvant activities. Thus, the adjuvant activity of the RNA together with adjuvant activity of the delivery system can act synergistically to enhance the immune response to one or both antigens.

In one aspect, the invention relates to immunogenic compositions that comprise an RNA component from a first pathogen and a polypeptide component from a second pathogen Immunogenic compositions that deliver antigenic epitopes in two different forms—a first epitope from one pathogen, in RNA-coded form; and a second epitope from a different pathogen, in polypeptide form—can enhance the immune response to one or both pathogens.

As described herein, the inventors have evaluated the efficacies of immunogenic compositions that comprise (i) a self-replicating RNA molecule that encodes a CMV antigen, and (ii) a Parvovirus polypeptide antigen. These studies demonstrated that co-administering an RNA molecule that encodes a CMV antigen, together with the Parvovirus antigen in polypeptide form, potentiated the immune response to the Parvovirus antigen, resulting in higher antibody titers as compared to administering the Parvovirus polypeptide molecule alone.

The immunogenic compositions described herein can be formulated as a vaccine to induce or enhance the host immune response to a pathogen, such as to induce protective immunity. Also provided herein are methods of using the immunogenic compositions of the invention to induce or enhance an immune response in a subject in need thereof.

2. Immunogenic Compositions

In one aspect, the invention provides an immunogenic composition comprising: (i) a self-replicating RNA molecule that encodes a first polypeptide antigen; and (ii) a second polypeptide antigen; wherein said first and second polypeptide antigens are from different pathogens.

In certain embodiments, the RNA molecule may encode a first polypeptide antigen comprising a full-length protein from a pathogen (e.g., a viral protein), or an antigenic portion thereof, optionally fused with a tag sequence that may facilitate the expression, purification and/or detection of thel protein. The second polypeptide antigen may be a recombinant protein comprising a full-length protein from a different pathogen, or an antigenic portion thereof, optionally fused with a tag sequence that may facilitate the production, purification or detection of the protein. The first polypeptide antigen, the second polypeptide antigen, or both, may comprise a mutation variant of a protein from a pathogen (e.g., a viral protein having amino acid substitution(s), addition(s), or deletion(s)).

In certain embodiments, the first polypeptide antigen is a soluble or membrane anchored polypeptide, and the second polypeptide antigen is a soluble polypeptide. For example, if the wild type viral protein is a transmembrane surface protein, the RNA molecule may comprise the full-length coding sequence to produce the first (membrane-anchored) antigen, while the transmembrane region of the viral protein may be deleted to produce the second polypeptide antigen (which is soluble).

In certain embodiments, the first antigen or the second antigen is a fusion polypeptide further comprising a third epitope. The third epitope may be from a different pathogen, or from a different antigen of the same pathogen.

The self-replicating RNA molecule that encodies a first polypeptide antigent can be in the form of a VRP. The second polypeptide antigen can be in the form of a VLP.

A. Antigens

Antigens suitable for inclusion in the immunogenic compositions described herein (either in polypeptide form or in RNA-encoded form) may be derived from any pathogen (e.g., a bacterial pathogen, a viral pathogen, a fungal pathogen, a protozoan pathogen, or a multi-cellular parasitic pathogen), allergen or tumor.

In certain embodiments, the first and/or second antigens are derived from a viral pathogen. Exemplary viral pathogens include, e.g., respiratory syncytial virus (RSV), hepatitis B virus (HBV), hepatitis C virus (HCV), Dengue virus, herpes simplex virus (HSV; e.g., HSV-I, HSV-II), molluscum contagiosum virus, vaccinia virus, variola virus, lentivirus, human immunodeficiency virus (HIV), human papilloma virus (HPV), cytomegalovirus (CMV), varicella zoster virus (VZV), rhinovirus, enterovirus, adenovirus, coronavirus (e.g., SARS), influenza virus (flu), para-influenza virus, mumps virus, measles virus, papovavirus, hepadnavirus, flavivirus, retrovirus, arenavirus (e.g., Lymphocytic Choriomeningitis Virus, Junin virus, Machupo virus, Guanarito virus, or Lassa virus), norovirus, yellow fever virus, rabies virus, Filovirus (e.g., Ebola virus or marbug virus), hepatitis C virus, hepatitis B virus, hepatitis A virus, Morbilliviruses (e.g., measles virus), Rubulaviruses (e.g., mumps virus), Rubiviruses (e.g., rubella virus), bovine viral diarrhea virus. For example, the antigen can be CMV glycoprotein gH, or gL; Parvovirus; HIV glycoprotein gp120 or gp140, HIV p55 gag, pol; or RSV-F antigen, etc.

In some embodiments, the first and/or second antigens are derived from a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of atlantic salmon), landlocked salmon virus (LSV), atlantic salmon rotavirus (ASR), trout strawberry disease virus (TSD), coho salmon tumor virus (CSTV), or viral hemorrhagic septicemia virus (VHSV).

In some embodiments the first and/or second antigens are derived from a parasite from the *Plasmodium* genus, such as *P. falciparum, P. vivax, P. malariae* or *P. ovale*. Thus the invention may be used for immunizing against malaria. In some embodiments the first and/or second antigens are derived from a parasite from the Caligidae family, particularly those from the *Lepeophtheirus* and *Caligus* genera e.g. sea lice such as *Lepeophtheirus salmonis* or *Caligus rogercresseyi.*

In certain embodiments, first and/or second antigens are derived from a bacterial pathogen. Exemplary bacterial pathogens include, e.g., *Neisseria* spp, including N. gonorrhea and N. meningitides; *Streptococcus* spp, including *S. pneumoniae, S. pyogenes, S. agalactiae, S. mutans; Haemophilus* spp, including *H. influenzae* type B, non typeable *H. influenzae, H. ducreyi; Moraxella* spp, including *M. catarrhalis*, also known as *Branhamella catarrhalis; Bordetella* spp, including *B. pertussis, B. parapertussis* and *B. bronchiseptica; Mycobacterium* spp., including *M. tuberculosis, M. bovis, M. leprae, M. avium, M. paratuberculosis, M. smegmatis; Legionella* spp, including *L. pneumophila; Escherichia* spp, including enterotoxic *E. coli*, enterohemorragic *E. coli*, enteropathogenic *E. coli; Vibrio* spp, including *V. cholera, Shigella* spp, including *S. sonnei, S. dysenteriae, S. flexnerii; Yersinia* spp, including *Y. enterocolitica, Y. pestis, Y. pseudotuberculosis, Campylobacter* spp, including *C. jejuni* and *C. coli; Salmonella* spp, including *S. typhi, S. paratyphi, S. choleraesuis, S. enteritidis; Listeria* spp., including *L. monocytogenes; Helicobacter* spp, including *H pylori; Pseudomonas* spp, including *P. aeruginosa, Staphylococcus* spp., including *S. aureus, S. epidermidis; Enterococcus* spp., including *E. faecalis, E. faecium; Clostridium* spp., including *C. tetani, C. botulinum, C. difficile; Bacillus* spp., including *B. anthracis; Corynebacterium* spp., including *C. diphtheriae; Borrelia* spp., including *B. burgdorferi, B. garinii, B. afzelii, B. andersonii, B. hermsii; Ehrlichia* spp., including *E. equi* and the agent of the Human Granulocytic Ehrlichiosis; *Rickettsia* spp, including *R. rickettsii; Chlamydia* spp., including *C. trachomatis, C. neumoniae, C. psittaci; Leptsira* spp., including *L. interrogans; Treponema* spp., including *T. pallidum, T. denticola, T. hyodysenteriae.*

In certain embodiments, first and/or second antigens are derived from a fungal pathogen (e.g., a yeast or mold pathogen). Exemplary fungal pathogens include, e.g., *Aspergillus fumigatus, A. flavus, A. niger, A. terreus, A. nidulans, Coccidioides immitis, Coccidioides posadasii, Cryptococcus neoformans, Histoplasma capsulatum, Candida albicans*, and *Pneumocystis jirovecii.*

In certain embodiments, first and/or second antigens are derived from a protozoan pathogen. Exemplary protozoan pathogens include, e.g., *Toxoplasma gondii, Strongyloides stercoralis, Plasmodium falciparum, Plasmodium vivax, Plasmodium ovale* and *Plasmodium malariae.*

In certain embodiments, the first and/or second antigens are derived from a multi-cellular parasitic pathogen. Exemplary multicellular parasitic pathogens include, e.g., trematodes (flukes), cestodes (tapeworms), nematodes (roundworms), and arthropods.

In some embodiments, the first and/or second antigens are derived from an allergen, such as pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale*, and Sorghum, the orders of Asterales and Urticales including herbs of the genera *Ambrosia, Artemisia*, and *Parietaria*. Other important inhalation allergens are those from house dust mites of the genus *Dermatophagoides* and *Euroglyphus*, storage mite e.g. *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (Apidae), wasps (Vespidea), and ants (Formicoidae).

In some embodiments, the first and/or second antigens are derived from a tumor antigen selected from: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors; (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT; (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), mammaglobin, alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer); (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma); (e) prostate associated antigens such as PAP, PSA, PSMA, PSH-P1, PSM-P1, PSM-P2, associated with e.g., prostate cancer; (f) immunoglobulin idiotypes (associated with myeloma and B cell lymphomas, for example). In certain embodiments, tumor immunogens include, but are not limited to, p15, Hom/Me1-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS, and the like.

1. CMV

In certain embodiments, the first or second antigen is from CMV. In certain embodiments, the first or second antigen is derived from a capsid protein, an envelope glycoprotein (such as gB, gH, gL, gM, gN), or a tegument protein. In certain embodiments, the first or second antigen is derived from one or more of the following proteins: pp65, IE1, gB, gD, gH, gL, gM, gN, gO, UL128, UL129, gUL130, UL150, UL131, UL33, UL78, US27, US28, RL5A, RL6, RL10, RL11, RL12, RL13, UL1, UL2, UL4, UL5, UL6, UL7, ULB, UL9, UL10, UL11, UL14, UL15A, UL16, UL17, UL18, UL22A, UL38, UL40, UL41A, UL42, UL116, UL119, UL120, UL121, UL124, UL132, UL147A, UL148, UL142, UL144, UL141, UL140, UL135, UL136, UL138, UL139, UL133, UL135, UL148A, UL148B, UL148C, UL148D, US2, US3, US6, US7, USB, US9, US10, US11, US12, US13, US14, US15, US16, US17, US18, US19, US20, US21, US29, US30, or US34A.

The CMV antigen may also be a fusion polypeptide of one or more CMV proteins, such as pp65/IE1 (Reap et al., *Vaccine* (2007) 25:7441-7449), gH/gL (Chowdary et al., Nature Structural & Molecular Biology, 17, 882-888 (2010)).

Suitable CMV antigens include gB, gH, gL, gO, and can be from any CMV strain. For example, CMV proteins can be from Merlin, AD 169, VR1814, Towne, Toledo, TR, PH, TB40, or Fix strains of CMV. Exemplary sequences of CMV proteins that may be used for the invention are shown in Table 1.

TABLE 1

| | |
|---|---|
| Full length gH polynucleotide | (CMV gH FL) SEQ ID NO: 7 |
| Full length gH polypeptide | (CMV gH FL) SEQ ID NO: 8 |
| Full length gL polynucleotide | (CMV gL FL) SEQ ID NO: 11 |
| Full length gL polypeptide | (CMV gL FL) SEQ ID NO: 12 |
| Full length gO polynucleotide | (CMV gO FL) SEQ ID NO: 17 |
| Full length gO polypeptide | (CMV gO FL) SEQ ID NO: 18 |
| gH sol polynucleotide | (CMV gH sol) SEQ ID NO: 9 |
| gH sol polypeptide | (CMV gH sol) SEQ ID NO: 10 |
| Full length UL128 polynucleotide | (CMV UL128 FL) SEQ ID NO: 19 |
| Full length UL128 polypeptide | (CMV UL128 FL) SEQ ID NO: 20 |
| Full length UL130 polynucleotide | (CMV UL130 FL) SEQ ID NO: 21 |
| Full length UL130 polypeptide | (CMV UL130 FL) SEQ ID NO: 22 |
| Full length UL131 polynucleotide | (CMV UL131 FL) SEQ ID NO: 23 |
| Full length UL131 polypeptide | (CMV UL131 FL) SEQ ID NO: 24 |
| Full length gB polynucleotide | (CMV gB FL) SEQ ID NO: 1 |
| Full length gB polypeptide | (CMV gB FL) SEQ ID NO: 2 |
| gB sol 750 polynucleotide | (CMV gB 750) SEQ ID NO: 3 |
| gB sol 750 polypeptide | (CMV gB 750) SEQ ID NO: 4 |
| gB sol 692 polynucleotide | (CMV gB 692) SEQ ID NO: 5 |
| gB sol 692 polypeptide | (CMV gB 692) SEQ ID NO: 6 |
| Full length gM polynucleotide | (CMV gM FL) SEQ ID NO: 13 |
| Full length gM polypeptide | (CMV gM FL) SEQ ID NO: 14 |
| Full length gN polynucleotide | (CMV gN FL) SEQ ID NO: 15 |
| Full length gN polypeptide | (CMV gN FL) SEQ ID NO: 16 |

gB Antigens

In certain embodiments, the first or second antigen may be a gB antigen. A gB antigen can be full length gB protein or can omit one or more regions of the protein. Alternatively, fragments of a gB protein can be used. gB amino acids are numbered according to the full-length gB amino acid sequence (CMV gB FL) shown in SEQ ID NO: 2, which is 907 amino acids long. Suitable regions of a gB protein, which can be excluded from the full-length protein or included as fragments include: the signal sequence (amino acids 1-24), a gB-DLD disintegrin-like domain (amino acids 57-146), a furin cleavage site (amino acids 459-460), a heptad repeat region (679-693), a membrane spanning domain (amino acids 751-771), and a cytoplasmic domain from amino acids 771-906. In some embodiments, a gB antigen includes amino acids 67-86 (Neutralizing Epitope AD2) and/or amino acids 532-635 (Immunodominant Epitope AD1). Specific examples of gB antigens include “gB sol 692,” which includes the first 692 amino acids of gB, and “gB sol 750,” which includes the first 750 amino acids of gB. The signal sequence, amino acids 1-24, can be present or absent from gB sol 692 and gB sol 750 as desired.

In some embodiments, the gB antigen is a gB fragment of 10 amino acids or longer. For example, the number of amino acids in the fragment can comprise 10, 15, 20, 30, 40, 50, 60, 70, 80, 90, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, or 875 amino acids.

The invention may also use a gB antigen comprising an amino acid sequence that is at least 75% identical to SEQ ID NO: 2 (e.g., at least 80%, at least 85%, at least 90%, at least 95%, at least 97%, at least 98%, at least 99%, or 100% identical to SEQ ID NO: 2).

gH Antigens

In certain embodiments, the first or second antigen may be a gH antigen. A gH antigen can be a full-length gH protein (CMV gH FL, SEQ ID NO:8, for example, which is a 743 amino acid protein). gH has a membrane spanning domain and a cytoplasmic domain starting at position 716 to position 743. Removing amino acids from 717 to 743 provides a soluble gH (e.g., CMV gH sol, SEQ ID NO: 10).

In some embodiments, the gH antigen is a gH fragment of 10 amino acids or longer. For example, the number of amino acids in the fragment can comprise 10, 15, 20, 30, 40, 50, 60, 70, 80, 90, 100, 125, 150, 175, 200, 225, 250, 275, 300, 325, 350, 375, 400, 425, 450, 475, 500, 525, 550, 575, 600, 625, 650, 675, 700, or 725 amino acids.

The invention may also use a gH antigen comprising an amino acid sequence that is at least 75% identical to SEQ ID NO: 8 or 10 (e.g., at least 80%, at least 85%, at least 90%, at least 95%, at least 97%, at least 98%, at least 99%, or 100% identical to SEQ ID NO: 8 or 10).

gL Antigens

In certain embodiments, the first or second antigen may be a gL antigen. A gH antigen can be a full-length gL protein (CMV gL FL, SEQ ID NO:12, for example, which is a 278 amino acid protein). Alternatively, a gL fragment can be used. For example, the number of amino acids in the fragment can comprise 10, 15, 20, 30, 40, 50, 60, 70, 80, 90, 100, 125, 150, 175, 200, 225, or 250 amino acids.

The invention may also use a gL antigen comprising an amino acid sequence that is at least 75% identical to SEQ ID NO: 12 (e.g., at least 80%, at least 85%, at least 90%, at least 95%, at least 97%, at least 98%, at least 99%, or 100% identical to SEQ ID NO: 12).

gO Antigens

In certain embodiments, the first or second antigen may be a gO antigen. A gO antigen can be a full-length gO protein (CMV gO FL, SEQ ID NO:18, for example, which is a 472 amino acid protein). Alternatively, the gO antigen can be a gO fragment of 10 amino acids or longer. For example, the number of amino acids in the fragment can comprise 10, 15, 20, 30, 40, 50, 60, 70, 80, 90, 100, 125, 150, 175, 200, 225, 250, 275, 300, 325, 350, 375, 400, 425, or 450 amino acids.

The invention may also use a gO antigen comprising an amino acid sequence that is at least 75% identical to SEQ ID NO: 18 (e.g., at least 80%, at least 85%, at least 90%, at least 95%, at least 97%, at least 98%, at least 99%, or 100% identical to SEQ ID NO: 18).

gM Antigens

In certain embodiments, the first or second antigen may be a gM antigen. A gM antigen can be a full-length gM protein (CMV gM FL, SEQ ID NO:14, for example, which is a 371 amino acid protein). Alternatively, the gM antigen can be a gM fragment of 10 amino acids or longer. For example, the number of amino acids in the fragment can comprise 10, 15, 20, 30, 40, 50, 60, 70, 80, 90, 100, 125, 150, 175, 200, 225, 250, 275, 300, 325, or 350 amino acids.

The invention may also use a gM antigen comprising an amino acid sequence that is at least 75% identical to SEQ ID NO: 14 (e.g., at least 80%, at least 85%, at least 90%, at least 95%, at least 97%, at least 98%, at least 99%, or 100% identical to SEQ ID NO: 14).

gN Antigens

In certain embodiments, the first or second antigen may be a gN antigen. A gN antigen can be a full-length gN protein (CMV gN FL, SEQ ID NO:16, for example, which is a 135 amino acid protein). Alternatively, the gN antigen can be a gN fragment of 10 amino acids or longer. For example, the number of amino acids in the fragment can comprise 10, 15, 20, 30, 40, 50, 60, 70, 80, 90, 100, or 125 amino acids.

The invention may also use a gN antigen comprising an amino acid sequence that is at least 75% identical to SEQ ID NO: 16 (e.g., at least 80%, at least 85%, at least 90%, at least 95%, at least 97%, at least 98%, at least 99%, or 100% identical to SEQ ID NO: 16).

UL128 Antigens

In certain embodiments, the first or second antigen may be a UL128 antigen. A UL128 antigen can be a full-length UL128 protein (CMV UL128 FL, SEQ ID NO:20, for example, which is a 171 amino acid protein). Alternatively, the UL128 antigen can be a UL128 fragment of 10 amino acids or longer. For example, the number of amino acids in the fragment can comprise 10, 15, 20, 30, 40, 50, 60, 70, 80, 90, 100, 125, or 150 amino acids.

The invention may also use a UL128 antigen comprising an amino acid sequence that is at least 75% identical to SEQ ID NO: 20 (e.g., at least 80%, at least 85%, at least 90%, at least 95%, at least 97%, at least 98%, at least 99%, or 100% identical to SEQ ID NO: 20).

UL130 Antigens

In certain embodiments, the first or second antigen may be a UL130 antigen. A UL130 antigen can be a full-length UL130 protein (CMV UL130 FL, SEQ ID NO:22, for example, which is a 214 amino acid protein). Alternatively, the UL130 antigen can be a UL130 fragment of 10 amino acids or longer. For example, the number of amino acids in the fragment can comprise 10, 15, 20, 30, 40, 50, 60, 70, 80, 90, 100, 125, 150, 175, or 200 amino acids.

The invention may also use a UL130 antigen comprising an amino acid sequence that is at least 75% identical to SEQ ID NO: 22 (e.g., at least 80%, at least 85%, at least 90%, at least 95%, at least 97%, at least 98%, at least 99%, or 100% identical to SEQ ID NO: 22).

UL131 Antigens

In certain embodiments, the first or second antigen may be a UL131 antigen. A UL131 antigen can be a full-length UL131 protein (CMV UL131, SEQ ID NO:24, for example, which is a 129 amino acid protein). Alternatively, the UL131 antigen can be a UL131 fragment of 10 amino acids or longer. For example, the number of amino acids in the fragment can comprise 10, 15, 20, 30, 40, 50, 60, 70, 80, 90, 100, 125, 150, 175, or 200 amino acids.

The invention may also use a UL131 antigen comprising an amino acid sequence that is at least 75% identical to SEQ ID NO: 24 (e.g., at least 80%, at least 85%, at least 90%, at least 95%, at least 97%, at least 98%, at least 99%, or 100% identical to SEQ ID NO: 24).

The CMV antigen may be a fusion polypeptide. For example, the antigen may comprise a first domain and a second domain, wherein (i) the first domain comprises a first CMV antigen and (ii) the second domain comprises a second CMV antigen. The first CMV antigen and the second CMV antigen are independently selected from a gB, gH, gL, gO, gM, gN, UL128, UL130, or UL131 antigen described above.

Complexes

Two or more CMV antigens may also be co-delivered so that they form a complex in vivo (e.g., gH/gL complex, gM/gN complex, gH/gL/UL128/UL130/UL131 pentameric complex). For example, the immunogenic composition may comprise an RNA molecule that encode two separate antigens, gH and gL. The immunogenic composition may also comprise two polypeptide antigens, gH and gL.

2. Parvovirus

In certain embodiments, the polypeptide antigen is derived from Parvovirus. Preferrably, the parvovirus infects humans, i.e., is of the Dependovirus, Erythrovirus, or Bocavirus genus. In certain embodiments, the parvovirus is parvovirus B19. In some embodiments, the parvovirus is from the Parvovirus genus. Parvovirus B19 belongs to the Erythroviruses genus of the Parvoviridae family of small DNA viruses. It is a non-enveloped, icosahedral virus that contains a single-stranded linear DNA genome. The parvovirus B19 virion is 20-25 nm in diameter and has a genome of 5.6 kb (Clewley, 1984, Cotmore & Tattersall, 1984). The parvovirus B19 capsid consists of an 83 kDa minor structural protein, VP1, and a 58 kDa major structural protein, VP2. It has a non-segmented single stranded DNA genome surrounded by a protein shell containing two structural proteins, VP1 and VP2 in a ~5% to ~95% ratio (Ozawa et al., 1987). The sequences of the two proteins are co-linear, with VP2 being identical to the carboxyl-terminal region of VP 1; however, VP1 comprises an additional 227 amino acids at the amino-terminus Long lasting antibody responses are directed to both VP1 and VP2 proteins and thus these proteins alone are expected to raise a significant immune response.

The parvovirus B19 genome contains three open reading frames: a non-structural 77 kDa protein, NS1, is encoded by nucleotides 436-2451; the minor structural protein, VP1 is encoded by nucleotides 2444-4787, and the major structural protein, VP2, is encoded by nucleotides 3125-4787 (Corcoran et al., *J. Med. Microb.,* 2004). Parvovirus B19 uses a single promoter, p6, which is capable of expressing structural and non-structural genes differentially (Blundell et al., 1987, Ozawa et al., 1987). Although the foregoing numbering is relative to the nucleotide sequence of the parvovirus B19 genome, it is to be understood that the corresponding positions in sequences obtained from other genotypes and isolates of parvovirus are also intended to be encompassed by the present invention. Any one of the VP 1 or VP2 proteins, as well as variants thereof, such as immunogenic fragments thereof, and nucleic acids encoding such proteins can be used in the practice of the invention.

In certain embodiments, the Parvovirus antigen is a VLP. The VLP can contain VP1 and VP2 from any desired parvovirus, or any desired combination. In some embodiments the VP1 and VP2 proteins can have an amino acid sequence that is the same as or substantially the same as a naturally occurring parvovirus VP 1 or VP2, or can contain one or more amino acid substitutions, deletions or additions. For example, VP 1 can be mutated to inactivate its phospholipase activity. For example, the amino acid sequence of VP1 may contain a point mutation (e.g., His153A1a), or any of the mutations described in WO 06/032697, EP 1791858 or US 20070286870. Preferably, the VLP contains VP1 and VP2 are from a parvovirus that infects humans, i.e., a parvovirus of the Dependovirus, Erythrovirus, or Bocavirus genus. In certain embodiments, the VLP contains parvovirus B19 VP1 and parvovirus B19 VP2.

In certain embodiments, the VLP comprises VP1 in lower abundance relative to VP2 (e.g., soluble VP1 is produced in lower abundance than soluble VP2), as a result of the individual control elements that are operably linked to the nucleic acids that encode VP 1 and VP2 and/or as a result of other features of the recombinant nucleic acids that encode VP1 and VP2, such as optimized codon usage and deoptimized codon usage. Such control elements (e.g., promoters) and features (e.g., codon usage) allow for the relative production of VP 1 and VP2 to be controlled.

Exemplary sequences of Parvovirus proteins that may be used for the invention are shown in Table 2.

TABLE 2

| Parvovirus antigens | |
|---|---|
| Parvovirus B19 VP1 | (ParvoB19.Opti.VP1) polynucleotide SEQ ID NO: 25 (polypeptide encoded by the open reading fram shown in upper case in SEQ ID NO: 25) |
| Parvovirus B19 VP2 | (ParvoB19.Opti.VP2) polynucleotide SEQ ID NO: 26 (polypeptide encoded by the open reading fram shown in upper case in SEQ ID NO: 26) |

3. RSV

In some aspects, the pathogen is RSV. RSV is an enveloped non-segmented negative-strand RNA virus in the family Paramyxoviridae, genus Pneumovirus. To infect a host cell, paramyxoviruses such as RSV, like other enveloped viruses such as influenza virus and HIV, require fusion of the viral membrane with a host cell's membrane. For RSV, the conserved fusion protein (RSV-F glycoprotein) fuses the viral and cellular membranes by coupling irreversible protein refolding with juxtaposition of the membranes. In current models based on paramyxovirus studies, the RSV-F protein initially folds into a metastable "pre-fusion" conformation. During cell entry, the pre-fusion conformation undergoes refolding and conformational changes to its stable "post-fusion" conformation. See, also, Swanson et al., PNAS USA 108(23):9619-9624 (2011) regarding pre-fusion and post-fusion RSV-F structures.

In certain embodiments, the first and second antigens are from RSV. For example, the first and second antigens can independently be derived from the RSV surface glycoproteins Fusion (F), Glycoprotein (G), Small Hydrophobic protein (SH), the matrix proteins M and M2, the nucleocapsid proteins N, P and L, and the nonstructural proteins NS1 and NS2. In certain preferred embodiments, the first and second antigens are each an RSV-F antigen.

The F glycoprotein of RSV is a type I single-pass integral membrane protein having four general domains: N-terminal ER-translocating signal sequence (SS), ectodomain (ED), transmembrane domain (TM), and a cytoplasmic tail (CT). CT contains a single palmitoylated cysteine residue. The sequence of F protein is highly conserved among RSV isolates, but is constantly evolving (Kim et al. (2007) *J Med Virol* 79: 820-828). Unlike most paramyxoviruses, the F protein in RSV can mediate entry and syncytium formation independent of the other viral proteins (HN is usually necessary in addition to F in other paramyxoviruses).

The RSV-F glycoprotein is translated from mRNA into an approximately 574 amino acid protein designated $F_0$. Post-translational processing of $F_0$ includes removal of an N-terminal signal peptide by a signal peptidase in the endoplasmic reticulum. $F_0$ is also cleaved at two sites (approximately 109/110 and approximately 136/137) by cellular proteases (in particular furin) in the trans-Golgi. This cleavage results in the removal of a short intervening sequence and generates two subunits designated $F_1$ (~50 kDa; C-terminal; approximately residues 137-574) and $F_2$ (~20 kDa; N-terminal; approximately residues 1-109) that remain associated with each other. $F_1$ contains a hydrophobic fusion peptide at its N-terminus and also two amphipathic heptad-repeat regions (HRA and HRB). HRA is near the fusion peptide and HRB is near the transmembrane domain. Three $F_1$-$F_2$ heterodimers are assembled as homotrimers of $F_1$-$F_2$ in the virion.

RSV-F antigens suitable for inclusion in the immunogenic compositions described herein, either in RNA enconded form or as polypeptides, include RSV-F glycoprotein and RSV-F glycoprotein variants. Suitable RSV-F glycoprotein variants include, for example, full length F protein and truncated variants such as soluble ecto-domains, each optionally containing one or more mutations, such as furin-cleavage mutations, trypsin-cleavage mutations, fusion peptide mutations (e.g., deletions in whole or in part), mutations that stabilize the HRB trimer, and mutations that destabilize the HRA trimer.

Full length and truncated RSV-F glycoprotiens, including those with one or more such mutations in a variety of combinations are well known in the art and are disclosed for example in WO2011/008974, the disclosure of which is incorporated herein by reference in its entirety.

The skilled addressee is directed to the following sections of WO2011/008974 which disclose exemplary RSV-F antigens that can be used, in RNA form or as polypeptides, in the immunogenic compositions: (i) page 15, line 20 through page 16, line 27, which describes RSV-F, its amino acid sequence and domain structure; (ii) page 16, line 28 through page 18, line 11, which describes soluble ectodomains of RSV-F; (iii) page 18, line 14 through page 20, line 15, which describes furin-cleavage mutations, trypsin-cleavage mutations, fusion peptide mutations; (iv) page 20, line 16 through page 21, line 8, and page 26, line 29 through page 30, line 14, which describe optional oligomerization sequences; (v) page 20, lines 9-24, which describe introduced protease cleavage sites; (vi) and page 30, line 18 through page 32, line 18, which describe mutations that stabilize the HRB trimer, destabilize the HRA trimer and other mutations that can be included.

B. The RNA Molecule

The immunogenic composition described herein comprises an RNA component and a polypeptide component. Preferably, the RNA is a self-replicating RNA.

The composition can contain more than one RNA molecule encoding an antigen, e.g., two, three, five, ten or more RNA molecules. Alternatively or in addition, one RNA molecule may also encode more than one antigen, e.g., a bicistronic, or tricistronic RNA molecule that encodes different or identical antigens.

The sequence of the RNA molecule may be codon optimized or deoptimized for expression in a desired host, such as a human cell.

The sequence of the RNA molecule may be modified if desired, for example to increase the efficacy of expression or replication of the RNA, or to provide additional stability or resistance to degradation. For example, the RNA sequence can be modified with respect to its codon usage, for example, to increase translation efficacy and half-life of the RNA. A poly A tail (e.g., of about 30 adenosine residues or more) may be attached to the 3' end of the RNA to increase its half-life. The 5' end of the RNA may be capped with a modified ribonucleotide with the structure m7G (5') ppp (5') N (cap 0 structure) or a derivative thereof, which can be incorporated during RNA synthesis or can be enzymatically engineered after RNA transcription (e.g., by using Vaccinia Virus Capping Enzyme (VCE) consisting of mRNA triphosphatase, guanylyl-transferase and guanine-7-methytransferase, which catalyzes the construction of N7-monomethylated cap 0 structures). Cap 0 structure plays an important role in maintaining the stability and translational efficacy of the RNA molecule. The 5' cap of the RNA molecule may be further modified by a 2'-O-Methyltransferase which results in the generation of a cap 1 structure (m7Gppp[m2'-O]N), which may further increases translation efficacy.

If desired, the RNA molecule can comprise one or more modified nucleotides in addition to any 5' cap structure. There are more than 96 naturally occurring nucleoside modifications found on mammalian RNA. See, e.g., Limbach et al., *Nucleic Acids Research,* 22(12):2183-2196 (1994). The preparation of nucleotides and modified nucleotides and nucleosides are well-known in the art, e.g. from U.S. Pat. Nos. 4,373,071, 4,458,066, 4,500,707, 4,668,777, 4,973,679, 5,047,524, 5,132,418, 5,153,319, 5,262,530, 5,700,642 all of which are incorporated by reference in their entirety herein, and many modified nucleosides and modified nucleotides are commercially available.

Modified nucleobases which can be incorporated into modified nucleosides and nucleotides and be present in the RNA molecules include: m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2-1-O-methyladenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A(N6-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethyl cytidine); ac4Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-Omethyluridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-O-dimethyladenosine); rn62Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-($C_1$-$C_6$)-alkyluracil, 5-methyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-methylcytosine, 5-($C_2$-$C_6$)-alkenylcytosine, 5-($C_2$-$C_6$)-alkynylcytosine, 5-chlorocytosine, 5-fluorocytosine, 5-bromocytosine, dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, hydrogen (abasic residue), m5C, m5U, m6A, s2U, W, or 2'-O-methyl-U. Many of these modified nucleobases and their corresponding ribonucleosides are available from commercial suppliers. See, e.g., WO 2011/005799 which is incorporated herein by reference.

If desired, the RNA molecule can contain phosphoramidate, phosphorothioate, and/or methylphosphonate linkages.

In some embodiments, the RNA molecule does not include modified nucleotides, e.g., does not include modified nucleobases, and all of the nucleotides in the RNA molecule are conventional standard ribonucleotides A, U, G and C, with the exception of an optional 5' cap that may include, for example, 7-methylguanosine. In other embodiments, the RNA may include a 5' cap comprising a 7'-methylguanosine, and the first 1, 2 or 3 5' ribonucleotides may be methylated at the 2' position of the ribose.

Self-Replicating RNA

In some aspects, the cationic oil in water emulsion contains a self-replicating RNA molecule. In certain embodiments, the self-replicating RNA molecule is derived from or based on an alphavirus.

Self-replicating RNA molecules are well known in the art and can be produced by using replication elements derived from, e.g., alphaviruses, and substituting the structural viral proteins with a nucleotide sequence encoding a protein of interest. Cells transfected with self-replicating RNA briefly produce of antigen before undergoing apoptotic death. This death is a likely result of requisite double-stranded (ds) RNA intermediates, which also have been shown to super-activate Dendritic Cells. Thus, the enhanced immunogenicity of self-replicating RNA may be a result of the production of pro-inflammatory dsRNA, which mimics an RNA-virus infection of host cells.

Advantageously, the cell's machinery is used by self-replicating RNA molecules to generate an exponential increase of encoded gene products, such as proteins or antigens, which can accumulate in the cells or be secreted from the cells. Overexpression of proteins or antigens by self-replicating RNA molecules takes advantage of the immunostimulatory adjuvant effects, including stimulation of toll-like receptors (TLR) 3, 7 and 8 and non TLR pathways (e.g, RIG-1, MD-5) by the products of RNA replication and amplification, and translation which induces apoptosis of the transfected cell.

The self-replicating RNA generally contains at least one or more genes selected from the group consisting of viral replicases, viral proteases, viral helicases and other non-structural viral proteins, and also comprise 5'- and 3'-end cis-active replication sequences, and if desired, a heterologous sequences that encode a desired amino acid sequences (e.g., an antigen of interest). A subgenomic promoter that directs expression of the heterologous sequence can be included in the self-replicating RNA. If desired, the heterologous sequence (e.g., an antigen of interest) may be fused in frame to other coding regions in the self-replicating RNA and/or may be under the control of an internal ribosome entry site (IRES).

In certain embodiments, the self-replicating RNA molecule is not encapsulated in a virus-like particle. Self-replicating RNA molecules of the invention can be designed so that the self-replicating RNA molecule cannot induce production of infectious viral particles. This can be achieved, for example, by omitting one or more viral genes encoding structural proteins that are necessary for the production of viral particles in the self-replicating RNA. For example, when the self-replicating RNA molecule is based on an alpha virus, such as Sinebis virus (SIN), Semliki forest virus and Venezuelan equine encephalitis virus (VEE), one or more genes encoding viral structural proteins, such as capsid and/or envelope glycoproteins, can be omitted.

If desired, self-replicating RNA molecules of the invention can also be designed to induce production of infectious viral particles that are attenuated or virulent, or to produce viral particles that are capable of a single round of subsequent infection.

When delivered to a vertebrate cell, a self-replicating RNA molecule can lead to the production of multiple daughter RNAs by transcription from itself (or from an antisense copy of itself). The self-replicating RNA can be directly translated after delivery to a cell, and this translation provides a RNA-dependent RNA polymerase which then produces transcripts from the delivered RNA. Thus the delivered RNA leads to the production of multiple daughter RNAs. These transcripts are antisense relative to the delivered RNA and may be translated themselves to provide in situ expression of a gene product, or may be transcribed to provide further transcripts with the same sense as the delivered RNA which are translated to provide in situ expression of the gene product.

One suitable system for achieving self-replication is to use an alphavirus-based RNA replicon. Alphaviruses comprise a set of genetically, structurally, and serologically related arthropod-borne viruses of the Togaviridae family. Twenty-six known viruses and virus subtypes have been classified within the alphavirus genus, including, Sindbis virus, Semliki Forest virus, Ross River virus, and Venezuelan equine encephalitis virus. As such, the self-replicating RNA of the invention may incorporate a RNA replicase derived from semliki forest virus (SFV), sindbis virus (SIN), Venezuelan equine encephalitis virus (VEE), Ross-River virus (RRV), or other viruses belonging to the alphavirus family.

An alphavirus-based "replicon" expression vectors can be used in the invention. Replicon vectors may be utilized in several formats, including DNA, RNA, and recombinant replicon particles. Such replicon vectors have been derived from alphaviruses that include, for example, Sindbis virus (Xiong et al. (1989) Science 243:1188-1191; Dubensky et al., (1996) J. Virol. 70:508-519; Hariharan et al. (1998) J. Virol. 72:950-958; Polo et al. (1999) PNAS 96:4598-4603), Semliki Forest virus (Liljestrom (1991) Bio/Technology 9:1356-1361; Berglund et al. (1998) Nat. Biotech. 16:562-565), and Venezuelan equine encephalitis virus (Pushko et al. (1997) Virology 239:389-401). Alphaviruses-derived replicons are generally quite similar in overall characteristics (e.g., structure, replication), individual alphaviruses may exhibit some particular property (e.g., receptor binding, interferon sensitivity, and disease profile) that is unique. Therefore, chimeric alphavirus replicons made from divergent virus families may also be useful.

Alphavirus-based replicons are (+)-stranded replicons that can be translated after delivery to a cell to give of a replicase (or replicase-transcriptase). The replicase is translated as a polyprotein which auto-cleaves to provide a replication complex which creates genomic (−)-strand copies of the +-strand delivered RNA. These (−)-strand transcripts can themselves be transcribed to give further copies of the (+)-stranded parent RNA and also to give a subgenomic transcript which encodes the desired gene product. Translation of the subgenomic transcript thus leads to in situ expression of the desired gene product by the infected cell. Suitable alphavirus replicons can use a replicase from a sindbis virus, a semliki forest virus, an eastern equine encephalitis virus, a venezuelan equine encephalitis virus, etc.

A preferred self-replicating RNA molecule thus encodes (i) a RNA-dependent RNA polymerase which can transcribe RNA from the self-replicating RNA molecule and (ii) a polypeptide antigen. The polymerase can be an alphavirus replicase e.g. comprising alphavirus protein nsP4.

Whereas natural alphavirus genomes encode structural virion proteins in addition to the non-structural replicase, it is preferred that an alphavirus based self-replicating RNA molecule of the invention does not encode alphavirus structural proteins. Thus the self-replicating RNA can lead to the production of genomic RNA copies of itself in a cell, but not to the production of RNA-containing alphavirus virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self-replicating RNAs of the invention and their place is taken by gene(s) encoding the desired gene product, such that the subgenomic transcript encodes the desired gene product rather than the structural alphavirus virion proteins.

Thus a self-replicating RNA molecule useful with the invention may have two open reading frames. The first (5') open reading frame encodes a replicase; the second (3') open reading frame encodes a polypeptide antigen. In some embodiments the RNA may have additional (downstream) open reading frames e.g. that encode another desired gene products. A self-replicating RNA molecule can have a 5' sequence which is compatible with the encoded replicase.

In other aspects, the self-replicating RNA molecule is derived from or based on a virus other than an alphavirus, preferably, a positive-stranded RNA virus, and more preferably a picornavirus, flavivirus, rubivirus, pestivirus, hepacivirus, calicivirus, or coronavirus. Suitable wild-type alphavirus sequences are well-known and are available from sequence depositories, such as the American Type Culture Collection, Rockville, Md. Representative examples of suitable alphaviruses include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69, ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375).

The self-replicating RNA molecules of the invention are larger than other types of RNA (e.g. mRNA). Typically, the self-replicating RNA molecules of the invention contain at least about 4 kb. For example, the self-replicating RNA can contain at least about 5 kb, at least about 6 kb, at least about 7 kb, at least about 8 kb, at least about 9 kb, at least about 10 kb, at least about 11 kb, at least about 12 kb or more than 12 kb. In certain examples, the self-replicating RNA is about 4 kb to about 12 kb, about 5 kb to about 12 kb, about 6 kb to about 12 kb, about 7 kb to about 12 kb, about 8 kb to about 12 kb, about 9 kb to about 12 kb, about 10 kb to about 12 kb, about 11 kb to about 12 kb, about 5 kb to about 11 kb, about 5 kb to about 10 kb, about 5 kb to about 9 kb, about 5 kb to about 8 kb, about 5 kb to about 7 kb, about 5 kb to about 6 kb, about 6 kb to about 12 kb, about 6 kb to about 11 kb, about 6 kb to about 10 kb, about 6 kb to about 9 kb, about 6 kb to about 8 kb, about 6 kb to about 7 kb, about 7 kb to about 11 kb, about 7 kb to about 10 kb, about 7 kb to about 9 kb, about 7 kb to about 8 kb, about 8 kb to about 11 kb, about 8 kb to about 10 kb, about 8 kb to about 9 kb, about 9 kb to about 11 kb, about 9 kb to about 10 kb, or about 10 kb to about 11 kb.

The self-replicating RNA molecules of the invention may comprise one or more modified nucleotides (e.g., pseudouridine, N6-methyladenosine, 5-methylcytidine, 5-methyluridine).

The self-replicating RNA molecule may encode a single polypeptide antigen or, optionally, two or more of polypeptide antigens linked together in a way that each of the sequences retains its identity (e.g., linked in series) when expressed as an amino acid sequence. The polypeptides generated from the self-replicating RNA may then be produced as a fusion polypeptide or engineered in such a manner to result in separate polypeptide or peptide sequences.

The self-replicating RNA of the invention may encode one or more polypeptide antigens that contain a range of epitopes. Preferably epitopes capable of eliciting either a helper T-cell response or a cytotoxic T-cell response or both.

The self-replicating RNA molecules described herein may be engineered to express multiple nucleotide sequences, from two or more open reading frames, thereby allowing co-expression of proteins, such as a two or more antigens together with cytokines or other immunomodulators, which can enhance the generation of an immune response. Such a self-replicating RNA molecule might be particularly useful, for example, in the production of various gene products (e.g., proteins) at the same time, for example, as a bivalent or multivalent vaccine.

The self-replicating RNA molecules of the invention can be prepared using any suitable method. Several suitable methods are known in the art for producing RNA molecules that contain modified nucleotides. For example, a self-replicating RNA molecule that contains modified nucleotides can be prepared by transcribing (e.g., in vitro transcription) a DNA that encodes the self-replicating RNA molecule using a suitable DNA-dependent RNA polymerase, such as T7 phage RNA polymerase, SP6 phage RNA polymerase, T3 phage RNA polymerase, and the like, or mutants of these polymerases which allow efficient incorporation of modified nucleotides into RNA molecules. The transcription reaction will contain nucleotides and modified nucleotides, and other components that support the activity of the selected polymerase, such as a suitable buffer, and suitable salts. The incorporation of nucleotide analogs into a self-replicating RNA may be engineered, for example, to alter the stability of such RNA molecules, to increase resistance against RNases, to establish replication after introduction into appropriate host cells ("infectivity" of the RNA), and/or to induce or reduce innate and adaptive immune responses.

Suitable synthetic methods can be used alone, or in combination with one or more other methods (e.g., recombinant DNA or RNA technology), to produce a self-replicating RNA molecule of the invention. Suitable methods for de novo synthesis are well-known in the art and can be adapted for particular applications. Exemplary methods include, for example, chemical synthesis using suitable protecting groups such as CEM (Masuda et al., (2007) *Nucleic Acids Symposium Series* 51:3-4), the β-cyanoethyl phosphoramidite method (Beaucage S L et al. (1981) *Tetrahedron Lett* 22:1859); nucleoside H-phosphonate method (Garegg P et al. (1986) *Tetrahedron Lett* 27:4051-4; Froehler B C et al. (1986) *Nucl Acid Res* 14:5399-407; Garegg P et al. (1986) *Tetrahedron Lett* 27:4055-8; Gaffney B L et al. (1988) *Tetrahedron Lett* 29:2619-22). These chemistries can be performed or adapted for use with automated nucleic acid synthesizers that are commercially available. Additional suitable synthetic methods are disclosed in Uhlmann et al. (1990) *Chem Rev* 90:544-84, and Goodchild J (1990) *Bioconjugate Chem* 1: 165. Nucleic acid synthesis can also be performed using suitable recombinant methods that are well-known and conventional in the art, including cloning, processing, and/or expression of polynucleotides and gene products encoded by such polynucleotides. DNA shuffling by random fragmentation and PCR reassembly of gene fragments and synthetic polynucleotides are examples of known techniques that can be used to design and engineer polynucleotide sequences. Site-directed mutagenesis can be used to alter nucleic acids and the encoded proteins, for example, to insert new restriction sites, alter glycosylation patterns, change codon preference, produce splice variants, introduce mutations and the like. Suitable methods for transcription, translation and expression of nucleic acid sequences are known and conventional in the art. (See generally, Current Protocols in Molecular Biology, Vol. 2, Ed. Ausubel, et al., Greene Publish. Assoc. & Wiley Interscience, Ch. 13, 1988; Glover, DNA Cloning, Vol. II, IRL Press, Wash., D.C., Ch. 3, 1986; Bitter, et al., in Methods in Enzymology 153:516-544 (1987); The Molecular Biology of the Yeast *Saccharomyces*, Eds. Strathern et al., Cold Spring Harbor Press, Vols. I and II, 1982; and Sambrook et al., Molecular Cloning: A Laboratory Manual, Cold Spring Harbor Press, 1989.)

The presence and/or quantity of one or more modified nucleotides in a self-replicating RNA molecule can be determined using any suitable method. For example, a self-replicating RNA can be digested to monophosphates (e.g., using nuclease P1) and dephosphorylated (e.g., using a suitable phosphatase such as CIAP), and the resulting nucleosides analyzed by reversed phase HPLC (e.g., usings a YMC Pack ODS-AQ column (5 micron, 4.6×250 mm) and elute using a gradient, 30% B (0-5 min) to 100% B (5-13 min) and at 100% B (13-40) min, flow Rate (0.7 ml/min), UV detection (wavelength: 260 nm), column temperature (30° C.). Buffer A (20 mM acetic acid—ammonium acetate pH 3.5), buffer B (20 mM acetic acid—ammonium acetate pH 3.5/methanol[90/10])).

Optionally, the self-replicating RNA molecules of the invention may include one or more modified nucleotides so that the self-replicating RNA molecule will have less immunomodulatory activity upon introduction or entry into a host cell (e.g., a human cell) in comparison to the corresponding self-replicating RNA molecule that does not contain modified nucleotides.

If desired, the self-replicating RNA molecules can be screened or analyzed to confirm their therapeutic and prophylactic properties using various in vitro or in vivo testing methods that are known to those of skill in the art. For example, vaccines comprising self-replicating RNA molecule can be tested for their effect on induction of proliferation or effector function of the particular lymphocyte type of interest, e.g., B cells, T cells, T cell lines, and T cell clones. For example, spleen cells from immunized mice can be isolated and the capacity of cytotoxic T lymphocytes to lyse autologous target cells that contain a self replicating RNA molecule that encodes a polypeptide antigen. In addition, T helper cell differentiation can be analyzed by measuring proliferation or production of TH1 (IL-2 and IFN-γ) and/or TH2 (IL-4 and IL-5) cytokines by ELISA or directly in CD4+ T cells by cytoplasmic cytokine staining and flow cytometry.

Self-replicating RNA molecules that encode a polypeptide antigen can also be tested for ability to induce humoral immune responses, as evidenced, for example, by induction of B cell production of antibodies specific for an antigen of interest. These assays can be conducted using, for example, peripheral B lymphocytes from immunized individuals. Such assay methods are known to those of skill in the art. Other assays that can be used to characterize the self-replicating RNA molecules of the invention can involve detecting expression of the encoded antigen by the target cells. For example, FACS can be used to detect antigen expression on the cell surface or intracellularly. Another advantage of FACS selection is that one can sort for different levels of expression; sometimes-lower expression may be desired. Other suitable method for identifying cells which express a particular antigen involve panning using monoclonal antibodies on a plate or capture using magnetic beads coated with monoclonal antibodies.

The self-replicating RNA of the invention may be delivered by a variety of methods, such as naked RNA delivery or in combination with lipids, polymers or other compounds that facilitate entry into the cells. The RNA molecules of the present invention can be introduced into target cells or subjects using any suitable technique, e.g., by direct injection, microinjection, electroporation, lipofection, biolystics, and the like.

C. The Polypeptide Molecule

The immunogenic composition described herein comprises a polypeptide component and an RNA component. The polypeptide component may be a polypeptide complex or a VLP.

Suitable antigens that can be used as the polypeptide component (the "second polypeptide antigen") of the immunogenic composition include proteins and peptides from any pathogen, such as a bacterial pathogen, a viral pathogen, a fungal pathogen, a protozoan pathogen, or a multi-cellular parasitic pathogen. Exemplary antigens include any one of the antigens described above, such as an antigen derived from RSV, HIV, Parvovirus or CMV. The composition can contain more than one polypeptide antigen. Alternatively or in addition, the polypeptide may also be a fusion polypeptide comprising two or more epitopes from two different proteins of the same pathogen, or two or more epitopes from two different pathogens.

The polypeptide antigen may include additional sequences, such as a sequence to facilitate purification or detection (e.g., a poly-His sequence).

The polypeptide antigen will usually be isolated or purified. Thus, they will not be associated with molecules with which they are normally, if applicable, found in nature.

Polypeptides will usually be prepared by expression in a recombinant host system. Generally, they are produced by expression of recombinant constructs that encode the ectodomains in suitable recombinant host cells, although any suitable method can be used. Suitable recombinant host cells include, for example, insect cells (e.g., *Aedes aegypti, Autographa californica, Bombyx mori, Drosophila melanogaster, Spodoptera frugiperda*, and *Trichoplusia* m), mammalian cells (e.g., human, non-human primate, horse, cow, sheep, dog, cat, and rodent (e.g., hamster), avian cells (e.g., chicken, duck, and geese), bacteria (e.g., *E. coli, Bacillus subtilis*, and *Streptococcus* spp.), yeast cells (e.g., *Saccharomyces cerevisiae, Candida albicans, Candida maltosa, Hansenual polymorpha, Kluyveromyces fragilis, Kluyveromyces lactis, Pichia guillerimondii, Pichia pastoris, Schizosaccharomyces pombe* and *Yarrowia lipolytica*), Tetrahymena cells (e.g., Tetrahymena *thermophila*) or combinations thereof. Many suitable insect cells and mammalian cells are well-known in the art. Suitable insect cells include, for example, Sf9 cells, Sf21 cells, Tn5 cells, Schneider S2 cells, and High Five cells (a clonal isolate derived from the parental *Trichoplusia ni* BTI-TN-5B1-4 cell line (Invitrogen)). Suitable mammalian cells include, for example, Chinese hamster ovary (CHO) cells, human embryonic kidney cells (HEK293 cells, typically transformed by sheared adenovirus type 5 DNA), NIH-3T3 cells, 293-T cells, Vero cells, HeLa cells, PERC.6 cells (ECACC deposit number 96022940), Hep G2 cells, MRC-5 (ATCC CCL-171), WI-38 (ATCC CCL-75), fetal rhesus lung cells (ATCC CL-160), Madin-Darby bovine kidney ("MDBK") cells, Madin-Darby canine kidney ("MDCK") cells (e.g., MDCK (NBL2), ATCC CCL34; or MDCK 33016, DSM ACC 2219), baby hamster kidney (BHK) cells, such as BHK21-F, HKCC cells, and the like. Suitable avian cells include, for example, chicken embryonic stem cells (e.g., EBx® cells), chicken embryonic fibroblasts, chicken embryonic germ cells, duck cells (e.g., AGE1.CR and AGE1.CR.pIX cell lines (ProBioGen) which are described, for example, in Vaccine 27:4975-4982 (2009) and WO2005/042728), EB66 cells, and the like.

Suitable insect cell expression systems, such as baculovirus systems, are known to those of skill in the art and described in, e.g., Summers and Smith, Tex. *Agricultural Experiment Station Bulletin* No. 1555 (1987). Materials and methods for baculovirus/insect cell expression systems are commercially available in kit form from, inter alia, Invitrogen, San Diego Calif. Avian cell expression systems are also known to those of skill in the art and described in, e.g., U.S. Pat. Nos. 5,340,740; 5,656,479; 5,830,510; 6,114,168; and 6,500,668; European Patent No. EP 0787180B; European Patent Application No. EP03291813.8; WO 03/043415; and WO 03/076601. Similarly, bacterial and mammalian cell expression systems are also known in the art and described in, e.g., *Yeast Genetic Engineering* (Barr et al., eds., 1989) Butterworths, London.

Recombinant constructs encoding a polypeptide can be prepared in suitable vectors using conventional methods. A number of suitable vectors for expression of recombinant proteins in insect or mammalian cells are well-known and conventional in the art. Suitable vectors can contain a number of components, including, but not limited to one or more of the following: an origin of replication; a selectable marker gene; one or more expression control elements, such as a transcriptional control element (e.g., a promoter, an enhancer, a terminator), and/or one or more translation signals; and a signal sequence or leader sequence for targeting to the secretory pathway in a selected host cell (e.g., of mammalian origin or from a heterologous mammalian or non-mammalian species). For example, for expression in insect cells a suitable baculovirus expression vector, such as pFastBac (Invitrogen), is used to produce recombinant baculovirus particles. The baculovirus particles are amplified and used to infect insect cells to express recombinant protein. For expression in mammalian cells, a vector that will drive expression of the construct in the desired mammalian host cell (e.g., Chinese hamster ovary cells) is used.

Polypeptides can be purified using any suitable methods. For example, methods for purifying polypeptides by immunoaffinity chromatography are known in the art. Ruiz-Arguello et al., *J. Gen. Virol.,* 85:3677-3687 (2004). Suitable methods for purifying desired proteins including precipitation and various types of chromatography, such as hydrophobic interaction, ion exchange, affinity, chelating and size exclusion are well-known in the art. Suitable purification schemes can be created using two or more of these or other suitable methods. If desired, the polypeptides can include a "tag" that facilitates purification, such as an epitope tag or a HIS tag. Such tagged polypeptides can conveniently be purified, for example from conditioned media, by chelating chromatography or affinity chromatography.

D. Optional RNA Delivery Systems

In addition to the protein compontent and the RNA component, additional components, such as lipids, polymers or other compounds may be optionally included in the immunogenic composition as described herein to facilitate the entry of RNA into target cells.

Although RNA can be delivered as naked RNA (e.g. merely as an aqueous solution of RNA), to enhance entry into cells and also subsequent intercellular effects, the RNA molecule is preferably administered in combination with a delivery system, such as a particulate or emulsion delivery system. A large number of delivery systems are well known to those of skill in the art.

For example, the RNA molecule may be introduced into cells by way of receptor-mediated endocytosis. See e.g., U.S. Pat. No. 6,090,619; Wu and Wu, J. Biol. Chem., 263:14621 (1988); and Curiel et al., Proc. Natl. Acad. Sci. USA, 88:8850 (1991). For example, U.S. Pat. No. 6,083,741 discloses introducing an exogenous nucleic acid into mammalian cells by associating the nucleic acid to a polycation moiety (e.g., poly-L-lysine having 3-100 lysine residues), which is itself coupled to an integrin receptor-binding moiety (e.g., a cyclic peptide having the sequence Arg-Gly-Asp).

The RNA molecule of the present invention can be delivered into cells via amphiphiles. See e.g., U.S. Pat. No. 6,071,890. Typically, a nucleic acid molecule may form a complex with the cationic amphiphile. Mammalian cells contacted with the complex can readily take it up.

Three particularly useful delivery systems are (i) liposomes (ii) non-toxic and biodegradable polymer microparticles (iii) cationic submicron oil-in-water emulsions.

1. Liposomes

Various amphiphilic lipids can form bilayers in an aqueous environment to encapsulate a RNA-containing aqueous core as a liposome. These lipids can have an anionic, cationic or zwitterionic hydrophilic head group. Formation of liposomes from anionic phospholipids dates back to the 1960s, and cationic liposome-forming lipids have been studied since the 1990s. Some phospholipids are anionic whereas other are zwitterionic. Suitable classes of phospholipid include, but are not limited to, phosphatidylethanolamines, phosphatidylcholines, phosphatidylserines, and phosphatidylglycerols, and some useful phospholipids are listed in Table 2. Useful cationic lipids include, but are not limited to, dioleoyl trimethylammonium propane (DOTAP), 1,2-distearyloxy-N,N-dimethyl-3-aminopropane (DSDMA), 1,2-dioleyloxy-N,Ndimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA). Zwitterionic lipids include, but are not limited to, acyl zwitterionic lipids and ether zwitterionic lipids. Examples of useful zwitterionic lipids are DPPC, DOPC and dodecylphosphocholine. The lipids can be saturated or unsaturated.

TABLE 2

| Phospholipids | |
|---|---|
| DDPC | 1,2-Didecanoyl-sn-Glycero-3-phosphatidylcholine |
| DEPA | 1,2-Dierucoyl-sn-Glycero-3-Phosphate |
| DEPC | 1,2-Erucoyl-sn-Glycero-3-phosphatidylcholine |
| DEPE | 1,2-Dierucoyl-sn-Glycero-3-phosphatidylethanolamine |
| DEPG | 1,2-Dierucoyl-sn-Glycero-3[Phosphatidyl-rac-(1-glycerol . . . ) |
| DLOPC | 1,2-Linoleoyl-sn-Glycero-3-phosphatidylcholine |
| DLPA | 1,2-Dilauroyl-sn-Glycero-3-Phosphate |
| DLPC | 1,2-Dilauroyl-sn-Glycero-3-phosphatidylcholine |
| DLPE | 1,2-Dilauroyl-sn-Glycero-3-phosphatidylethanolamine |
| DLPG | 1,2-Dilauroyl-sn-Glycero-3[Phosphatidyl-rac-(1-glycerol . . . ) |
| DLPS | 1,2-Dilauroyl-sn-Glycero-3-phosphatidylserine |
| DMG | 1,2-Dimyristoyl-sn-glycero-3-phosphoethanolamine |
| DMPA | 1,2-Dimyristoyl-sn-Glycero-3-Phosphate |
| DMPC | 1,2-Dimyristoyl-sn-Glycero-3-phosphatidylcholine |
| DMPE | 1,2-Dimyristoyl-sn-Glycero-3-phosphatidylethanolamine |
| DMPG | 1,2-Myristoyl-sn-Glycero-3[Phosphatidyl-rac-(1-glycerol . . . ) |
| DMPS | 1,2-Dimyristoyl-sn-Glycero-3-phosphatidylserine |
| DOPA | 1,2-Dioleoyl-sn-Glycero-3-Phosphate |
| DOPC | 1,2-Dioleoyl-sn-Glycero-3-phosphatidylcholine |
| DOPE | 1,2-Dioleoyl-sn-Glycero-3-phosphatidylethanolamine |
| DOPG | 1,2-Dioleoyl-sn-Glycero-3[Phosphatidyl-rac-(1-glycerol . . . ) |
| DOPS | 1,2-Dioleoyl-sn-Glycero-3-phosphatidylserine |
| DPPA | 1,2-Dipalmitoyl-sn-Glycero-3-Phosphate |
| DPPC | 1,2-Dipalmitoyl-sn-Glycero-3-phosphatidylcholine |
| DPPE | 1,2-Dipalmitoyl-sn-Glycero-3-phosphatidylethanolamine |

TABLE 2-continued

| Phospholipids | |
|---|---|
| DPPG | 1,2-Dipalmitoyl-sn-Glycero-3[Phosphatidyl-rac-(1-glycerol . . . ) |
| DPPS | 1,2-Dipalmitoyl-sn-Glycero-3-phosphatidylserine |
| DPyPE | 1,2-diphytanoyl-sn-glycero-3-phosphoethanolamine |
| DSPA | 1,2-Distearoyl-sn-Glycero-3-Phosphate |
| DSPC | 1,2-Distearoyl-sn-Glycero-3-phosphatidylcholine |
| DSPE | 1,2-Distearpyl-sn-Glycero-3-phosphatidylethanolamine |
| DSPG | 1,2-Distearoyl-sn-Glycero-3[Phosphatidyl-rac-(1-glycerol . . . ) |
| DSPS | 1,2-Distearoyl-sn-Glycero-3-phosphatidylserine |
| EPC | Egg-PC |
| HEPC | Hydrogenated Egg PC |
| HSPC | High purity Hydrogenated Soy PC |
| HSPC | Hydrogenated Soy PC |
| LYSOPC MYRISTIC | 1-Myristoyl-sn-Glycero-3-phosphatidylcholine |
| LYSOPC PALMITIC | 1-Palmitoyl-sn-Glycero-3-phosphatidylcholine |
| LYSOPC STEARIC | 1-Stearoyl-sn-Glycero-3-phosphatidylcholine |
| Milk Sphingomyelin MPPC | 1-Myristoyl,2-palmitoyl-sn-Glycero 3-phosphatidylcholine |
| MSPC | 1-Myristoyl,2-stearoyl-sn-Glycero-3-phosphatidylcholine |
| PMPC | 1-Palmitoyl,2-myristoyl-sn-Glycero-3-phosphatidylcholine |
| POPC | 1-Palmitoyl,2-oleoyl-sn-Glycero-3-phosphatidylcholine |
| POPE | 1-Palmitoyl-2-oleoyl-sn-Glycero-3-phosphatidylethanolamine |
| POPG | 1,2-Dioleoyl-sn-Glycero-3[Phosphatidyl-rac-(1-glycerol) . . . ] |
| PSPC | 1-Palmitoyl,2-stearoyl-sn-Glycero-3-phosphatidylcholine |
| SMPC | 1-Stearoyl,2-myristoyl-sn-Glycero-3-phosphatidylcholine |
| SOPC | 1-Stearoyl,2-oleoyl-sn-Glycero-3-phosphatidylcholine |
| SPPC | 1-Stearoyl,2-palmitoyl-sn-Glycero-3-phosphatidylcholine |

Liposomes can be formed from a single lipid or from a mixture of lipids. A mixture may comprise (i) a mixture of anionic lipids (ii) a mixture of cationic lipids (iii) a mixture of zwitterionic lipids (iv) a mixture of anionic lipids and cationic lipids (v) a mixture of anionic lipids and zwitterionic lipids (vi) a mixture of zwitterionic lipids and cationic lipids or (vii) a mixture of anionic lipids, cationic lipids and zwitterionic lipids. Similarly, a mixture may comprise both saturated and unsaturated lipids. For example, a mixture may comprise DSPC (zwitterionic, saturated), DlinDMA (cationic, unsaturated), and/or DMPG (anionic, saturated). Where a mixture of lipids is used, not all of the component lipids in the mixture need to be amphiphilic e.g. one or more amphiphilic lipids can be mixed with cholesterol.

The hydrophilic portion of a lipid can be PEGylated (i.e. modified by covalent attachment of a polyethylene glycol). This modification can increase stability and prevent non-specific adsorption of the liposomes. For instance, lipids can be conjugated to PEG using techniques such as those disclosed in Heyes et al. (2005) *J Controlled Release* 107: 276-87.

A mixture of DSPC, DlinDMA, PEG-DMPG and cholesterol is used in the examples. A separate aspect of the invention is a liposome comprising DSPC, DlinDMA, PEG-DMG and cholesterol. This liposome preferably encapsulates RNA, such as a self-replicating RNA e.g. encoding an immunogen.

Liposomes are usually divided into three groups: multilamellar vesicles (MLV); small unilamellar vesicles (SUV); and large unilamellar vesicles (LUV). MLVs have multiple bilayers in each vesicle, forming several separate aqueous compartments. SUVs and LUVs have a single bilayer encapsulating an aqueous core; SUVs typically have a diameter≤50 nm, and LUVs have a diameter>50 nm. Liposomes useful with of the invention are ideally LUVs with a diameter in the range of 50-220 nm. For a composition comprising a population of LUVs with different diameters: (i) at least 80% by number should have diameters in the range of 20-220 nm, (ii) the average diameter (Zav, by intensity) of the population is ideally in the range of 40-200 nm, and/or (iii) the diameters should have a polydispersity index<0.2.

Techniques for preparing suitable liposomes are well known in the art e.g. see Liposomes: Methods and Protocols, Volume 1: Pharmaceutical Nanocarriers: Methods and Protocols. (ed. Weissig). Humana Press, 2009. ISBN 160327359X; Liposome Technology, volumes I, II & III. (ed. Gregoriadis). Informa Healthcare, 2006; and Functional Polymer Colloids and Microparticles volume 4 (Microspheres, microcapsules & liposomes). (eds. Arshady & Guyot). Citus Books, 2002. One useful method involves mixing (i) an ethanolic solution of the lipids (ii) an aqueous solution of the nucleic acid and (iii) buffer, followed by mixing, equilibration, dilution and purification (Heyes et al. (2005) *J Controlled Release* 107:276-87.).

RNA is preferably encapsulated within the liposomes, and so the liposome forms a outer layer around an aqueous RNA-containing core. This encapsulation has been found to protect RNA from RNase digestion. The liposomes can include some external RNA (e.g. on the surface of the liposomes), but at least half of the RNA (and ideally all of it) is encapsulated.

2. Polymeric Microparticles

Various polymers can form microparticles to encapsulate or adsorb RNA. The use of a substantially non-toxic polymer means that a recipient can safely receive the particles, and the use of a biodegradable polymer means that the particles can be metabolised after delivery to avoid long-term persistence. Useful polymers are also sterilisable, to assist in preparing pharmaceutical grade formulations.

Suitable non-toxic and biodegradable polymers include, but are not limited to, poly(α-hydroxy acids), polyhydroxy butyric acids, polylactones (including polycaprolactones), polydioxanones, polyvalerolactone, polyorthoesters, polyanhydrides, polycyanoacrylates, tyrosine-derived polycarbonates, polyvinyl-pyrrolidinones or polyester-amides, and combinations thereof.

In some embodiments, the microparticles are formed from poly(α-hydroxy acids), such as a poly(lactides) ("PLA"), copolymers of lactide and glycolide such as a poly(D,L-lactide-co-glycolide) ("PLG"), and copolymers of D,L-lactide and caprolactone. Useful PLG polymers include those having a lactide/glycolide molar ratio ranging, for example, from 20:80 to 80:20 e.g. 25:75, 40:60, 45:55, 55:45, 60:40, 75:25. Useful PLG polymers include those having a molecular weight between, for example, 5,000-200,000 Da e.g. between 10,000-100,000, 20,000-70,000, 40,000-50,000 Da.

The microparticles ideally have a diameter in the range of 0.02 μm to 8 μm. For a composition comprising a population of microparticles with different diameters at least 80% by number should have diameters in the range of 0.03-7 μm.

Techniques for preparing suitable microparticles are well known in the art e.g. see Functional Polymer Colloids and Microparticles volume 4 (Microspheres, microcapsules & liposomes). (eds. Arshady & Guyot). Citus Books, 2002; *Polymers in Drug Delivery*. (eds. Uchegbu & Schatzlein). CRC Press, 2006. (in particular chapter 7) and *Microparticulate Systems for the Delivery of Proteins and Vaccines*. (eds. Cohen & Bernstein). CRC Press, 1996. To facilitate adsorption of RNA, a microparticle may include a cationic surfactant and/or lipid e.g. as disclosed in O'Hagan et al. (2001) *J Virology* 75:9037-9043; and Singh et al. (2003) *Pharmaceutical Research* 20: 247-251. An alternative way of making polymeric microparticles is by molding and curing e.g. as disclosed in WO2009/132206.

Microparticles of the invention can have a zeta potential of between 40-100 mV.

RNA can be adsorbed to the microparticles, and adsorption is facilitated by including cationic materials (e.g. cationic lipids) in the microparticle.

3. Oil-in-Water Cationic Emulsions

Oil-in-water emulsions are known for adjuvanting influenza vaccines e.g. the MF59™ adjuvant in the FLUAD™ product, and the AS03 adjuvant in the PREPANDRIX™ product. RNA delivery according to the present invention can utilise an oil-in-water emulsion, provided that the emulsion includes one or more cationic molecules. For instance, a cationic lipid can be included in the emulsion to provide a positive droplet surface to which negatively-charged RNA can attach.

The emulsion comprises one or more oils. Suitable oil(s) include those from, for example, an animal (such as fish) or a vegetable source. The oil is ideally biodegradable (metabolisable) and biocompatible. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and so may be used. The procedures for separation, purification, saponification and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Squalene can also be obtained from yeast or other suitable microbes. In some embodiments, Squalene is preferably obtained from non-animal sources, such as from olives, olive oil or yeast. Squalane, the saturated analog to squalene, can also be used. Fish oils, including squalene and squalane, are readily available from commercial sources or may be obtained by methods known in the art.

Other useful oils are the tocopherols, particularly in combination with squalene. Where the oil phase of an emulsion includes a tocopherol, any of the α, β, γ, δ, ε or ξ tocopherols can be used, but α-tocopherols are preferred. D-α-tocopherol and DL-α-tocopherol can both be used. A preferred α-tocopherol is DL-α-tocopherol. An oil combination comprising squalene and a tocopherol (e.g. DL-α-tocopherol) can be used.

Preferred emulsions comprise squalene, a shark liver oil which is a branched, unsaturated terpenoid ($C_{30}H_{50}$; $[(CH_3)_2C[{=}CHCH_2CH_2C(CH_3)]_2{=}CHCH_2{-}]_2$; 2,6,10,15,19,23-hexamethyl-2,6,10,14,18,22-tetracosahexaene; CAS RN 7683-64-9).

The oil in the emulsion may comprise a combination of oils e.g. squalene and at least one further oil.

The aqueous component of the emulsion can be plain water (e.g. w.f.i.) or can include further components e.g. solutes. For instance, it may include salts to form a buffer e.g. citrate or phosphate salts, such as sodium salts. Typical buffers include: a phosphate buffer; a Tris buffer; a borate buffer; a succinate buffer; a histidine buffer; or a citrate buffer. A buffered aqueous phase is preferred, and buffers will typically be included in the 5-20 mM range.

The emulsion also includes a cationic lipid. Preferably this lipid is a surfactant so that it can facilitate formation and stabilisation of the emulsion. Useful cationic lipids generally contains a nitrogen atom that is positively charged under physiological conditions e.g. as a tertiary or quaternary amine. This nitrogen can be in the hydrophilic head group of an amphiphilic surfactant. Useful cationic lipids include, but are not limited to: 1,2-dioleoyloxy-3-(trimethylammonio) propane (DOTAP), 3'-[N-(N',N'-Dimethylaminoethane)-carbamoyl]Cholesterol (DC Cholesterol), dimethyldioctadecyl-ammonium (DDA e.g. the bromide), 1,2-Dimyristoyl-3-Trimethyl-AmmoniumPropane (DMTAP), dipalmitoyl (C16:0)trimethyl ammonium propane (DPTAP), distearoyltrimethylammonium propane (DSTAP). Other useful cationic lipids are: benzalkonium chloride (BAK), benzethonium chloride, cetramide (which contains tetradecyltrimethylammonium bromide and possibly small amounts of dedecyltrimethylammonium bromide and hexadecyltrimethyl ammonium bromide), cetylpyridinium chloride (CPC), cetyl trimethylammonium chloride (CTAC), N,N',N'-polyoxyethylene (10)-N-tallow-1,3-diaminopropane, dodecyltrimethylammonium bromide, hexadecyltrimethyl-ammonium bromide, mixed alkyl-trimethyl-ammonium bromide, benzyldimethyldodecylammonium chloride, benzyldimethylhexadecyl-ammonium chloride, benzyltrimethylammonium methoxide, cetyldimethylethylammonium bromide, dimethyldioctadecyl ammonium bromide (DDAB), methylbenzethonium chloride, decamethonium chloride, methyl mixed trialkyl ammonium chloride, methyl trioctylammonium chloride), N,N-dimethyl-N-[2 (2-methyl-4-(1,1,3,3tetramethylbutyl)-phenoxy]-ethoxy)ethyl]-benzenemetha-naminium chloride (DEBDA), dialkyldimetylammonium salts, [1-(2,3-dioleyloxy)-propyl]-N,N,N, trimethylammonium chloride, 1,2-diacyl-3-(trimethylammonio) propane (acyl group=dimyristoyl, dipalmitoyl, distearoyl, dioleoyl), 1,2-diacyl-3 (dimethylammonio)propane (acyl group=dimyristoyl, dipalmitoyl, distearoyl, dioleoyl), 1,2-dioleoyl-3-(4'-trimethyl-ammonio) butanoyl-sn-glycerol, 1,2-dioleoyl 3-succinyl-sn-glycerol choline ester, cholesteryl (4'-trimethylammonio) butanoate), N-alkyl pyridinium salts (e.g. cetylpyridinium bromide and cetylpyridinium chloride), N-alkylpiperidinium salts, dicationic bolaform electrolytes (C12Me6; C12BU6), dialkylglycetylphosphorylcholine, lysolecithin, L-α dioleoylphosphatidylethanolamine, cholesterol hemisuccinate choline ester, lipopolyamines, including but not limited to dioctadecylamidoglycylspermine (DOGS), dipalmitoyl phosphatidylethanol-amidospermine (DPPES), lipopoly-L (or D)-lysine (LPLL, LPDL), poly (L (or D)-lysine conjugated to N-glutarylphosphatidylethanolamine, didodecyl glutamate ester with pendant amino group (C^GluPhCnN), ditetradecyl glutamate ester with pendant amino group (Cl4GluCnN+), cationic derivatives of cholesterol, including but not limited to cholesteryl-3β-oxysuccinamidoethylenetrimethylammonium salt, cholesteryl-3β-oxysuccinamidoethylene-dimethylamine, cholesteryl-3β-carboxyamidoethylenetrimethylammonium salt, and cholesteryl-3β-carboxyamidoethylenedimethylamine Other useful cationic lipids are described in US 2008/0085870 and US 2008/0057080, which are incorporated herein by reference.

The cationic lipid is preferably biodegradable (metabolisable) and biocompatible.

In addition to the oil and cationic lipid, an emulsion can include a non-ionic surfactant and/or a zwitterionic surfactant. Such surfactants include, but are not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); polyoxyethylene-9-lauryl ether; and sorbitan esters (commonly known as the Spans), such as sorbitan trioleate (Span 85) and sorbitan monolaurate. Preferred surfactants for including in the emulsion are polysorbate 80 (Tween 80; polyoxyethylene sorbitan monooleate), Span 85 (sorbitan trioleate), lecithin and Triton X-100.

Mixtures of these surfactants can be included in the emulsion e.g. Tween 80/Span 85 mixtures, or Tween 80/Triton-X100 mixtures. A combination of a polyoxyethylene sorbitan ester such as polyoxyethylene sorbitan monooleate (Tween 80) and an octoxynol such as t-octylphenoxy-polyethoxyethanol (Triton X-100) is also suitable. Another useful combination comprises laureth 9 plus a polyoxyethylene sorbitan ester and/or an octoxynol. Useful mixtures can comprise a surfactant with a HLB value in the range of 10-20 (e.g. polysorbate 80, with a HLB of 15.0) and a surfactant with a HLB value in the range of 1-10 (e.g. sorbitan trioleate, with a HLB of 1.8).

Preferred amounts of oil (% by volume) in the final emulsion are between 2-20% e.g. 5-15%, 6-14%, 7-13%, 8-12%. A squalene content of about 4-6% or about 9-11% is particularly useful.

Preferred amounts of surfactants (% by weight) in the final emulsion are between 0.001% and 8%. For example: polyoxyethylene sorbitan esters (such as polysorbate 80) 0.2 to 4%, in particular between 0.4-0.6%, between 0.45-0.55%, about 0.5% or between 1.5-2%, between 1.8-2.2%, between 1.9-2.1%, about 2%, or 0.85-0.95%, or about 1%; sorbitan esters (such as sorbitan trioleate) 0.02 to 2%, in particular about 0.5% or about 1%; octyl- or nonylphenoxy polyoxyethanols (such as Triton X-100) 0.001 to 0.1%, in particular 0.005 to 0.02%; polyoxyethylene ethers (such as laureth 9) 0.1 to 8%, preferably 0.1 to 10% and in particular 0.1 to 1% or about 0.5%.

The absolute amounts of oil and surfactant, and their ratio, can be varied within wide limits while still forming an emulsion. A skilled person can easily vary the relative proportions of the components to obtain a desired emulsion, but a weight ratio of between 4:1 and 5:1 for oil and surfactant is typical (excess oil).

An important parameter for ensuring immunostimulatory activity of an emulsion, particularly in large animals, is the oil droplet size (diameter). The most effective emulsions have a droplet size in the submicron range. Suitably the droplet sizes will be in the range 50-750 nm. Most usefully the average droplet size is less than 250 nm e.g. less than 200 nm, less than 150 nm. The average droplet size is usefully in the range of 80-180 nm. Ideally, at least 80% (by number) of the emulsion's oil droplets are less than 250 nm in diameter, and preferably at least 90%. Apparatuses for determining the average droplet size in an emulsion, and the size distribution, are commercially available. These these typically use the techniques of dynamic light scattering and/or single-particle optical sensing e.g. the Accusizer™ and Nicomp™ series of instruments available from Particle Sizing Systems (Santa Barbara, USA), or the Zetasizer™ instruments from Malvern Instruments (UK), or the Particle Size Distribution Analyzer instruments from Horiba (Kyoto, Japan).

Ideally, the distribution of droplet sizes (by number) has only one maximum i.e. there is a single population of droplets distributed around an average (mode), rather than having two maxima. Preferred emulsions have a polydispersity of <0.4 e.g. 0.3, 0.2, or less.

Suitable emulsions with submicron droplets and a narrow size distribution can be obtained by the use of microfluidisation. This technique reduces average oil droplet size by propelling streams of input components through geometrically fixed channels at high pressure and high velocity. These streams contact channel walls, chamber walls and each other. The results shear, impact and cavitation forces cause a reduction in droplet size. Repeated steps of microfluidisation can be performed until an emulsion with a desired droplet size average and distribution are achieved.

As an alternative to microfluidisation, thermal methods can be used to cause phase inversion. These methods can also provide a submicron emulsion with a tight particle size distribution.

Preferred emulsions can be filter sterilised i.e. their droplets can pass through a 220 nm filter. As well as providing a sterilisation, this procedure also removes any large droplets in the emulsion.

In certain embodiments, the cationic lipid in the emulsion is DOTAP. The cationic oil-in-water emulsion may comprise from about 0.5 mg/ml to about 25 mg/ml DOTAP. For example, the cationic oil-in-water emulsion may comprise DOTAP at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.6 mg/ml, from about 0.7 mg/ml to about 1.6 mg/ml, from about 0.8 mg/ml to about 1.6 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 12 mg/ml, about 18 mg/ml, about 20 mg/ml, about 21.8 mg/ml, about 24 mg/ml, etc. In an exemplary embodiment, the cationic oil-in-water emulsion comprises from about 0.8 mg/ml to about 1.6 mg/ml DOTAP, such as 0.8 mg/ml, 1.2 mg/ml, 1.4 mg/ml or 1.6 mg/ml.

In certain embodiments, the cationic lipid is DC Cholesterol. The cationic oil-in-water emulsion may comprise DC Cholesterol at from about 0.1 mg/ml to about 5 mg/ml DC Cholesterol. For example, the cationic oil-in-water emulsion may comprise DC Cholesterol from about 0.1 mg/ml to about 5 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.62 mg/ml to about 5 mg/ml, from about 1 mg/ml to about 5 mg/ml, from about 1.5 mg/ml to about 5 mg/ml, from about 2 mg/ml to about 5 mg/ml, from about 2.46 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, from about 0.1 mg/ml to about 4.92 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.46 mg/ml, from about 0.1 mg/ml to about 2 mg/ml, from about 0.1 mg/ml to about 1.5 mg/ml, from about 0.1 mg/ml to about 1 mg/ml, from about 0.1 mg/ml to about 0.62 mg/ml, about 0.15 mg/ml, about 0.3 mg/ml, about 0.6 mg/ml, about 0.62 mg/ml, about 0.9 mg/ml, about 1.2 mg/ml, about 2.46 mg/ml, about 4.92 mg/ml, etc. In an exemplary embodiment, the cationic oil-in-water emulsion comprises from about 0.62 mg/ml to about 4.92 mg/ml DC Cholesterol, such as 2.46 mg/ml.

In certain embodiments, the cationic lipid is DDA. The cationic oil-in-water emulsion may comprise from about 0.1 mg/ml to about 5 mg/ml DDA. For example, the cationic oil-in-water emulsion may comprise DDA at from about 0.1 mg/ml to about 5 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.5 mg/ml, from about 0.1 mg/ml to about 2 mg/ml, from about 0.1 mg/ml to about 1.5 mg/ml, from about 0.1 mg/ml to about 1.45 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.6 mg/ml to about 5 mg/ml, from about 0.73 mg/ml to about 5 mg/ml, from about 0.8 mg/ml to about 5 mg/ml, from about 0.9 mg/ml to about 5 mg/ml, from about 1.0 mg/ml to about 5 mg/ml, from about 1.2 mg/ml to about 5 mg/ml, from about 1.45 mg/ml to about 5 mg/ml, from about 2 mg/ml to about 5 mg/ml, from about 2.5 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, about 1.2 mg/ml, about 1.45 mg/ml, etc. Alternatively, the cationic oil-in-water emulsion may comprise DDA at about 20 mg/ml, about 21 mg/ml, about 21.5 mg/ml, about 21.6 mg/ml, about 25 mg/ml. In an exemplary embodiment, the cationic oil-in-water emulsion comprises from about 0.73 mg/ml to about 1.45 mg/ml DDA, such as 1.45 mg/ml.

The RNA molecules of the invention can also be delivered to cells ex vivo, such as cells explanted from an individual patient (e.g., lymphocytes, bone marrow aspirates, tissue biopsy) or universal donor hematopoietic stem cells, followed by re-implantation of the cells into a patient, usually after selection for cells which have been transfected with the RNA molecule. The appropriate amount of cells to deliver to a patient will vary with patient conditions, and desired effect, which can be determined by a skilled artisan. See e.g., U.S. Pat. Nos. 6,054,288; 6,048,524; and 6,048,729. Preferably, the cells used are autologous, i.e., cells obtained from the patient being treated.

E. Adjuvants

In certain embodiments, the immunogenic compositions provided herein include or optionally include one or more immunoregulatory agents such as adjuvants. Exemplary adjuvants include, but are not limited to, a TH1 adjuvant and/or a TH2 adjuvant, further discussed below. In certain embodiments, the adjuvants used in the immunogenic compositions provide herein include, but are not limited to:

1. Mineral-Containing Compositions;
2. Oil Emulsions;
3. Saponin Formulations;
4. Virosomes and Virus-Like Particles;
5. Bacterial or Microbial Derivatives;
6. Bioadhesives and Mucoadhesives;
7. Liposomes;
8. Polyoxyethylene Ether and Polyoxyethylene Ester Formulations;
9. Polyphosphazene (PCPP);
10. Muramyl Peptides;
11. Imidazoquinolone Compounds;
12. Thiosemicarbazone Compounds;
13. Tryptanthrin Compounds;
14. Human Immunomodulators;
15. Lipopeptides;
16. Benzonaphthyridines;
17. Microparticles
18. Immunostimulatory polynucleotide (such as RNA or DNA; e.g., CpG-containing oligonucleotides)

1. Mineral Containing Compositions

Mineral containing compositions suitable for use as adjuvants include mineral salts, such as aluminum salts and calcium salts. The immunogenic composition may include mineral salts such as hydroxides (e.g., oxyhydroxides), phosphates (e.g., hydroxyphosphates, orthophosphates), sulfates, etc. (see, e.g., Vaccine Design: The Subunit and Adjuvant Approach (Powell, M. F. and Newman, M J. eds.) (New York: Plenum Press) 1995, Chapters 8 and 9), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (WO 00/23105).

Aluminum salts may be included in vaccines of the invention such that the dose of $Al^{3+}$ is between 0.2 and 1.0 mg per dose.

In certain embodiments, the aluminum based adjuvant is alum (aluminum potassium sulfate ($AlK(SO_4)_2$), or an alum derivative, such as that formed in-situ by mixing an antigen in phosphate buffer with alum, followed by titration and precipitation with a base such as ammonium hydroxide or sodium hydroxide.

Another aluminum-based adjuvant suitable for use in vaccine formulations is aluminum hydroxide adjuvant ($Al(OH)_3$) or crystalline aluminum oxyhydroxide (AlOOH), which is an excellent adsorbant, having a surface area of approximately 500 $m^2/g$. Alternatively, the aluminum based adjuvant can be aluminum phosphate adjuvant ($AlPO_4$) or aluminum hydroxyphosphate, which contains phosphate groups in place of some or all of the hydroxyl groups of aluminum hydroxide adjuvant. Preferred aluminum phosphate adjuvants provided herein are amorphous and soluble in acidic, basic and neutral media.

In certain embodiments, the adjuvant comprises both aluminum phosphate and aluminum hydroxide. In a more particular embodiment, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. In another embodiment, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the preferred aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (iep=4) adsorbs lysozyme, but not albumin at pH 7.4. Should albumin be the target, aluminum hydroxide adjuvant would be selected (iep=4). Alternatively, pretreatment of aluminum hydroxide with phosphate lowers its isoelectric point, making it a preferred adjuvant for more basic antigens.

2. Oil-Emulsions

Oil-emulsion compositions and formulations suitable for use as adjuvants (with or without other specific immunostimulating agents such as muramyl peptides or bacterial cell wall components) include squalene-water emulsions, such as MF59 (5% Squalene, 0.5% Tween 80, and 0.5% Span 85, formulated into submicron particles using a microfluidizer). See WO 90/14837. See also, Podda (2001) Vaccine 19: 2673-2680; Frey et al. (2003) Vaccine 21:4234-4237. MF59 is used as the adjuvant in the FLUAD™ influenza virus trivalent subunit vaccine.

Particularly preferred oil-emulsion adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80™ (polyoxyethylenesorbitan monooleate), and/or 0.25-1.0% Span 85™ (sorbitan trioleate), and, optionally, N-acetylmuramyl-L-alanyl-D-isogluatminyl-L-alanine-2-(1'-2'-dipalmitoyl-SM-glycero-3-huydroxyphosphophoryloxy)-ethylamine (MTP-PE), for example, the submicron oil-in-water emulsion known as "MF59" (WO 90/14837; U.S. Pat. Nos. 6,299,884; 6,451,325; and Ott et al., "MF59-Design and Evaluation of a Safe and Potent Adjuvant for Human Vaccines" in Vaccine Design: The Subunit and Adjuvant Approach (Powell, M. F. and Newman, M J. eds.) (New York: Plenum Press) 1995, pp. 277-296). MF59 contains 4-5% w/v Squalene (e.g. 4.3%), 0.25-0.5% w/v Tween 80™, and 0.5% w/v Span 85™ and optionally contains various amounts of MTP-PE, formulated into submicron particles using a microfluidizer such as Model 11 OY microfluidizer (Microfluidics, Newton, Mass.). For example, MTP-PE may be present in an amount of about 0-500 μg/dose, more preferably 0-250 mg/dose and most preferably, 0-100 μg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 μg MTP-PE per dose, and so on. MF69, another submicron oil-in-water emulsion for use herein, contains 4.3% w/v squalene, 0.25% w/v Tween 80™, and 0.75% w/v Span 85™ and optionally MTP-PE. Yet another submicron oil-in-water emulsion is MF75, also known as SAF, containing 10% squalene, 0.4% Tween 80™, 5% pluronic-blocked polymer L121, and thr-MDP, also microfluidized into a submicron emulsion. MF75-MTP denotes an MF75 formulation that includes MTP, such as from 100-400 μg MTP-PE per dose.

Submicron oil-in-water emulsions, methods of making the same and immunostimulating agents, such as muramyl peptides, for use in the compositions, are described in detail in WO 90/14837; U.S. Pat. Nos. 6,299,884; and 6,451,325.

Complete Freund's adjuvant (CFA) and incomplete Freund's adjuvant (IFA) may also be used as adjuvants in the invention.

3. Other Immunological Adjuvants

Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponins can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. Saponin adjuvant formulations include STIMULON® adjuvant (Antigenics, Inc., Lexington, Mass.).

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS 17, QS 18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO 96/33739).

Saponin formulations may include sterols, cholesterols and lipid formulations. Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP 0 109 942, WO 96/11711 and WO 96/33739. Optionally, the ISCOMS may be devoid of (an) additional detergent(s). See WO 00/07621.

A review of the development of saponin based adjuvants can be found in Barr et al. (1998) Adv. Drug Del. Rev. 32:247-271. See also Sjolander et al. (1998) Adv. Drug Del. Rev. 32:321-338.

Virosomes and Virus Like Particles (VLPs) generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein pi). VLPs are discussed further in WO 03/024480; WO 03/024481; Niikura et al. (2002) Virology 293:273-280; Lenz et al. (2001) J. IMMUNOL. 166(9):5346-5355' Pinto et al. (2003) J. Infect. Dis. 188:327-338; and Gerber et al. (2001) J. Virol. 75(10):4752-4760. Virosomes are discussed further in, for example, Gluck et al. (2002) Vaccine 20:B10-B16. Immunopotentiating reconstituted influenza virosomes (IRIV) are used as the subunit antigen delivery system in the intranasal trivalent INFLEXAL™ product (Mischler and Metcalfe (2002) Vaccine 20 Suppl 5:B17-B23) and the INFLUVAC PLUS™ product.

Bacterial or microbial derivatives suitable for use as adjuvants include, but are not limited to:

(1) Non-toxic derivatives of enterobacterial lipopolysaccharide (LPS): Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives, e.g., RC-529. See Johnson et al. (1999) Bioorg. Med. Chem. Lett. 9:2273-2278.

(2) Lipid A Derivatives: Lipid A derivatives include derivatives of lipid A from *Escherichia coli* such as OM-174. OM-174 is described for example in Meraldi et al. (2003) Vaccine 21:2485-2491; and Pajak et al. (2003) Vaccine 21:836-842. Another exemplary adjuvant is the synthetic phospholipid dimer, E6020 (Eisai Co. Ltd., Tokyo, Japan), which mimics the physicochemical and biological properties of many of the natural lipid A's derived from Gram-negative bacteria.

(3) Immunostimulatory oligonucleotides: Immunostimulatory oligonucleotides or polymeric molecules suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory. The CpG's can include nucleotide modifications/analogs such as phosphorothioate modifications and can be double-stranded or single-stranded. Optionally, the guanosine may be replaced with an analog such as 2'-deoxy-7-deazaguanosine. See Kandimalla et al. (2003) Nucl. Acids Res. 31(9): 2393-2400; WO 02/26757; and WO 99/62923 for examples of possible analog substitutions. The adjuvant effect of CpG oligonucleotides is further discussed in Krieg (2003) Nat. Med. 9(7):831-835; McCluskie et al. (2002) FEMS Immunol. Med. Microbiol. 32: 179-185; WO 98/40100; U.S. Pat. Nos. 6,207,646; 6,239,116; and 6,429,199.

The CpG sequence may be directed to TLR9, such as the motif GTCGTT or TTCGTT. See Kandimalla et al. (2003) Biochem. Soc. Trans. 31 (part 3):654-658. The CpG sequence may be specific for inducing a ThI immune response, such as a CpG-A ODN, or it may be more specific for inducing a B cell response, such a CpG-B ODN. CpG-A and CpG-B ODNs are discussed in Blackwell et al. (2003) J. Immunol. 170(8):4061-4068; Krieg (2002) TRENDS Immunol. 23(2): 64-65; and WO 01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla et al. (2003) BBRC 306:948-953; Kandimalla et al. (2003) Biochem. Soc. Trans. 3 1(part 3):664-658' Bhagat et al. (2003) BBRC 300:853-861; and WO03/035836.

Immunostimulatory oligonucleotides and polymeric molecules also include alternative polymer backbone structures such as, but not limited to, polyvinyl backbones (Pitha et al. (1970) Biochem. Biophys. Acta 204(1):39-48; Pitha et al. (1970) Biopolymers 9(8):965-977), and morpholino backbones (U.S. Pat. Nos. 5,142,047; 5,185,444). A variety of other charged and uncharged polynucleotide analogs are known in the art. Numerous backbone modifications are known in the art, including, but not limited to, uncharged linkages (e.g., methyl phosphonates, phosphotriesters, phosphoamidates, and carbamates) and charged linkages (e.g., phosphorothioates and phosphorodithioates).

Adjuvant IC31, Intercell AG, Vienna, Austria, is a synthetic formulation that contains an antimicrobial peptide, KLK, and an immunostimulatory oligonucleotide, ODNIa. The two component solution may be simply mixed with antigens (e.g., particles in accordance with the invention with an associated antigen), with no conjugation required.

ADP-ribosylating toxins and detoxified derivatives thereof: Bacterial ADP-ribosylating toxins and detoxified derivatives thereof may be used as adjuvants in the invention. Preferably, the protein is derived from *E. coli* (i.e., *E. coli* heat labile enterotoxin "LT"), cholera ("CT"), or pertussis ("PT"). The use of detoxified ADP-ribosylating toxins as mucosal adjuvants is described in WO 95/17211 and as parenteral adjuvants in WO 98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references: Beignon et al. (2002) Infect. Immun. 70(6):3012-3019; Pizza et al. (2001) Vaccine 19:2534-2541; Pizza et al. (2000) J. Med. Microbiol. 290(4-5):455-461; Scharton-Kersten et al. (2000) Infect. Immun 68(9):5306-5313' Ryan et al. (1999) Infect. Immun. 67(12):6270-6280; Partidos et al. (1999) Immunol. Lett. 67(3):209-216; Peppoloni et al. (2003) Vaccines 2(2): 285-293; and Pine et al. (2002) J. Control Release 85(1-3): 263-270. Numerical reference for amino acid substitutions is preferably based on the alignments of the A and B subunits of ADP-ribosylating toxins set forth in Domenighini et al. (1995) MoI. Microbiol. 15(6): 1165-1167.

Bioadhesives and mucoadhesives may also be used as adjuvants. Suitable bioadhesives include esterified hyaluronic acid microspheres (Singh et al. (2001) J. Cont. Release 70:267-276) or mucoadhesives such as cross-linked derivatives of polyacrylic acid, polyvinyl alcohol, polyvinyl pyrollidone, polysaccharides and carboxymethylcellulose.

Chitosan and derivatives thereof may also be used as adjuvants in the invention (see WO 99/27960).

Examples of liposome formulations suitable for use as adjuvants are described in U.S. Pat. Nos. 6,090,406; 5,916,588; and EP Patent Publication No. EP 0 626 169.

Adjuvants suitable for use in the invention include polyoxyethylene ethers and polyoxyethylene esters (see, e.g., WO 99/52549). Such formulations further include polyoxyethylene sorbitan ester surfactants in combination with an octoxynol (WO 01/21207) as well as polyoxyethylene alkyl ethers or ester surfactants in combination with at least one additional non-ionic surfactant such as an octoxynol (WO 01/21152). Preferred polyoxyethylene ethers are selected from the following group: polyoxyethylene-9-lauryl ether (laureth 9), polyoxyethylene-9-steoryl ether, polyoxythey-lene-8-steoryl ether, polyoxyethylene-4-lauryl ether, polyoxyethylene-35-lauryl ether, and polyoxyethylene-23-lauryl ether.

PCPP formulations suitable for use as adjuvants are described, for example, in Andrianov et al. (1998) Biomaterials 19(1-3): 109-115; and Payne et al. (1998) Adv. Drug Del. Rev. 31(3): 185-196.

Examples of muramyl peptides suitable for use as adjuvants include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxy-phosphoryloxy)-ethylamine MTP-PE).

Examples of imidazoquinoline compounds suitable for use as adjuvants include Imiquimod and its analogues, which are described further in Stanley (2002) Clin. Exp. Dermatol. 27(7):571-577; Jones (2003) Curr. Opin. Investig. Drugs 4(2):214-218; and U.S. Pat. Nos. 4,689,338; 5,389,640; 5,268,376; 4,929,624; 5,266,575; 5,352,784; 5,494,916; 5,482,936; 5,346,905; 5,395,937; 5,238,944; and 5,525,612.

Examples of thiosemicarbazone compounds suitable for use as adjuvants, as well as methods of formulating, manufacturing, and screening for such compounds, include those described in WO 04/60308. The thiosemicarbazones are particularly effective in the stimulation of human peripheral blood mononuclear cells for the production of cytokines, such as TNF-α.

Examples of tryptanthrin compounds suitable for use as adjuvants, as well as methods of formulating, manufacturing, and screening for such compounds, include those described in WO 04/64759. The tryptanthrin compounds are particularly effective in the stimulation of human peripheral blood mononuclear cells for the production of cytokines, such as TNF-α. examples of benzonaphthyridine compounds suitable for use as adjuvants include:

Examples of benzonaphthyridine compounds suitable for use as adjuvants, as well as methods of formulating and manufacturing, include those described in WO 2009/111337.

Lipopeptides suitable for use as adjuvants are described above. Other exemplary lipopeptides include, e.g., LP 40, which is an agonist of TLR2. See, e.g., Akdis, et al, Eur. J. Immunology, 33: 2717-26 (2003). Murein lipopeptides are lipopeptides derived from *E. coli*. See, Hantke, et al., Eur. J. Biochem., 34: 284-296 (1973). Murein lipopeptides comprise a peptide linked to N-acetyl muramic acid, and are thus related to Muramyl peptides, which are described in Baschang, et al., Tetrahedron, 45(20): 6331-6360 (1989).

The human immunomodulators suitable for use as adjuvants include, but are not limited to, cytokines, such as, by way of example only, interleukins (IL-1, IL-2, IL-4, IL-5, IL-6, IL-7, IL-12), interferons (such as, by way of example only, interferon-γ), macrophage colony stimulating factor, and tumor necrosis factor.

Microparticles suitable for use as adjuvants include, but are not limited to, microparticles formed from materials that are biodegradable and non-toxic (e.g. a poly(.alpha.-hydroxy acid), a polyhydroxybutyric acid, a polyorthoester, a polyanhydride, a polycaprolactone, etc.), with poly(lactide-co-glycolide). In certain embodiments, such microparticles are treated to have a negatively-charged surface (e.g. with SDS) or a positively-charged surface (e.g. with a cationic detergent, such as CTAB). The microparticles suitable for use as adjuvants have a particle diameter of about 100 nm to about 150 μm in diameter. In certain embodiments, the particle diameter is about 200 nm to about 30 μm, and in other embodiments the particle diameter is about 500 nm to 10 μm.

4. Kits

The invention also provides kits, wherein the RNA molecule encoding the first polypeptide antigen and the second polypeptide antigen are in separate containers. For example, the kit can contain a first container comprising a composition comprising the RNA molecule encoding the first polypeptide antigen, and a second container comprising a composition comprising the second polypeptide antigen.

The kits described may be used for co-delivery of the RNA component and the polypeptide component of the immunogenic compositions described herein (e.g., the RNA component and the polypeptide component may be mixed prior to administration for simultaneous delivery).

The composition that comprises the polypeptide or the RNA molecule can be in liquid form or can be in solid form (e.g., lyophilized). Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

The kit can further comprise a third container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device. The kit may further include a fourth container comprising an adjuvant (such as an aluminum containing adjuvant or MF59).

The kit can also comprise a package insert containing written instructions for methods of inducing immunity or for treating infections. The package insert can be an unapproved draft package insert or can be a package insert approved by the Food and Drug Administration (FDA) or other regulatory body.

The invention also provides a delivery device pre-filled with the immunogenic compositions, the priming componsitions, or the boosting compositions described above.

5. Immunogenic Compositions

In one aspect, the invention relates to immunogenic compositions comprising: (i) a first polypeptide antigen, and (ii) a self-replicating RNA molecule that encodes a second polypeptide antigen; wherein said first and second polypeptide antigens are from different pathogens.

The immunogenic compositions typically include a pharmaceutically acceptable carrier and/or a suitable delivery system as described herein, such as liposomes, nanoemulsions, PLG micro- and nanoparticles, lipoplexes, chitosan micro- and nanoparticles and other polyplexes. If desired other pharmaceutically acceptable components can be included, such as excipients and adjuvants. These compositions can be used as anti-viral vaccines.

Pharmaceutically acceptable carriers are determined in part by the particular composition being administered, as well as by the particular method used to administer the composition. Accordingly, there is a wide variety of suitable formulations of immunogenic compositions of the present invention. A variety of aqueous carriers can be used. Suitable pharmaceutically acceptable carriers for use in the immunogenic compositions include plain water (e.g. w.f.i.) or a buffer e.g. a phosphate buffer, a Tris buffer, a borate buffer, a succinate buffer, a histidine buffer, or a citrate buffer. Buffer salts will typically be included in the 5-20 mM range.

The immunogenic compositions are preferably sterile, and may be sterilized by conventional sterilization techniques.

The compositions may contain pharmaceutically acceptable auxiliary substances as required to approximate physiological conditions such as pH adjusting and buffering agents, and tonicity adjusting agents and the like, for example, sodium acetate, sodium chloride, potassium chloride, calcium chloride, sodium lactate and the like.

Preferably, the immunogenic compositions of the invention may have a pH between 5.0 and 9.5, e.g. between 6.0 and 8.0.

Immunogenic compositions of the invention may include sodium salts (e.g. sodium chloride) to give tonicity. A concentration of 10±2 mg/ml NaCl is typical e.g. about 9 mg/ml.

Immunogenic compositions of the invention may have an osmolality of between 200 mOsm/kg and 400 mOsm/kg, e.g. between 240-360 mOsm/kg, or between 290-310 mOsm/kg.

Immunogenic compositions of the invention may include one or more preservatives, such as thiomersal or 2-phenoxyethanol. Mercury-free compositions are preferred, and preservative-free vaccines can be prepared.

Immunogenic compositions of the invention are preferably non-pyrogenic e.g. containing <1 EU (endotoxin unit, a standard measure) per dose, and preferably <0.1 EU per dose. Immunogenic compositions of the invention are preferably gluten free.

The concentrations of the polypeptide molecule and the RNA molecule in the immunogenic compositions can vary, and will be selected based on fluid volumes, viscosities, body weight and other considerations in accordance with the particular mode of administration selected and the intended recipient's needs. However, the immunogenic compositions are formulated to provide an effective amount of RNA+ polypeptide, such as an amount (either in a single dose or as part of a series) that is effective for treatment or prevention. This amount varies depending upon the health and physical condition of the individual to be treated, age, the taxonomic group of individual to be treated (e.g. non-human primate, human primate, etc.), the capacity of the individual's immune system to react to the antigen, the condition to be treated, and other relevant factors. It is expected that the amount will fall in a relatively broad range that can be determined through routine trials. The RNA content of compositions will generally be expressed in terms of the amount of RNA per dose. A preferred dose has ≤200 µg, ≤100 µg, ≤50 µg, or ≤10 µg RNA, and expression can be seen at much lower levels e.g. ≤1 µg/dose, ≤100 ng/dose, ≤10 ng/dose, ≤1 ng/dose, etc. The amount of polypeptide in each dose will generally comprise from about 0.1 to about 100 µg of polypeptide, with from about 5 to about 50 µg being preferred and from about 5 to about 25 µg/dose being alternatively preferred.

The amount of adjuvant, if any, will be an amount that will induce an immunomodulating response without significant adverse side effect. An optional amount for a particular vaccine can be ascertained by standard studies involving observation of a vaccine's antibody titers and their virus neutralization capabilities. The amount of adjuvant will be from about 1 to about 100 µg/dose, with from about 5 to about 50 µg/dose being preferred, and from about 20 to about 50 µg/dose being alternatively preferred.

Formulations suitable for parenteral administration, such as, for example, by intraarticular (in the joints), intravenous or intraperitoneal injection, and preferably by intramuscular, intradermal or subcutaneous injection, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampoules and vials. Injection solutions and suspensions can be prepared from sterile powders, granules, and tablets. Cells transduced by the RNA molecules can also be administered intravenously or parenterally.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

It is recognized that polypeptide and RNA molecules, when administered orally, must be protected from digestion. Protection of polypeptide and RNA molecules can typically be accomplished either by complexing the RNA molecule or the polypeptide molecule with a composition to render the RNA/polypeptide resistant to acidic and enzymatic hydrolysis, or by packaging the RNA molecule or the polypeptide molecule in an appropriately resistant carrier such as a liposome. Means of protecting nucleic acids (such as RNA molecules) and polypeptides from digestion are well known in the art.

The immunogenic compositions can be encapsulated, e.g., in liposomes, or in a formulation that provides for slow release of the active ingredient. For example, the RNA molecule may be formulated as lioposomes, then administered as a priming composition. Alternatively, liposome-formulated RNA may be mixed with the polypeptide molecule to produce the RNA+polypeptide immunogenic composition of the invention. Alternatively, the RNA molecule and the polypeptide molecule can be co-encapsulated in liposomes.

The compositions described herein (immunogenic compositions comprising an RNA and a polypeptide), alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Suitable suppository formulations may contain the RNA, the polypeptide, or the polypeptide and RNA combination as described herein, and a suppository base. Suitable suppository bases include natural or synthetic triglycerides or paraffin hydrocarbons. It is also possible to use gelatin rectal capsules filled with the polypeptide and RNA molecules as described herein, and a suitable base, for example, liquid triglycerides, polyethylene glycols, and paraffin hydrocarbons.

6. Methods of Generating or Enhancing Immune Responses

In another aspect, the invention provides a method for inducing, generating or enhancing an immune response in a subject in need thereof, such as a vertebrate, preferably a mammal, comprising administering an effective amount of an immunogenic composition comprising: (i) a self-replicating RNA molecule that encodes a first polypeptide antigen, and (ii) a second polypeptide antigen; wherein said first and second polypeptide antigens are from different pathogens. The immune response is preferably protective and preferably involves antibodies and/or cell-mediated immunity.

In another aspect, the immunogenic compositions disclosed herein may be used in the manufacture of a medicament for inducing, generating, or enhancing an immune response in a subject in need thereof, such as a vertebrate, preferably a mammal.

In another aspect, the invention provides a method for treating or preventing an infectious disease in a subject (such as a vertebrate, preferably a mammal) in need thereof, comprising administering an effective amount of an immunogenic composition comprising: (i) a self-replicating RNA molecule that encodes a first polypeptide antigen, and (ii) a second polypeptide antigen; wherein said first and second polypeptide antigens are from different pathogens.

In another aspect, the compositions disclosed herein may be used in the manufacture of a medicament for treating or preventing an infectious disease in a subject in need thereof, such as a vertebrate, preferably a mammal.

In another aspect, the invention provides a method for vaccinating a subject, such as a vertebrate, preferably a mammal, or immunizing a subject against a pathogen (e.g., a bacterial pathogen, a viral pathogen, a fungal pathogen, a protozoan pathogen, or a multi-cellular parasitic pathogen), comprising administering to a subject in need thereof an effective amount of an immunogenic composition comprising: (i) a self-replicating RNA molecule that encodes a first polypeptide antigen, and (ii) a second polypeptide antigen; wherein said first and second polypeptide antigens are from different pathogens.

In another aspect, the compositions disclosed herein may be used in the manufacture of a medicament for vaccinating a subject in need thereof, such as a vertebrate, preferably a mammal.

Suitable animal subjects include, for example, fish, birds, cattle, pigs, horses, deer, sheep, goats, bison, rabbits, cats, dogs, chickens, ducks, turkeys, and the like. The mammal is preferably a human. Where the vaccine is for prophylactic use, the human is preferably a child (e.g., a toddler or infant), a teenager, or an adult; where the vaccine is for therapeutic use, the human is preferably a teenager or an adult. A vaccine intended for children may also be administered to adults, e.g., to assess safety, dosage, immunogenicity, etc.

One way of checking efficacy of therapeutic treatment involves monitoring pathogen infection after administration of the compositions or vaccines disclosed herein. One way of checking efficacy of prophylactic treatment involves monitoring immune responses, systemically (such as monitoring the level of IgG1 and IgG2a production) and/or mucosally (such as monitoring the level of IgA production), against the antigen. Typically, antigen-specific serum antibody responses are determined post-immunization but pre-challenge whereas antigen-specific mucosal antibody responses are determined post-immunization and post-challenge.

Another way of assessing the immunogenicity of the compositions or vaccines disclosed herein where the nucleic acid molecule (e.g., the RNA) encodes a protein antigen is to express the protein antigen recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within protein antigens.

The efficacy of the compositions can also be determined in vivo by challenging appropriate animal models of the pathogen of interest infection.

When the RNA molecule and the polypeptide molecule are co-administered, it may still be desirable to package the polypeptide molecule and RNA molecule separately. The two components may be combined, e.g., within about 72 hours, about 48 hours, about 24 hours, about 12 hours, about 10 hours, about 9 hours, about 8 hours, about 7 hours, about 6 hours, about 5 hours, about 4 hours, about 3 hours, about 2 hours, about 1 hour, about 45 minutes, about 30 minutes, about 15 minutes, about 10 minutes, or about 5 minutes prior to administration. For example, the polypeptide molecule and RNA molecule can be combined at a patient's bedside.

Dosage can be by a single dose schedule or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, etc.). The immunogenic compositions disclosed herein may be used as the prime and/or boost, regardless of whether the immunogenic composition administered as a prime or boost comprised a single pathogen vaccine.

The compositions disclosed herein that include one or more antigens or are used in conjunction with one or more antigens may be used to treat both children and adults. Thus a human subject may be less than 1 year old, 1-5 years old, 5-15 years old, 15-55 years old, or at least 55 years old. Preferred subjects for receiving the compositions are the elderly (e.g., >50 years old, >60 years old, and preferably >65 years), the young (e.g., <5 years old), hospitalized patients, healthcare workers, armed service and military personnel, pregnant women, the chronically ill, or immunodeficient patients. The compositions are not suitable solely for these groups, however, and may be used more generally in a population.

Preferred routes of administration include, but are not limited to, intramuscular, intraperitoneal, intradermal, subcutaneous, intravenous, intraarterial, and intraoccular injection. Oral and transdermal administration, as well as administration by inhalation or suppository is also contemplated. Particularly preferred routes of administration include intramuscular, intradermal and subcutaneous injection. According to some embodiments of the present invention, the composition is administered to a host animal using a needleless injection device, which are well-known and widely available.

It is sometimes advantageous to employ a vaccine that targets a particular target cell type (e.g., an antigen presenting cell or an antigen processing cell).

Catheters or like devices may be used to deliver the composition of the invention, as polypeptide+naked RNA, polypeptide+RNA formulated with a delivery system (e.g., RNA encapsulated in liposomes), RNA only, or polypeptide only into a target organ or tissue. Suitable catheters are disclosed in, e.g., U.S. Pat. Nos. 4,186,745; 5,397,307; 5,547,472; 5,674,192; and 6,129,705, all of which are incorporated herein by reference. The RNA molecules of the invention can also be introduced directly into a tissue, such as muscle. See, e.g., U.S. Pat. No. 5,580,859. Other methods such as "biolistic" or particle-mediated transformation (see, e.g., Sanford et al., U.S. Pat. Nos. 4,945,050; 5,036,006) are also suitable for introduction of RNA into cells of a mammal. These methods are useful not only for in vivo introduction of RNA into a mammal, but also for ex vivo modification of cells for reintroduction into a mammal.

The present invention includes the use of suitable delivery systems, such as liposomes, polymer microparticles or submicron emulsion microparticles with encapsulated or adsorbed RNA, or RNA+polypeptide, to deliver the RNA, or RNA+polypeptide, to elicit an immune response. The invention includes liposomes, microparticles, submicron emulsions, or combinations thereof, with adsorbed and/or encapsulated RNA, or RNA+polypeptide.

The compositions disclosed herein that include one or more antigens, or are used in conjunction with one or more antigens, may be administered to patients at substantially the same time as (e.g., during the same medical consultation or visit to a healthcare professional or vaccination centre) other vaccines, e.g., at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A C W135 Y vaccine), a respiratory syncytial virus vaccine, etc.

7. Definitions

The term "about", as used herein, refers to +/−10% of a value.

An "antigen" refers to a molecule containing one or more epitopes (either linear, conformational or both).

As used herein, a "polypeptide antigen" refers to a polypeptide comprising one or more epitopes (either linear, conformational or both), that elicits an immunological response. Polypeptide antigens include, for example, a naturally-occurring protein, a mutational variant of a naturally-occurring protein (e.g., a protein that has amino acid substitution(s), addition(s), or deletion(s)), a truncated form of a naturally-occurring protein (e.g., an intracellular domain or extracellular domain of a membrane-anchored protein), as well as a fusion protein (a protein that is derived from at least two different naturally occurring proteins or polypeptide chains). In addition, polypeptide antigens also encompass polypeptides that comprise one or more amino acid stereoisomers, derivatives, or analogues. For example, amino acid derivatives include, e.g., chemical modifications of amino acids such as alkylation, acylation, carbamylation, iodination, etc. Amino acid analogues include, e.g., compounds that have the same basic chemical structure as a naturally occurring amino acid, such as homoserine, norleucine, methionine sulfoxide, methionine methyl sulfonium. Polypeptide antigens also encompass polypeptides that are modified post-translationally (such as acetylated, phosphorylated, or glycosylated polypeptides). Therefore, an epitope of a polypeptide antigen is not limited to a peptide. For example, an epitope of a glycosylated polypeptide may be a saccharide group that is attached to the polypeptide chain.

The term "fusion polypeptide" refers to a single polypeptide in which the amino acid sequence is derived from at least two different naturally occurring proteins or polypeptide chains.

An "epitope" is a portion of an antigen that is recognized by the immune system (e.g., by an antibody, an immunoglobulin receptor, a B cell receptor, or a T cell receptor). An epitope can be linear or conformational. Commonly, an epitope is a polypeptide or polysaccharide in a naturally occurring antigen. In artificial antigens it can be a low molecular weight substance such as an arsanilic acid derivative. Normally, a B-cell epitope will include at least about 5 amino acids but can be as small as 3-4 amino acids. A T-cell epitope, such as a CTL epitope, will typically include at least about 7-9 amino acids, and a helper T-cell epitope will typically include at least about 12-20 amino acids.

When an individual is immunized with a polypeptide antigen having multiple epitopes, in many instances the majority of responding T lymphocytes will be specific for one or a few linear epitopes from that antigen and/or a majority of the responding B lymphocytes will be specific for one or a few linear or conformational epitopes from that antigen. Such epitopes are typically referred to as "immunodominant epitopes." In an antigen having several immunodominant epitopes, a single epitope may be most dominant, and is typically referred to as the "primary" immunodominant epitope. The remaining immunodominant epitopes are typically referred to as "secondary" immunodominant epitope(s).

As used herein, the terms "minor structural protein" or "minor structural polypeptide" or "minor capsid protein" or "minor capsid polypeptide" or "VP 1" in reference to a parvovirus refer to a polypeptide comprising a sequence homologous or identical to the ORF2-encoded polypeptide of a parvovirus, and includes sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99, 100% sequence identity thereto.

As used herein, the terms "major structural protein" or "major structural polypeptide" or "major capsid protein" or "major capsid polypeptide" or "VP2" in reference to a Parvovirus refer to a polypeptide comprising a sequence homologous or identical to the ORF3-encoded polypeptide of a Parvovirus, and include sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99, 100% sequence identity thereto.

The term "naked" as used herein refers to nucleic acids that are substantially free of other macromolecules, such as lipids, polymers, and proteins. A "naked" nucleic acid, such as a self-replicating RNA, is not formulated with other macromolecules to improve cellular uptake. Accordingly, a naked nucleic acid is not encapsulated in, absorbed on, or bound to a liposome, a microparticle or nanoparticle, a cationic emulsion, and the like.

As used herein, "nucleotide analog" or "modified nucleotide" refers to a nucleotide that contains one or more chemical modifications (e.g., substitutions) in or on the nitrogenous base of the nucleoside (e.g., cytosine (C), (thymine (T) or uracil (U)), adenine (A) or guanine (G)). A nucleotide analog can contain further chemical modifications in or on the sugar moiety of the nucleoside (e.g., ribose, deoxyribose, modified ribose, modified deoxyribose, six-membered sugar analog, or open-chain sugar analog), or the phosphate.

As used herein, the term "parvovirus" refers to all parvoviruses associated with mammalian species (e.g., human, canine, chicken, feline, murine, porcine, raccoon, mink, kilham rat, lapine) and broadly to all genus of the Parvoviridae family (i.e., Parvovirus (e.g., canine parvovirus), Dependovirus (e.g., adeno-associated virus), Erythrovirus (e.g., parvovirus B19) and Bocavirus). The term parvovirus also includes isolates not characterized at the time of filing.

As used herein, the term "parvovirus antigen" refers to a molecule derived from a parvovirus, including, without limitation, any of the various isolates of parvovirus. The molecule need not be physically derived from the particular isolate in question, but may be synthetically or recombinantly produced.

The term "pathogen" refers to a virus, eukaryote, prokaryote or archaea that is capable of proliferation, and causes a disease or illness in a host organism, such as a vertebrate (e.g., a mammal). A pathogen can be a viral, bacterial, protozoan, or fungal species, as well as a multicellular parasitic species.

The terms "treat," "treating" or "treatment", as used herein, include alleviating, abating or ameliorating disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

The term "viral replicon particle" or "VRP" refers to recombinant infectious virions that cannot generate infectious progeny because of deletion of structural gene(s).

The term "virus-like particle" or "VLP" refers to a structure formed by viral coat proteins (e.g., a capsid) and optionally an evelope, but having no genetic material. A VLP resembles a viral particle.

EXEMPLIFICATION

The invention now being generally described, it will be more readily understood by reference to the following example, which is included merely for purposes of illustration of certain aspects and embodiments of the present invention, and is not intended to limit the invention.

Example 1

BALB/c mice, 60 animals total, were divided into 6 groups (10 animals per group). Ten BALB/c mice, per group, were bled before immunization to collect pre-immune sera. Mice were given bilateral intramuscular vaccinations (50 μL per leg) on days 0, 21 and 42 with the formulation indicated in Table 1. The LNP (RV01(15) had the following composition: 40% DlinDMA, 10% DSPC, 48% Chol, 2% PEG DMG 2000 and an N:P ratio of 8:1. Serum was collected for immunological analysis on days 21 (3 wp1), 42 (3wp2) and 63 (3wp3).

TABLE 1

Vaccine groups

| Group # | Parvovirus Antigen | CMV Antigen | Adjuvant |
|---|---|---|---|
| 1 | Mutant VP1/VP2 VLP, 5 μg | None | None |
| 2 | Mutant VP1/VP2 VLP, 5 μg | None | MF59 |
| 3 | None | gH full-length/ gL VRP, $1 \times 10^6$ IU | None |
| 4 | None | gH full-length/ gL RNA, 1 μg | LNP (RV01 (15)) |
| 5 | Mutant VP1/VP2 VLP, 5 μg | gH full-length/ gL VRP, $1 \times 10^6$ IU | None |
| 6 | Mutant VP1/VP2 VLP, 5 μg | gH full-length/ gL RNA, 1 μg | LNP (RV01 (15)) |

Three weeks after the immunization the mice were bled again, and sera collected for testing. The following day mice received a second immunization with the same vaccine previously administered to them. Three weeks after the second immunization, the mice were bled and sera collected for testing. A third immunization was administered to the mice the following day. Three weeks after the third immunization, the mice were bled and sera collected for testing.

A Parvovirus specific response was measured by ELISA for serum IgG titers. Wild-type Parvovirus B19 VP1/VP2 was used to coat the microtiter plates. Sera collected from the bleeds (pre-immune, 3 weeks post 1st immunization, and 3 weeks post 2nd immunization) were pooled for each vaccine group (n=10) and measured for IgG titer.

TABLE 2

CMV serum neutralization titers of BALB/c mice, 10 animals per group, after intramuscular vaccinations on days 0, 21 and 42. Serum was collected for analysis on days 42 (3wp2) and 63 (3wp3) and incubated with TB40 virus on ARPE-19 cells without complement The neutralization titer is defined as the reciprocal of the serum dilution producing a 50% reduction in number of positive virus foci per well, relative to controls.

| Vaccine Group | 3wp2 | 3wp3 |
|---|---|---|
| Parvo VLP, 5 mg | <100 | <100 |
| Parvo VLP, 5 mg/MF59 | <100 | <100 |
| CMV VRP, 1E6 | 7,943 | 14,430 |
| CMV RNA, 1 mg/RV01 (35) | 5,497 | 18,328 |
| Parvo VLP + CMV VRP | 12,800 | 17,911 |
| Parvo VLP + CMV RNA/RV01 | 4,569 | 22,688 |

Higher Parvovirus IgG titers were observed in sera from mice who received a vaccine where CMV antigen (either CMV VRP or CMV RNA) was added to Parvovirus VLP vaccine. Three weeks after the first immunization, the IgG titer increased 6-fold (40 v. 250) for Parvovirus+CMV VRP vaccine, as compared to Parvovirus alone vaccine. The difference was even greater (50-fold increase (40 v. 2,000)) three weeks after the first immunization, when the IgG titer of Parvovirus+CMV RNA vaccine was compared to Parvovirus alone vaccine.

Three weeks after the second immunization, the IgG titer increased 2-fold (4,000 v. 9,200) for Parvovirus+CMV VRP vaccine, as compared to Parvovirus alone vaccine. As seen with the first observation, the difference was even greater (35-fold increase (4,000 v. 138,600)) three weeks after the second immunization, when the IgG titer of Parvovirus+CMV RNA vaccine was compared to Parvovirus alone vaccine.

TABLE 3

Parvo-specific serum IgG titers of BALB/c mice, 10 animals per group, 21 (3wp1), 42 (3wp2) and 63 (3wp3) days after intramuscular vaccination on days 0, 21 and 42. Data are represented as pooled titers of 10 individual mice per group. If an individual animal had a titer of <25 (limit of detection), it was assigned a titer of 25.

| Serum Sample | Vaccine group | 3wp1 | 3wp2 | 3wk3 |
|---|---|---|---|---|
| Pre-immune | | <25 | | |
| 1 | Parvo VLP, 5 mg | 41 | 3972 | 404 |
| 2 | Parvo VLP, 5 mg/MF59 | 7868 | 365181 | 53603 |
| 3 | CMV VRP, 1E6 | <25 | <25 | <25 |
| 4 | CMV RNA, 1 mg/RV01 (35) | <25 | <25 | <25 |
| 5 | Parvo VLP + CMV VRP | 246 | 9202 | 1505 |
| 6 | Parvo VLP + CMV RNA/ RV01 (35) | 2000 | 138585 | 16649 |

The pooled sera were tested for a CMV specific response by measuring serum neutralizing antibody titers. No major change was observed in CMV neutralization titers when Parvovirus VLP was added to either CMV VRP or CMV RNA vaccines.

The highest titers were observed with Parvovirus VLP and MF59 adjuvant. However, the Parvovirus VLP/MF59 composition titer was only ~3-fold greater than the titer seen when Parvovirus VLP was combined with CMV RNA.

TABLE 4

Parvo serum neutralization titers of BALB/c mice, 10 animals per group, after intramuscular vaccinations on days 0, 21 and 42. Serum was collected, pooled for analysis on days 42 (3wp2) and 63 (3wp3) and tested using an erythroid progenitor cell based qRT-PCR neutralization assay.

| | | % netralization Titers | | | | |
|---|---|---|---|---|---|---|
| | Dilution | 1:500 | 1:2500 | 1:12500 | 1:62500 | 1:312500 |
| 3wp2 | Parvo VLP/ MF59 | 85.96 | 75.57 | 44.66 | 28.03 | −46.09 |
| 3wp2 | Parvo VLP + CMV RNA/ RV01 (35) | 26.90 | 4.10 | 8.27 | 15.78 | −14.01 |
| 3wp3 | Parvo VLP | 56.86 | 40.23 | 24.44 | 3.29 | −5.88 |
| 3wp3 | Parvo VLP/ MF59 | 94.06 | 87.94 | 70.02 | 37.37 | −19.09 |
| 3wp3 | Parvo VLP + CMV VRP | 73.38 | 44.18 | 19.69 | 9.57 | 15.38 |
| 3wp3 | Parvo VLP + CMV RNA/ RV01 (35) | 83.93 | 73.10 | 40.08 | 32.36 | 25.06 |
| 5wp3 | 5 ug Parvo VLP | 89.74 | 80.49 | 58.67 | 57.08 | 25.13 |
| | PI | −229.18 | −191.24 | −94.47 | −112.55 | −197.63 |

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

```
SEQUENCES
CMV gB FL:
                                                             SEQ ID NO: 1
1-atggaaagccggatctggtgcctggtcgtgtgcgtgaacctgtgcatcgtgtgcctgggagc

cgccgtgagcagcagcagcaccagaggcaccagcgccacacacagccaccacagcagccaca

ccacctctgccgcccacagcagatccggcagcgtgtcccagagagtgaccagcagccagacc

gtgtcccacggcgtgaacgagacaatctacaacaccaccctgaagtacggcgacgtcgtggg

cgtgaataccaccaagtacccctacagagtgtgcagcatggcccagggcaccgacctgatca

gattcgagcggaacatcgtgtgcaccagcatgaagcccatcaacgaggacctggacgagggc

atcatggtggtgtacaagagaaacatcgtggcccacaccttcaaagtgcgggtgtaccagaa

ggtgctgaccttccggcggagctacgcctacatccacaccacatacctgctgggcagcaaca

ccgagtacgtggcccctcccatgtgggagatccaccacatcaacagccacagccagtgctac

agcagctacagccgcgtgatcgccggcacagtgttcgtggcctaccaccgggacagctacga

gaacaagaccatgcagctgatgcccgacgactacagcaacacccacagcaccagatacgtga

ccgtgaaggaccagtggcacagcagaggcagcacctggctgtaccgggagacatgcaacctg

aactgcatggtcaccatcaccaccgccagaagcaagtacccttaccacttcttcgccacctc
```

-continued caccggcgacgtggtggacatcagccccttctacaacggcaccaaccggaacgccagctact tcggcgagaacgccgacaagttcttcatcttccccaactacaccatcgtgtccgacttcggc agacccaacagcgctctggaaacccacagactggtggcctttctggaacgggccgacagcgt gatcagctgggacatccaggacgagaagaacgtgacctgccagctgaccttctgggaggcct ctgagagaaccatcagaagcgaggccgaggacagctaccacttcagcagcgccaagatgacc gccaccttcctgagcaagaaacaggaagtgaacatgagcgactccgccctggactgcgtgag ggacgaggccatcaacaagctgcagcagatcttcaacaccagctacaaccagacctacgaga agtatggcaatgtgtccgtgttcgagacaacaggcggcctggtggtgttctggcagggcatc aagcagaaaagcctggtggagctggaacggctcgccaaccggtccagcctgaacctgaccca caaccggaccaagcggagcaccgacggcaacaacgcaacccacctgtccaacatggaaagcg tgcacaacctggtgtacgcacagctgcagttcacctacgacaccctgcggggctacatcaac agagccctggcccagatcgccgaggcttggtgcgtggaccagcggcggaccctggaagtgtt caaagagctgtccaagatcaaccccagcgccatcctgagcgccatctacaacaagcctatcg ccgccagattcatgggcgacgtgctgggcctggccagctgcgtgaccatcaaccagaccagc gtgaaggtgctgcgggacatgaacgtgaaagagagcccaggccgctgctactccagacccgt ggtcatcttcaacttcgccaacagctcctacgtgcagtacggccagctgggcgaggacaacg agatcctgctggggaaccaccggaccgaggaatgccagctgcccagcctgaagatctttatc gccggcaacagcgcctacgagtatgtggactacctgttcaagcggatgatcgacctgagcag catctccaccgtggacagcatgatcgccctggacatcgacccccctggaaaacaccgacttcc gggtgctggaactgtacagccagaaagagctgcggagcagcaacgtgttcgacctggaagag atcatgcgggagttcaacagctacaagcagcgcgtgaaatacgtggaggacaaggtggtgga ccccctgcctccttacctgaagggcctggacgacctgatgagcggactgggcgctgccggaa aagccgtgggagtggccattggagctgtgggcggagctgtggcctctgtcgtggaaggcgtc gccacctttctgaagaaccccttcggcgccttcaccatcatcctggtggccattgccgtcgt gatcatcacctacctgatctacacccggcagcggagactgtgtacccagcccctgcagaacc tgttcccctacctggtgtccgccgatggcaccacagtgaccagcggctccaccaaggatacc agcctgcaggccccacccagctacgaagagagcgtgtacaacagcggcagaaagggccctgg ccctcccagctctgatgccagcacagccgcccctccctacaccaacgagcaggcctaccaga tgctgctggccctggctagactggatgccgagcagagggcccagcagaacggcaccgacagc ctggatggcagaaccggcacccaggacaagggccagaagcccaacctgctggaccggctgcg gcaccggaagaacggctaccggcacctgaaggacagcgacgaggaagagaacgtctgataa-

2727

CMV gB FL (SEQ ID NO: 2)

MESRIWCLVVCVNLCIVCLGAAVSSSSTRGTSATHSHHSSHTTSAAHSRSGSVSQRVTSSQT

VSHGVNETIYNTTLKYGDVVGVNTTKYPYRVCSMAQGTDLIRFERNIVCTSMKPINEDLDEG

IMVVYKRNIVAHTFKVRVYQKVLTFRRSYAYIHTTYLLGSNTEYVAPPMWEIHHINSHSQCY

SSYSRVIAGTVFVAYHRDSYENKTMQLMPDDYSNTHSTRYVTVKDQWHSRGSTWLYRETCNL

NCMVTITTARSKYPYHFFATSTGDVVDISPFYNGTNRNASYFGENADKFFIFPNYTIVSDFG

RPNSALETHRLVAFLERADSVISWDIQDEKNVTCQLTFWEASERTIRSEAEDSYHFSSAKMT

ATFLSKKQEVNMSDSALDCVRDEAINKLQQIFNTSYNQTYEKYGNVSVFETTGGLVVFWQGI

KQKSLVELERLANRSSLNLTHNRTKRSTDGNNATHLSNMESVHNLVYAQLQFTYDTLRGYIN

-continued

RALAQIAEAWCVDQRRTLEVFKELSKINPSAILSAIYNKPIAARFMGDVLGLASCVTINQTS

VKVLRDMNVKESPGRCYSRPVVIFNFANSSYVQYGQLGEDNEILLGNHRTEECQLPSLKIFI

AGNSAYEYVDYLFKRMIDLSSISTVDSMIALDIDPLENTDFRVLELYSQKELRSSNVFDLEE

IMREFNSYKQRVKYVEDKVVDPLPPYLKGLDDLMSGLGAAGKAVGVAIGAVGGAVASVVEGV

ATFLKNPFGAFTIILVAIAVVIITYLIYTRQRRLCTQPLQNLFPYLVSADGTTVTSGSTKDT

SLQAPPSYEESVYNSGRKGPGPPSSDASTAAPPYTNEQAYQMLLALARLDAEQRAQQNGTDS

LDGRTGTQDKGQKPNLLDRLRHRKNGYRHLKDSDEEENV--

CMV gB sol 750:

(SEQ ID NO: 3)

1-atggaaagccggatctggtgcctggtcgtgtgcgtgaacctgtgcatcgtgtgcctgggagc cgccgtgagcagcagcagcaccagaggcaccagcgccacacacagccaccacagcagccaca ccacctctgccgcccacagcagatccggcagcgtgtcccagagagtgaccagcagccagacc gtgtcccacggcgtgaacgagacaatctacaacaccaccctgaagtacggcgacgtcgtggg cgtgaataccaccaagtacccctacagagtgtgcagcatggcccagggcaccgacctgatca gattcgagcggaacatcgtgtgcaccagcatgaagcccatcaacgaggacctggacgagggc atcatggtggtgtacaagagaaacatcgtggcccacaccttcaaagtgcgggtgtaccagaa ggtgctgaccttccggcggagctacgcctacatccacaccacatacctgctgggcagcaaca ccgagtacgtggcccctcccatgtgggagatccaccacatcaacagccacagccagtgctac agcagctacagccgcgtgatcgccggcacagtgttcgtggcctaccaccgggacagctacga gaacaagaccatgcagctgatgcccgacgactacagcaacacccacagcaccagatacgtga ccgtgaaggaccagtggcacagcagaggcagcacctggctgtaccgggagacatgcaacctg aactgcatggtcaccatcaccaccgccagaagcaagtacccttaccacttcttcgccacctc caccggcgacgtggtggacatcagccccttctacaacggcaccaaccggaacgccagctact tcggcgagaacgccgacaagttcttcatcttccccaactacaccatcgtgtccgacttcggc agacccaacagcgctctggaaacccacagactggtggcctttctggaacgggccgacagcgt gatcagctgggacatccaggacgagaagaacgtgacctgccagctgaccttctgggaggcct ctgagagaaccatcagaagcgaggccgaggacagctaccacttcagcagcgccaagatgacc gccaccttcctgagcaagaaacaggaagtgaacatgagcgactccgccctggactgcgtgag ggacgaggccatcaacaagctgcagcagatcttcaacaccagctacaaccagacctacgaga agtatggcaatgtgtccgtgttcgagacaacaggcggcctggtggtgttctggcagggcatc aagcagaaaagcctggtggagctggaacggctcgccaaccggtccagcctgaacctgaccca caaccggaccaagcggagcaccgacggcaacaacgcaacccacctgtccaacatggaaagcg tgcacaacctggtgtacgcacagctgcagttcacctacgacaccctgcggggctacatcaac agagccctggcccagatcgccgaggcttggtgcgtggaccagcggcggaccctggaagtgtt caaagagctgtccaagatcaaccccagcgccatcctgagcgccatctacaacaagcctatcg ccgccagattcatgggcgacgtgctgggcctggccagctgcgtgaccatcaaccagaccagc gtgaaggtgctgcgggacatgaacgtgaaagagagcccaggccgctgctactccagacccgt ggtcatcttcaacttcgccaacagctcctacgtgcagtacggccagctgggcgaggacaacg agatcctgctggggaaccaccggaccgaggaatgccagctgcccagcctgaagatctttatc gccggcaacagcgcctacgagtatgtggactacctgttcaagcggatgatcgacctgagcag catctccaccgtggacagcatgatcgccctggacatcgacccccctggaaaacaccgacttcc -continued gggtgctggaactgtacagccagaaagagctgcggagcagcaacgtgttcgacctggaagag atcatgcgggagttcaacagctacaagcagcgcgtgaaatacgtggaggacaaggtggtgga ccccctgcctccttacctgaagggcctggacgacctgatgagcggaccgggcgctgccggaa aagccgtgggagtggccattggagctgtgggcggagctgtggcctctgtcgtggaaggcgtc gccacctttctgaagaactgataa-2256

Cmv gB sol 750

(SEQ ID NO: 4)

MESRIWCLVVCVNLCIVCLGAAVSSSSTRGTSATHSHHSSHTTSAAHSRSGSVSQRVTSSQT

VSHGVNETIYNTTLKYGDVVGVNTTKYPYRVCSMAQGTDLIRFERNIVCTSMKPINEDLDEG

IMVVYKRNIVAHTFKVRVYQKVLTFRRSYAYIHTTYLLGSNTEYVAPPMWEIHHINSHSQCY

SSYSRVIAGTVFVAYHRDSYENKTMQLMPDDYSNTHSTRYVTVKDQWHSRGSTWLYRETCNL

NCMVTITTARSKYPYHFFATSTGDVVDISPFYNGTNRNASYFGENADKFFIFPNYTIVSDFG

RPNSALETHRLVAFLERADSVISWDIQDEKNVTCQLTFWEASERTIRSEAEDSYHFSSAKMT

ATFLSKKQEVNMSDSALDCVRDEAINKLQQIFNTSYNQTYEKYGNVSVFETTGGLVVFWQGI

KQKSLVELERLANRSSLNLTHNRTKRSTDGNNATHLSNMESVHNLVYAQLQFTYDTLRGYIN

RALAQIAEAWCVDQRRTLEVFKELSKINPSAILSAIYNKPIAARFMGDVLGLASCVTINQTS

VKVLRDMNVKESPGRCYSRPVVIFNFANSSYVQYGQLGEDNEILLGNHRTEECQLPSLKIFI

AGNSAYEYVDYLFKRMIDLSSISTVDSMIALDIDPLENTDFRVLELYSQKELRSSNVFDLEE

IMREFNSYKQRVKYVEDKVVDPLPPYLKGLDDLMSGLGAAGKAVGVAIGAVGGAVASVVEGV

ATFLKN--

CMV gB sol 692:

(SEQ ID NO: 5)

1-atggaaagccggatctggtgcctggtcgtgtgcgtgaacctgtgcatcgtgtgcctgggagc cgccgtgagcagcagcagcaccagaggcaccagcgccacacacagccaccacagcagccaca ccacctctgccgcccacagcagatccggcagcgtgtcccagagagtgaccagcagccagacc gtgtcccacggcgtgaacgagacaatctacaacaccaccctgaagtacggcgacgtcgtggg cgtgaataccaccaagtacccctacagagtgtgcagcatggcccagggcaccgacctgatca gattcgagcggaacatcgtgtgcaccagcatgaagcccatcaacgaggacctggacgagggc atcatggtggtgtacaagagaaacatcgtggcccacaccttcaaagtgcgggtgtaccagaa ggtgctgaccttccggcggagctacgcctacatccacaccacatacctgctgggcagcaaca ccgagtacgtggcccctcccatgtgggagatccaccacatcaacagccacagccagtgctac agcagctacagccgcgtgatcgccggcacagtgttcgtggcctaccaccgggacagctacga gaacaagaccatgcagctgatgcccgacgactacagcaacacccacagcaccagatacgtga ccgtgaaggaccagtggcacagcagaggcagcacctggctgtaccgggagacatgcaacctg aactgcatggtcaccatcaccaccgccagaagcaagtacccttaccacttcttcgccacctc caccggcgacgtggtggacatcagccccttctacaacggcaccaaccggaacgccagctact tcggcgagaacgccgacaagttcttcatcttccccaactacaccatcgtgtccgacttcggc agacccaacagcgctctggaaacccacagactggtggcctttctggaacgggccgacagcgt gatcagctgggacatccaggacgagaagaacgtgacctgccagctgaccttctgggaggcct ctgagagaaccatcagaagcgaggccgaggacagctaccacttcagcagcgccaagatgacc gccaccttcctgagcaagaaacaggaagtgaacatgagcgactccgccctggactgcgtgag ggacgaggccatcaacaagctgcagcagatcttcaacaccagctacaaccagacctacgaga agtatggcaatgtgtccgtgttcgagacaacaggcggcctggtggtgttctggcagggcatc -continued aagcagaaaagcctggtggagctggaacggctcgccaaccggtccagcctgaacctgaccca caaccggaccaagcggagcaccgacggcaacaacgcaacccacctgtccaacatggaaagcg tgcacaacctggtgtacgcacagctgcagttcacctacgacaccctgcggggctacatcaac agagccctggcccagatcgccgaggcttggtgcgtggaccagcggcggaccctggaagtgtt caaagagctgtccaagatcaaccccagcgccatcctgagcgccatctacaacaagcctatcg ccgccagattcatgggcgacgtgctgggcctggccagctgcgtgaccatcaaccagaccagc gtgaaggtgctgcgggacatgaacgtgaaagagagcccaggccgccgctactccagacccgt ggtcatcttcaacttcgccaacagctcctacgtgcagtacggccagctgggcgaggacaacg agatcctgctggggaaccaccggaccgaggaatgccagctgcccagcctgaagatctttatc gccggcaacagcgcctacgagtatgtggactacctgttcaagcggatgatcgacctgagcag catctccaccgtggacagcatgatcgccctggacatcgacccccctggaaaacaccgacttcc gggtgctggaactgtacagccagaaagagctgcggagcagcaacgtgttcgacctggaagag atcatgcgggagttcaacagctacaagcagtgataa-2082

Cmv gB sol 692;

(SEQ ID NO: 6)

MESRIWCLVVCVNLCIVCLGAAVSSSSTRGTSATHSHHSSHTTSAAHSRSGSVSQRVTSSQT

VSHGVNETIYNTTLKYGDVVGVNTTKYPYRVCSMAQGTDLIRFERNIVCTSMKPINEDLDEG

IMVVYKRNIVAHTFKVRVYQKVLTFRRSYAYIHTTYLLGSNTEYVAPPMWEIHHINSHSQCY

SSYSRVIAGTVFVAYHRDSYENKTMQLMPDDYSNTHSTRYVTVKDQWHSRGSTWLYRETCNL

NCMVTITTARSKYPYHFFATSTGDVVDISPFYNGTNRNASYFGENADKFFIFPNYTIVSDFG

RPNSALETHRLVAFLERADSVISWDIQDEKNVTCQLTFWEASERTIRSEAEDSYHFSSAKMT

ATFLSKKQEVNMSDSALDCVRDEAINKLQQIFNTSYNQTYEKYGNVSVFETTGGLVVFWQGI

KQKSLVELERLANRSSLNLTHNRTKRSTDGNNATHLSNMESVHNLVYAQLQFTYDTLRGYIN

RALAQIAEAWCVDQRRTLEVFKELSKINPSAILSAIYNKPIAARFMGDVLGLASCVTINQTS

VKVLRDMNVKESPGRCYSRPVVIFNFANSSYVQYGQLGEDNEILLGNHRTEECQLPSLKIFI

AGNSAYEYVDYLFKRMIDLSSISTVDSMIALDIDPLENTDFRVLELYSQKELRSSNVFDLEE

IMREFNSYKQ--

CMV gH FL:

(SEQ ID NO: 7)

1-atgaggcctggcctgccctcctacctgatcatcctggccgtgtgcctgttcagccacctgct gtccagcagatacggcgccgaggccgtgagcgagcccctggacaaggctttccacctgctgc tgaacacctacggcagacccatccggtttctgcgggagaacaccacccagtgcacctacaac agcagcctgcggaacagcaccgtcgtgagagagaacgccatcagcttcaactttttccagag ctacaaccagtactacgtgttccacatgcccagatgcctgtttgccggccctctggccgagc agttcctgaaccaggtggacctgaccgagacactggaaagataccagcagcggctgaatacc tacgccctggtgtccaaggacctggccagctaccggtcctttagccagcagctcaaggctca ggatagcctcggcgagcagcctaccaccgtgccccctcccatcgacctgagcatcccccacg tgtggatgcctccccagaccacccctcacggctggaccgagagccacaccacctccggcctg cacagaccccacttcaaccagacctgcatcctgttcgacggccacgacctgctgtttagcac cgtgacccccctgcctgcaccagggcttctacctgatcgacgagctgagatacgtgaagatca ccctgaccgaggatttcttcgtggtcaccgtgtccatcgacgacgacacccccatgctgctg atcttcggccacctgcccagagtgctgttcaaggcccccctaccagcgggacaacttcatcct -continued gcggcagaccgagaagcacgagctgctggtgctggtcaagaaggaccagctgaaccggcact cctacctgaaggaccccgacttcctggacgccgccctggacttcaactacctggacctgagc gccctgctgagaaacagcttccacagatacgccgtggacgtgctgaagtccggacggtgcca gatgctcgatcggcggaccgtggagatggccttcgcctatgccctcgccctgttcgccgctg ccagacaggaagaggctggcgcccaggtgtcagtgcccagagccctggatagacaggccgcc ctgctgcagatccaggaattcatgatcacctgcctgagccagacccccccctagaaccaccct gctgctgtaccccacagccgtggatctggccaagagggccctgtggacccccaaccagatca ccgacatcacaagcctcgtgcggctcgtgtacatcctgagcaagcagaaccagcagcacctg atcccccagtgggccctgagacagatcgccgacttcgccctgaagctgcacaagacccatct ggccagctttctgagcgccttcgccaggcaggaactgtacctgatgggcagcctggtccaca gcatgctggtgcataccaccgagcggcgggagatcttcatcgtggagacaggcctgtgtagc ctggccgagctgtcccactttacccagctgctggcccaccctcaccacgagtacctgagcga cctgtacacccccctgcagcagcagcggcagacgggaccacagcctggaacggctgaccagac tgttccccgatgccaccgtgcctgctacagtgcctgccgccctgtccatcctgtccaccatg cagcccagcaccctggaaaccttccccgacctgttctgcctgcccctgggcgagagctttag cgccctgaccgtgtccgagcacgcgccctacatcgtgaccaatcagtacctgatcaagggca tcagctaccccgtgtccaccacagtcgcgggccagagcctgatcaccacccagaccgacagc cagaccaagtgcgagctgacccggaacatgcacaccacacacagcatcaccgtggccctgaa catcagcctggaaaactgcgctttctgtcagtctgccctgctggaatacgacgatacccagg gcgtgatcaacatcatgtacatgcacgacagcgacgacgtgctgttcgccctggacccctac aacgaggtggtggtgtccagcccccggacccactacctgatgctgctgaagaacggcaccgt gctggaagtgaccgacgtggtggtggacgccaccgacagcagactgctgatgatgagcgtgt acgccctgagcgccatcatcggcatctacctgctgtaccggatgctgaaaacctgctgataa-

2232

Cmv gH FL;

(SEQ ID NO: 8)

MRPGLPSYLIILAVCLFSHLLSSRYGAEAVSEPLDKAFHLLLNTYGRPIRFLRENTTQCTYN

SSLRNSTVVRENAISFNFFQSYNQYYVFHMPRCLFAGPLAEQFLNQVDLTETLERYQQRLNT

YALVSKDLASYRSFSQQLKAQDSLGEQPTTVPPPIDLSIPHVWMPPQTTPHGWTESHTTSGL

HRPHFNQTCILFDGHDLLFSTVTPCLHQGFYLIDELRYVKITLTEDFFVVTVSIDDDTPMLL

IFGHLPRVLFKAPYQRDNFILRQTEKHELLVLVKKDQLNRHSYLKDPDFLDAALDFNYLDLS

ALLRNSFHRYAVDVLKSGRCQMLDRRTVEMAFAYALALFAAARQEEAGAQVSVPRALDRQAA

LLQIQEFMITCLSQTPPRTTLLLYPTAVDLAKRALWTPNQITDITSLVRLVYILSKQNQQHL

IPQWALRQIADFALKLHKTHLASFLSAFARQELYLMGSLVHSMLVHTTERREIFIVETGLCS

LAELSHFTQLLAHPHHEYLSDLYTPCSSSGRRDHSLERLTRLFPDATVPATVPAALSILSTM

QPSTLETFPDLFCLPLGESFSALTVSEHVSYIVTNQYLIKGISYPVSTTVVGQSLIITQTDS

QTKCELTRNMHTTHSITVALNISLENCAFCQSALLEYDDTQGVINIMYMHDSDDVLFALDPY

NEVVVSSPRTHYLMLLKNGTVLEVTDVVVDATDSRLLMMSVYALSAIIGIYLLYRMLKTC--

CMV gH sol:

(SEQ ID NO: 9)

1-atgaggcctggcctgccctcctacctgatcatcctggccgtgtgcctgttcagccacctgct gtccagcagatacggcgccgaggccgtgagcgagcccctggacaaggctttccacctgctgc tgaacacctacggcagacccatccggtttctgcgggagaacaccacccagtgcacctacaac -continued agcagcctgcggaacagcaccgtcgtgagagagaacgccatcagcttcaactttttccagag ctacaaccagtactacgtgttccacatgcccagatgcctgtttgccggccctctggccgagc agttcctgaaccaggtggacctgaccgagacactggaaagataccagcagcggctgaatacc tacgccctggtgtccaaggacctggccagctaccggtcctttagccagcagctcaaggctca ggatagcctcggcgagcagcctaccaccgtgccccctcccatcgacctgagcatcccccacg tgtggatgcctccccagaccacccctcacggctggaccgagagccacaccacctccggcctg cacagaccccacttcaaccagacctgcatcctgttcgacggccacgacctgctgtttagcac cgtgacccccctgcctgcaccagggcttctacctgatcgacgagctgagatacgtgaagatca ccctgaccgaggatttcttcgtggtcaccgtgtccatcgacgacgacacccccatgctgctg atcttcggccacctgcccagagtgctgttcaaggcccccctaccagcgggacaacttcatcct gcggcagaccgagaagcacgagctgctggtgctggtcaagaaggaccagctgaaccggcact cctacctgaaggaccccgacttcctggacgccgccctggacttcaactacctggacctgagc gccctgctgagaaacagcttccacagatacgccgtggacgtgctgaagtccggacggtgcca gatgctcgatcggcggaccgtggagatggccttcgcctatgccctcgccctgttcgccgctg ccagacaggaagaggctggcgcccaggtgtcagtgcccagagccctggatagacaggccgcc ctgctgcagatccaggaattcatgatcacctgcctgagccagacccccccctagaaccaccct gctgctgtaccccacagccgtggatctggccaagagggccctgtggacccccaaccagatca ccgacatcacaagcctcgtgcggctcgtgtacatcctgagcaagcagaaccagcagcacctg atcccccagtgggccctgagacagatcgccgacttcgccctgaagctgcacaagacccatct ggccagctttctgagcgccttcgccaggcaggaactgtacctgatgggcagcctggtccaca gcatgctggtgcataccaccgagcggcgggagatcttcatcgtggagacaggcctgtgtagc ctggccgagctgtcccactttacccagctgctggcccaccctcaccacgagtacctgagcga cctgtacaccccctgcagcagcagcggcagacgggaccacagcctggaacggctgaccagac tgttccccgatgccaccgtgcctgctacagtgcctgccgccctgtccatcctgtccaccatg cagcccagcaccctggaaaccttccccgacctgttctgcctgccccctgggcgagagctttag cgccctgaccgtgtccgagcacgtgtcctacatcgtgaccaatcagtacctgatcaagggca tcagctaccccgtgtccaccacagtcgtgggccagagcctgatcatcacccagaccgacagc cagaccaagtgcgagctgacccggaacatgcacaccacacacagcatcaccgtggccctgaa catcagcctggaaaactgcgctttctgtcagtctgccctgctggaatacgacgatacccagg gcgtgatcaacatcatgtacatgcacgacagcgacgacgtgctgttcgccctggacccctac aacgaggtggtggtgtccagccccggacccactacctgatgctgctgaagaacggcaccgt gctggaagtgaccgacgtggtggtggacgccaccgactgataa-2151

CMV gH sol;

(SEQ ID NO: 10)

MRPGLPSYLIILAVCLFSHLLSSRYGAEAVSEPLDKAFHLLLNTYGRPIRFLRENTTQCTYN

SSLRNSTVVRENAISFNFFQSYNQYYVFHMPRCLFAGPLAEQFLNQVDLTETLERYQQRLNT

YALVSKDLASYRSFSQQLKAQDSLGEQPTTVPPPIDLSIPHVWMPPQTTPHGWTESHTTSGL

HRPHFNQTCILFDGHDLLFSTVTPCLHQGFYLIDELRYVKITLTEDFFVVTVSIDDDTPMLL

IFGHLPRVLFKAPYQRDNFILRQTEKHELLVLVKKDQLNRHSYLKDPDFLDAALDFNYLDLS

ALLRNSFHRYAVDVLKSGRCQMLDRRTVEMAFAYALALFAAARQEEAGAQVSVPRALDRQAA

LLQIQEFMITCLSQTPPRTTLLLYPTAVDLAKRALWTPNQITDITSLVRLVYILSKQNQQHL

-continued

IPQWALRQIADFALKLHKTHLASFLSAFARQELYLMGSLVHSMLVHTTERREIFIVETGLCS

LAELSHFTQLLAHPHHEYLSDLYTPCSSSGRRDHSLERLTRLFPDATVPATVPAALSILSTM

QPSTLETFPDLFCLPLGESFSALTVSEHVSYIVTNQYLIKGISYPVSTTVVGQSLIITQTDS

QTKCELTRNMHTTHSITVALNISLENCAFCQSALLEYDDTQGVINIMYMHDSDDVLFALDPY

NEVVVSSPRTHYLMLLKNGTVLEVTDVVVDATD--

CMV gL fl:

(SEQ ID NO: 11)

1-atgtgcagaaggcccgactgcggcttcagcttcagccctggacccgtgatcctgctgtggtg ctgcctgctgctgcctatcgtgtcctctgccgccgtgtctgtggcccctacagccgccgaga aggtgccagccgagtgccccgagctgaccagaagatgcctgctgggcgaggtgttcgagggc gacaagtacgagagctggctgcggcccctggtcaacgtgaccggcagagatggcccccctgag ccagctgatccggtacagacccgtgacccccgaggccgccaatagcgtgctgctggacgagg ccttcctggataccctggccctgctgtacaacaaccccgaccagctgagagccctgctgacc ctgctgtccagcgacaccgcccccagatggatgaccgtgatgcggggctacagcgagtgtgg agatggcagccctgccgtgtacacctgcgtggacgacctgtgcagaggctacgacctgacca gactgagctacggccggtccatcttcacagagcacgtgctgggcttcgagctggtgcccccc agcctgttcaacgtggCggCggccatccggaacgaggccaccagaaccaacagagccgtgcg gctgcctgtgtctacagccgctgcacctgagggcatcacactgttctacggcctgtacaacg ccgtgaaagagttctgcctccggcaccagctggatccccccctgctgagacacctggacaag tactacgccggcctgcccccagagctgaagcagaccagagtgaacctgcccgcccacagcag atatggccctcaggccgtggacgccagatgataa-840

CMV gL FL;

(SEQ ID NO: 12)

MCRRPDCGFSFSPGPVILLWCCLLLPIVSSAAVSVAPTAAEKVPAECPELTRRCLLGEVFEG

DKYESWLRPLVNVTGRDGPLSQLIRYRPVTPEAANSVLLDEAFLDTLALLYNNPDQLRALLT

LLSSDTAPRWMTVMRGYSECGDGSPAVYTCVDDLCRGYDLTRLSYGRSIFTEHVLGFELVPP

SLFNVVVAIRNEATRTNRAVRLPVSTAAAPEGITLFYGLYNAVKEFCLRHQLDPPLLRHLDK

YYAGLPPELKQTRVNLPAHSRYGPQAVDAR--

CMV gM FL:

(SEQ ID NO: 13)

1-atggcccccagccacgtggacaaagtgaacacccggacttggagcgccagcatcgtgttcat ggtgctgaccttcgtgaacgtgtccgtgcacctggtgctgtccaacttcccccacctgggct acccctgcgtgtactaccacgtggtggacttcgagcggctgaacatgagcgcctacaacgtg atgcacctgcacacccccatgctgtttctggacagcgtgcagctcgtgtgctacgccgtgtt catgcagctggtgtttctggccgtgaccatctactacctcgtgtgctggatcaagatcagca tgcggaaggacaagggcatgagcctgaaccagagcacccgggacatcagctacatgggcgac agcctgaccgccttcctgttcatcctgagcatggacaccttccagctgttcaccctgaccat gagcttccggctgcccagcatgatcgccttcatggccgccgtgcactttttctgtctgacca tcttcaacgtgtccatggtcacccagtaccggtcctacaagcggagcctgttcttcttctcc cggctgcaccccaagctgaagggcaccgtgcagttccggaccctgatcgtgaacctggtgga ggtggccctgggcttcaataccaccgtggtggctatggccctgtgctacggcttcggcaaca acttcttcgtgcggaccggccatatggtgctggccgtgttcgtggtgtacgccatcatcagc atcatctactttctgctgatcgaggccgtgttcttccagtacgtgaaggtgcagttcggcta ccatctgggcgcctttttcggcctgtgcggcctgatctaccccatcgtgcagtacgacacct -continued tcctgagcaacgagtaccggaccggcatcagctggtccttcggaatgctgttcttcatctgg gccatgttcaccacctgcagagccgtgcggtacttcagaggcagaggcagcggctccgtgaa gtaccaggccctggccacagcctctggcgaagaggtggccgccctgagccaccacgacagcc tggaaagcagacggctgcgggaggaagaggacgacgacgacgaggacttcgaggacgcctga taa-1119

CMV gM FL;

(SEQ ID NO: 14)

MAPSHVDKVNTRTWSASIVFMVLTFVNVSVHLVLSNFPHLGYPCVYYHVVDFERLNMSAYNV

MHLHTPMLFLDSVQLVCYAVFMQLVFLAVTIYYLVCWIKISMRKDKGMSLNQSTRDISYMGD

SLTAFLFILSMDTFQLFTLTMSFRLPSMIAFMAAVHFFCLTIFNVSMVTQYRSYKRSLFFFS

RLHPKLKGTVQFRTLIVNLVEVALGFNTTVVAMALCYGFGNNFFVRTGHMVLAVFVVYAIIS

IIYFLLIEAVFFQYVKVQFGYHLGAFFGLCGLIYPIVQYDTFLSNEYRTGISWSFGMLFFIW

AMFTTCRAVRYFRGRGSGSVKYQALATASGEEVAALSHHDSLESRRLREEEDDDDEDFEDA--

CMV gN FL:

(SEQ ID NO: 15)

1-atggaatggaacaccctggtcctgggcctgctggtgctgtctgtcgtggccagcagcaacaa cacatccacagccagcacccctagacctagcagcagcacccacgccagcactaccgtgaagg ctaccaccgtggccaccacaagcaccaccactgctaccagcaccagctccaccacctctgcc aagcctggctctaccacacacgaccccaacgtgatgaggccccacgcccacaacgacttcta caacgctcactgcaccagccacatgtacgagctgtccctgagcagctttgccgcctggtgga ccatgctgaacgccctgatcctgatgggcgccttctgcatcgtgctgcggcactgctgcttc cagaacttcaccgccaccaccaccaagggctactgataa-411

CMV gN FL;

(SEQ ID NO: 16)

MEWNTLVLGLLVLSVVASSNNTSTASTPRPSSSTHASTTVKATTVATTSTTTATSTSSTTSA

KPGSTTHDPNVMRPHAHNDFYNAHCTSHMYELSLSSFAAWWTMLNALILMGAFCIVLRHCCF

QNFTATTTKGY--

CMV gO FL:

(SEQ ID NO: 17)

1-atgggcaagaaagaaatgatcatggtcaagggcatccccaagatcatgctgctgattagcat cacctttctgctgctgtccctgatcaactgcaacgtgctggtcaacagccggggcaccagaa gatcctggccctacaccgtgctgtcctaccggggcaaagagatcctgaagaagcagaaagag gacatcctgaagcggctgatgagcaccagcagcgacggctaccggttcctgatgtaccccag ccagcagaaattccacgccatcgtgatcagcatggacaagttcccccaggactacatcctgg ccggacccatccggaacgacagcaccacccacatgtggttcgacctctacagcacccagctg cggaagcccgccaaatacgCgtacagcgagtacaaccacaccgcccacaagatcaccctgag gcctcccccttgtggcaccgtgcccagcatgaactgcctgagcgagatgctgaacgtgtcca agcggaacgacaccggcgagaagggcCgcggcaacttcaccaccttcaaccccatgttcttc aacgtgccccggtggaacaccaagctgtacatcggcagcaacaaagtgaacgtggacagcca gaccatctactttctgggcctgaccgccctgctgctgagatacgcccagcggaactgcaccc ggtccttctacctggtcaacgccatgagccggaacctgttccgggtgcccaagtacatcaac ggcaccaagctgaagaacaccatgcggaagctgaagcggaagcaggccctggtcaaagagca gccccagaagaagaacaagaagtcccagagcaccaccacccccctacctgagctacaccacct ccaccgccttcaacgtgaccaccaacgtgacctacagcgccacagccgccgtgaccagagtg -continued gccacaagcaccaccggctaccggcccgacagcaactttatgaagtccatcatggccaccca gctgagagatctggccacctgggtgtacaccaccctgcggtacagaaacgagcccttctgca agcccgaccggaacagaaccgccgcgagcgagctcatgaagaatacccacgtgctgatcaga aacgagacaccctacaccatccacggcaccctggacatgagcagcccgtactacaacgagac aatgagcgtggagaacgagacagccagcgacaacaacgaaaccacccccacctcccccagca cccggttccagcggaccttcatcgacccccctgtgggactacctggacagcctgctgttcctg gacaagatccggaacttcagcctgcagctgcccgcctacggcaatctgacccccccctgagca cagaagggccgccaacctgagcaccctgaacagcctgtggtggtggagccagtgataa-1422

CMV gO FL;

(SEQ ID NO: 18)

MGKKEMIMVKGIPKIMLLISITFLLLSLINCNVLVNSRGTRRSWPYTVLSYRGKEILKKQKE

DILKRLMSTSSDGYRFLMYPSQQKFHAIVISMDKFPQDYILAGPIRNDSITHMWFDFYSTQL

RKPAKYVYSEYNHTAHKITLRPPPCGTVPSMNCLSEMLNVSKRNDTGEKGCGNFTTFNPMFF

NVPRWNTKLYIGSNKVNVDSQTIYFLGLTALLLRYAQRNCTRSFYLVNAMSRNLFRVPKYIN

GTKLKNTMRKLKRKQALVKEQPQKKNKKSQSTTTPYLSYTTSTAFNVTTNVTYSATAAVTRV

ATSTTGYRPDSNFMKSIMATQLRDLATWVYTTLRYRNEPFCKPDRNRTAVSEFMKNTHVLIR

NETPYTIYGTLDMSSLYYNETMSVENETASDNNETTPTSPSTRFQRTFIDPLWDYLDSLLFL

DKIRNFSLQLPAYGNLTPPEHRRAANLSTLNSLWWWSQ--

CMV UL128 FL:

(SEQ ID NO: 19)

1-atgagccccaaggacctgacccccttcctgacaaccctgtggctgctcctgggccatagcag agtgcctagagtgcgggccgaggaatgctgcgagttcatcaacgtgaaccacccccccgagc ggtgctacgacttcaagatgtgcaaccggttcaccgtggccctgagatgccccgacggcgaa gtgtgctacagccccgagaaaaccgccgagatccggggcatcgtgaccaccatgacccacag cctgacccggcaggtggtgcacaacaagctgaccagctgcaactacaacccccctgtacctgg aagccgacggccggatcagatgcggcaaagtgaacgacaaggcccagtacctgctgggagcc gccggaagcgtgccctaccggtggatcaacctggaatacgacaagatcacccggatcgtggg cctggaccagtacctggaaagcgtgaagaagcacaagcggctggacgtgtgcagagccaaga tgggctacatgctgcagtgataa-519

CMV UL128 FL;

(SEQ ID NO: 20)

MSPKDLTPFLTTLWLLLGHSRVPRVRAEECCEFINVNHPPERCYDFKMCNRFTVALRCPDGE

VCYSPEKTAEIRGIVTTMTHSLTRQVVHNKLTSCNYNPLYLEADGRIRCGKVNDKAQYLLGA

AGSVPYRWINLEYDKITRIVGLDQYLESVKKHKRLDVCRAKMGYMLQ--

CMV UL130 FL:

(SEQ ID NO: 21)

1-atgctgcggctgctgctgagacaccacttccactgcctgctgctgtgtgccgtgtgggccac cccttgtctggccagcccttggagcaccctgaccgccaaccagaaccctagccccccttggt ccaagctgacctacagcaagccccacgacgccgccaccttctactgcccctttctgtacccc agccctcccagaagccccctgcagttcagcggcttccagagagtgtccaccggccctgagtg ccggaacgagacactgtacctgctgtacaaccgggagggccagacactggtggagcggagca gcacctgggtgaaaaaagtgatctggtatctgagcggccggaaccagaccatcctgcagcgg atgcccagaaccgccagcaagcccagcgacggcaacgtgcagatcagcgtggaggacgccaa aatcttcggcgcccacatggtgcccaagcagaccaagctgctgagattcgtggtcaacgacg gcaccagatatcagatgtgcgtgatgaagctggaaagctgggcccacgtgttccgggactac -continued tccgtgagcttccaggtccggctgaccttcaccgaggccaacaaccagacctacaccttctg cacccaccccaacctgatcgtgtgataa-648

CMV UL130 FL;

(SEQ ID NO: 22)

MLRLLLRHHFHCLLLCAVWATPCLASPWSTLTANQNPSPPWSKLTYSKPHDAATFYCPFLYP

SPPRSPLQFSGFQRVSTGPECRNETLYLLYNREGQTLVERSSTWVKKVIWYLSGRNQTILQR

MPRTASKPSDGNVQISVEDAKIFGAHMVPKQTKLLRFVVNDGTRYQMCVMKLESWAHVFRDY

SVSFQVRLTFTEANNQTYTFCTHPNLIV--

CMV UL131 FL:

(SEQ ID NO: 23)

1-atgcggctgtgcagagtgtggctgtccgtgtgcctgtgtgccgtggtgctgggccagtgcca gagagagacagccgagaagaacgactactaccgggtgccccactactgggatgcctgcagca gagccctgcccgaccagacccggtacaaatacgtggagcagctcgtggacctgaccctgaac taccactacgacgccagccacggcctggacaacttcgacgtgctgaagcggatcaacgtgac cgaggtgtccctgctgatcagcgacttccggcggcagaacagaagaggcggcaccaacaagc ggaccaccttcaacgccgctggctctctggcccctcacgccagatccctggaattcagcgtg cggctgttcgccaactgataa-393

CMV UL131 FL;

(SEQ ID NO: 24)

MRLCRVWLSVCLCAVVLGQCQRETAEKNDYYRVPHYWDACSRALPDQTRYKYVEQLVDLTLN

YHYDASHGLDNFDVLKRINVTEVSLLISDFRRQNRRGGTNKRTTFNAAGSLAPHARSLEFSV

RLFAN--

ParvoB19.Opti.VP1

(SEQ ID NO: 25)

acgcgtacaaaacaaaATGTCTAAGAAATCTGGTAAATGGTGGGAATCTGATGATAAATTTGCTAAGGC

TGTTTACCAACAATTTGTTGAATTTTACGAAAAGGTTACTGGTACTGATTTGGAATTGATTCAAATTTTGAAGGA

TCATTACAACATTTCTTTGGATAATCCATTGGAAAATCCATCTTCATTGTTTGATTTGGTTGCTAGAATTAAGAA

CAACTTGAAGAACTCTCCAGATTTGTATTCTCATCATTTCCAATCTCATGGTCAATTGTCTGATCATCCACATGC

TTTATCTTCATCTTCATCTCATGCTGAACCAAGAGGTGAAAATGCTGTTTTATCTTCTGAAGATTTGCATAAACC

AGGTCAAGTTTCTGTTCAATTGCCAGGTACTAATTACGTTGGTCCAGGTAATGAATTGCAAGCTGGTCCACCACA

ATCTGCTGTTGATTCTGCTGCTAGAATTCATGATTTCAGATACTCTCAATTGGCTAAGTTGGGTATTAATCCATA

TACTCATTGGACTGTTGCTGATGAAGAATTGTTGAAGAACATTAAGAATGAAACTGGTTTTCAAGCTCAAGTTGT

TAAAGATTACTTCACTTTGAAAGGTGCTGCTGCTCCAGTTGCTCATTTTCAAGGTTCTTTGCCAGAAGTTCCAGC

TTATAACGCTTCTGAAAAATATCCATCTATGACATCTGTTAATTCTGCTGAAGCATCTACTGGTGCAGGTGGAGG

TGGTTCTAATTCTGTTAAATCTATGTGGTCTGAAGGTGCTACTTTTTCTGCTAATTCAGTTACTTGTACTTTCTC

TAGACAATTCTTGATTCCATATGATCCAGAACATCATTACAAAGTTTTTTCACCAGCTGCTTCATCTTGTCATAA

TGCTTCAGGTAAAGAAGCTAAGGTTTGTACTATTTCTCCAATTATGGGTTATTCTACTCCTTGGAGATACTTGGA

TTTTAATGCTTTGAACTTGTTTTTTTCTCCATTGGAATTTCAACATTTGATTGAAAACTACGGTTCTATTGCTCC

AGATGCTTTGACTGTTACTATTTCTGAAATTGCTGTTAAGGATGTTACTGATAAAACAGGTGGTGGTGTTCAAGT

TACTGATTCTACTACTGGTAGATTGTGCATGTTGGTTGATCATGAATACAAATACCCATACGTTTTGGGTCAAGG

TCAAGATACTTTGGCTCCAGAATTGCCAATTTGGGTTTATTTTCCACCACAATACGCTTATTTGACTGTTGGTGA

TGTTAATACTCAAGGTATTTCTGGTGATTCTAAAAAGTTGGCTTCTGAAGAATCTGCTTTTTACGTTTTGGAACA

TTCTTCTTTTCAATTGTTGGGTACTGGTGGTACTGCTTCTATGTCTTACAAATTTCCACCAGTTCCACCTGAAAA

TTTGGAAGGTTGTTCTCAACATTTTTACGAAATGTACAATCCATTGTATGGTTCTAGATTGGGTGTTCCAGATAC

-continued

TTTGGGTGGTGATCCAAAATTTAGATCTTTGACTCATGAAGATCATGCTATTCAACCACAAAATTTCATGCCAGG

TCCATTGGTTAATTCTGTTTCTACTAAAGAAGGTGATTCTTCTAATACAGGTGCTGGTAAAGCATTGACTGGTTT

GTCTACTGGTACTTCTCAAAACACTAGAATTTCTTTAAGACCAGGTCCAGTTTCACAACCATATCATCATTGGGA

TACTGATAAGTACGTTACTGGTATTAATGCTATTTCACATGGTCAAACTACTTATGGTAATGCTGAAGATAAAGA

ATATCAACAAGGTGTTGGTAGATTTCCAAACGAAAAAGAACAATTGAAACAATTGCAAGGTTTGAATATGCATAC

TTACTTTCCAAACAAAGGTACTCAACAATACACTGATCAAATTGAAAGACCATTGATGGTTGGTTCTGTTTGGAA

TAGAAGAGCTTTGCATTATGAATCTCAATTGTGGTCTAAGATTCCAAATTTAGATGATTCTTTCAAGACTCAATT

TGCTGCTTTGGGTGGTTGGGGTTTGCATCAACCTCCACCACAAATTTTCTTGAAGATTTTGCCACAATCTGGTCC

AATTGGTGGTATTAAATCTATGGGTATTACTACTTTGGTTCAATATGCTGTTGGTATTATGACTGTTACAATGAC

TTTTAAGTTGGGTCCAAGAAAAGCTACAGGTAGATGGAATCCACAACCAGGTGTTTATCCACCACATGCTGCTGG

TCATTTGCCTTACGTTTTGTATGATCCAACTGCTACTGATGCTAAACAACATCATAGACATGGTTATGAAAAACC

TGAAGAATTGTGGACTGCTAAATCTAGAGTTCATCCATTGTAATGAgtcgac

ParvoB19.Opti.VP2

(SEQ ID NO: 26)

cctaggacaaaacaaaATGACATCTGTTAATTCTGCTGAAGCATCTACTGGTGCAGGTGGAGGTGGTTCTAATTC

TGTTAAATCTATGTGGTCTGAAGGTGCTACTTTTTCTGCTAATTCAGTTACTTGTACTTTCTCTAGACAATTCTT

GATTCCATATGATCCAGAACATCATTACAAAGTTTTTTCACCAGCTGCTTCATCTTGTCATAATGCTTCAGGTAA

AGAAGCTAAGGTTTGTACTATTTCTCCAATTATGGGTTATTCTACTCCTTGGAGATACTTGGATTTTAATGCTTT

GAACTTGTTTTTTTCTCCATTGGAATTTCAACATTTGATTGAAAACTACGGTTCTATTGCTCCAGATGCTTTGAC

TGTTACTATTTCTGAAATTGCTGTTAAGGATGTTACTGATAAAACAGGTGGTGGTGTTCAAGTTACTGATTCTAC

TACTGGTAGATTGTGCATGTTGGTTGATCATGAATACAAATACCCATACGTTTTGGGTCAAGGTCAAGATACTTT

GGCTCCAGAATTGCCAATTTGGGTTTATTTTCCACCACAATACGCTTATTTGACTGTTGGTGATGTTAATACTCA

AGGTATTTCTGGTGATTCTAAAAAGTTGGCTTCTGAAGAATCTGCTTTTTACGTTTTGGAACATTCTTCTTTTCA

ATTGTTGGGTACTGGTGGTACTGCTTCTATGTCTTACAAATTTCCACCAGTTCCACCTGAAAATTTGGAAGGTTG

TTCTCAACATTTTTACGAAATGTACAATCCATTGTATGGTTCTAGATTGGGTGTTCCAGATACTTTGGGTGGTGA

TCCAAAATTTAGATCTTTGACTCATGAAGATCATGCTATTCAACCACAAAATTTCATGCCAGGTCCATTGGTTAA

TTCTGTTTCTACTAAAGAAGGTGATTCTTCTAATACAGGTGCTGGTAAAGCATTGACTGGTTTGTCTACTGGTAC

TTCTCAAAACACTAGAATTTCTTTAAGACCAGGTCCAGTTTCACAACCATATCATCATTGGGATACTGATAAGTA

CGTTACTGGTATTAATGCTATTTCACATGGTCAAACTACTTATGGTAATGCTGAAGATAAAGAATATCAACAAGG

TGTTGGTAGATTTCCAAACGAAAAAGAACAATTGAAACAATTGCAAGGTTTGAATATGCATACTTACTTTCCAAA

CAAAGGTACTCAACAATACACTGATCAAATTGAAAGACCATTGATGGTTGGTTCTGTTTGGAATAGAAGAGCTTT

GCATTATGAATCTCAATTGTGGTCTAAGATTCCAAATTTAGATGATTCTTTCAAGACTCAATTTGCTGCTTTGGG

TGGTTGGGGTTTGCATCAACCTCCACCACAAATTTTCTTGAAGATTTTGCCACAATCTGGTCCAATTGGTGGTAT

TAAATCTATGGGTATTACTACTTTGGTTCAATATGCTGTTGGTATTATGACTGTTACAATGACTTTTAAGTTGGG

TCCAAGAAAAGCTACAGGTAGATGGAATCCACAACCAGGTGTTTATCCACCACATGCTGCTGGTCATTTGCCTTA

CGTTTTGTATGATCCAACTGCTACTGATGCTAAACAACATCATAGACATGGTTATGAAAAACCTGAAGAATTGTG

GACTGCTAAATCTAGAGTTCATCCATTGTAATGAgcggccgc

The invention claimed is:

1. An immunogenic composition comprising:

(i) a first polypeptide antigen derived from the group consisting of a viral pathogen and a bacterial pathogen, and (ii) a self-replicating RNA molecule encapsulated within a liposome, wherein said self-replicating RNA molecule cannot induce production of infectious viral particles, encodes a second polypeptide antigen from a viral pathogen, and can promote T cell-mediated immunity as well as humoral immunity to both first and second antigens, wherein said first and second antigens are antigens from different pathogens, wherein the self-replicating RNA molecule is not encapsulated in a virus-like particle; and wherein the liposome encapsulating the self-replicating RNA molecule does not include capsid protein or envelope glycoproteins.

2. The immunogenic composition of claim 1, wherein said second polypeptide antigen is a Cytomegalovirus (CMV) antigen.

3. The immunogenic composition of claim 1, wherein said first polypeptide antigen is in the form of a virus-like particle (VLP).

4. The immunogenic composition of claim 1, wherein said first polypeptide antigen is a soluble polypeptide and said second polypeptide antigen is a soluble or membrane anchored polypeptide.

5. The immunogenic composition of claim 1, wherein the self-replicating RNA is an alphavirus-derived RNA replicon.

6. The immunogenic composition of claim 1, wherein the self-replicating RNA molecule comprises one or more modified nucleotides.

7. The immunogenic composition of claim 1, wherein the first polypeptide antigen and second polypeptide antigen are both viral antigens.

8. The immunogenic composition of claim 7, wherein one viral antigen is an antigen from CMV.

9. An immunogenic composition comprising:

(i) a first viral polypeptide antigen, and (ii) a self-replicating RNA molecule encapsulated within a liposome, wherein said self-replicating RNA molecule cannot induce production of infectious viral particles, encodes a second viral polypeptide antigen from a viral pathogen, and can promote T cell-mediated immunity as well as humoral immunity to both first and second antigens, wherein said first and second antigens are antigens from different viral pathogens, wherein one viral antigen is a Parvovirus antigen.

10. The immunogenic composition of claim 9, wherein the Parvovirus antigen comprises an amino acid sequence encoded by SEQ ID NO: 25 or 26.

11. The immunogenic composition of claim 1, further comprising an adjuvant.

12. An immunogenic composition comprising: (i) a Parvovirus polypeptide antigen, and (ii) a self-replicating RNA molecule that encodes a CMV polypeptide antigen.

13. A method for inducing an immune response in a subject comprising administering to a subject in need thereof a therapeutically effective amount of a composition according to claim 1.

* * * * *